US008450341B2

(12) United States Patent
Eastwood et al.

(10) Patent No.: US 8,450,341 B2
(45) Date of Patent: May 28, 2013

(54) SUBSTITUTED INDOLIN-2-ONE DERIVATIVES AND THEIR USE AS P38 MITOGEN-ACTIVATED KINASE INHIBITORS

(75) Inventors: Paul Robert Eastwood, Rubi (ES); Jacob Gonzalez Rodriguez, Molins de Rei (ES); Victor Giulio Matassa, La Floresta (ES)

(73) Assignee: Almirall, S.A., Barcelona (ES)

( * ) Notice: Subject to any disclaimer, the term of this patent is extended or adjusted under 35 U.S.C. 154(b) by 281 days.

(21) Appl. No.: 12/989,696

(22) PCT Filed: Apr. 16, 2009

(86) PCT No.: PCT/EP2009/002783
§ 371 (c)(1),
(2), (4) Date: Oct. 26, 2010

(87) PCT Pub. No.: WO2009/132774
PCT Pub. Date: Nov. 5, 2009

(65) Prior Publication Data
US 2011/0046097 A1    Feb. 24, 2011

(30) Foreign Application Priority Data

Apr. 28, 2008   (EP) ..................... 08382017

(51) Int. Cl.
| A01N 43/42 | (2006.01) |
| A01N 43/82 | (2006.01) |
| A01N 43/38 | (2006.01) |
| A61K 31/44 | (2006.01) |
| A61K 31/41 | (2006.01) |
| A61K 31/40 | (2006.01) |
| A61K 31/405 | (2006.01) |
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |
| C07D 271/06 | (2006.01) |
| C07D 271/12 | (2006.01) |
| C07D 413/00 | (2006.01) |
| C07D 498/00 | (2006.01) |
| C07D 261/20 | (2006.01) |
| C07D 249/00 | (2006.01) |
| C07D 487/02 | (2006.01) |
| C07D 495/02 | (2006.01) |
| C07D 497/02 | (2006.01) |
| C07D 405/00 | (2006.01) |
| C07D 409/00 | (2006.01) |
| C07D 411/00 | (2006.01) |
| C07D 209/36 | (2006.01) |

(52) U.S. Cl.
USPC ........... 514/300; 514/302; 514/303; 514/364; 514/414; 514/415; 546/113; 546/118; 546/121; 548/133; 548/241; 548/262.4; 548/453; 548/484

(58) Field of Classification Search
USPC .. 514/300, 302, 303, 414, 415, 364; 546/113, 546/118, 121; 548/133, 241, 262.4, 453, 548/454, 484
See application file for complete search history.

(56) References Cited

U.S. PATENT DOCUMENTS

| 4,550,166 A | 10/1985 | Moran et al. |
| 4,959,368 A | 9/1990 | Awaya et al. |
| 5,414,088 A | 5/1995 | Saal et al. |
| 6,586,447 B1 | 7/2003 | Lyssikatos et al. |
| 8,106,190 B2 | 1/2012 | Kuramochi et al. |
| 2003/0166724 A1 | 9/2003 | Hangeland |
| 2005/0131014 A1 | 6/2005 | Collini et al. |
| 2006/0106048 A1 | 5/2006 | Inoue et al. |
| 2007/0213341 A1 | 9/2007 | Chen et al. |
| 2008/0009486 A1 | 1/2008 | Chen et al. |
| 2010/0120731 A1 | 5/2010 | Juan et al. |
| 2010/0130517 A1 | 5/2010 | Amador et al. |
| 2010/0227881 A1 | 9/2010 | Javaloyes et al. |
| 2011/0053936 A1 | 3/2011 | Eastwood et al. |

FOREIGN PATENT DOCUMENTS

| CN | 1502608 A | 6/2004 |
| EP | 0 549 892 A1 | 7/1993 |
| EP | 0 743 066 A2 | 11/1996 |
| JP | 57-203068 | 12/1982 |
| JP | 10-79183 | 3/1989 |
| JP | 1996-005887 | 1/1996 |
| JP | 9-104638 | 4/1997 |
| WO | WO 87/04928 | 8/1987 |
| WO | WO 91/04974 | 4/1991 |
| WO | WO 91/06545 | 5/1991 |
| WO | WO 99/01449 | 1/1999 |
| WO | WO 99/64400 | 12/1999 |
| WO | WO 00/63204 | 10/2000 |
| WO | WO 00/66583 | 11/2000 |
| WO | WO 01/01986 A1 | 1/2001 |

(Continued)

OTHER PUBLICATIONS

International Search Report for PCT/EP2009/002783 (WO 2009/132774) dated May 28, 2009 (2 pages).
International Search Report for PCT/EP2009/002458 (WO 2009/124692) dated Jun. 3, 2009 (3 pages).
U.S. Appl. No. 12/376,499, filed Apr. 1, 2009, Javaloyes et al.
U.S. Appl. No. 12/529,490, filed Sep. 1, 2009, Juan et al.
U.S. Appl. No. 12/597,187, filed Jan. 7, 2010, Amador et al.
U.S. Appl. No. 12/936,784, filed Oct. 26, 2010, Eastwood et al.
U.S. Appl. No. 13/509,076, filed May 10, 2012, Bosch et al.

(Continued)

*Primary Examiner* — Sreeni Padmanabhan
*Assistant Examiner* — Sarah Pihonak
(74) *Attorney, Agent, or Firm* — Finnegan, Henderson, Farabow, Garrett & Dunner, LLP

(57) ABSTRACT

The present disclosure is directed to new inhibitors of the p38 mitogen-activated protein kinase having the general formula (I), processes for preparation thereof, pharmaceutical compositions thereof, and methods of use thereof.

12 Claims, 4 Drawing Sheets

FOREIGN PATENT DOCUMENTS

Figure 1:
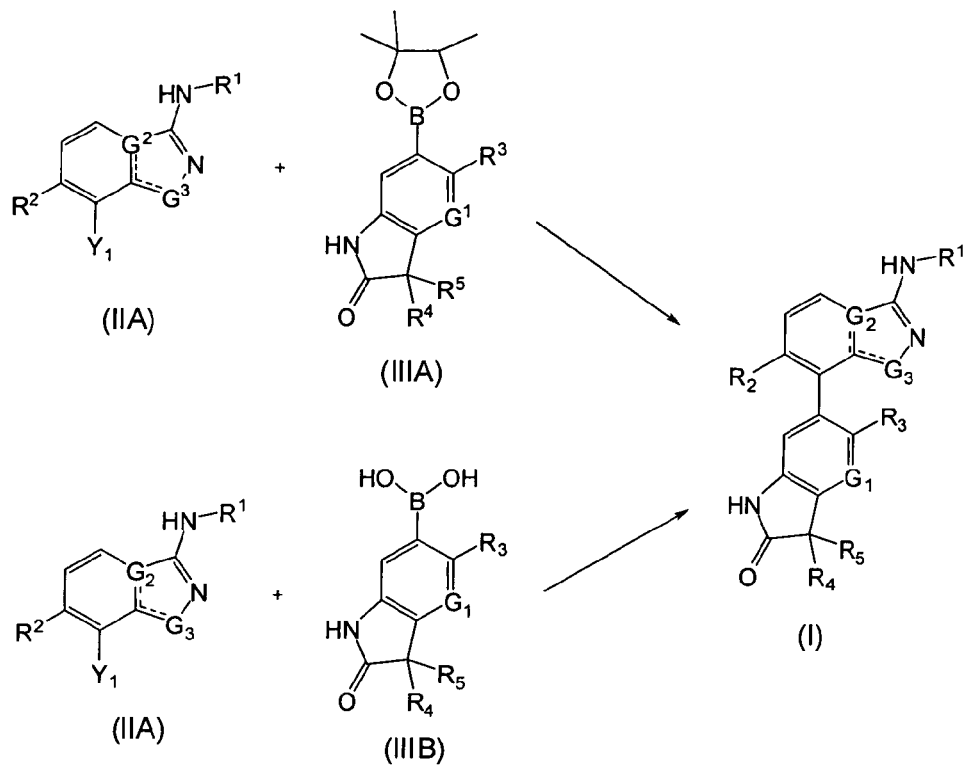

| | | |
|---|---|---|
| WO | WO 01/29042 A1 | 4/2001 |
| WO | WO 02/02549 A1 | 1/2002 |
| WO | WO 02/46184 A1 | 6/2002 |
| WO | WO 02/058695 A1 | 8/2002 |
| WO | WO 02/072576 A1 | 9/2002 |
| WO | WO 02/072579 A1 | 9/2002 |
| WO | WO 03/008413 A1 | 1/2003 |
| WO | WO 03/033502 A1 | 4/2003 |
| WO | WO 03/043998 A1 | 5/2003 |
| WO | WO 03/087087 A2 | 10/2003 |
| WO | WO 03/097062 A1 | 11/2003 |
| WO | WO 03/103590 A2 | 12/2003 |
| WO | WO 2004/010995 A1 | 2/2004 |
| WO | WO 2004/011470 A1 | 2/2004 |
| WO | WO 2004/014900 A1 | 2/2004 |
| WO | WO 2004/020438 A2 | 3/2004 |
| WO | WO 2004/020440 A1 | 3/2004 |
| WO | WO 2004/074290 A1 | 9/2004 |
| WO | WO 2005/000232 A2 | 1/2005 |
| WO | WO 2005/018624 A2 | 3/2005 |
| WO | WO 2005/032551 A1 | 4/2005 |
| WO | WO 2005/070929 A1 | 8/2005 |
| WO | WO 2005/073219 A1 | 8/2005 |
| WO | WO 2005/121142 A1 | 12/2005 |
| WO | WO 2007/063925 A1 | 6/2007 |
| WO | WO 2007/098214 A1 | 8/2007 |
| WO | WO 2007/104664 A1 | 9/2007 |
| WO | WO 2008/017461 A1 | 2/2008 |
| WO | WO 2008/045393 A1 | 4/2008 |
| WO | WO 2008/107125 A1 | 9/2008 |
| WO | WO 2008/131922 A1 | 11/2008 |
| WO | WO 2009/124692 A1 | 10/2009 |
| WO | WO 2011/057757 A1 | 5/2011 |

OTHER PUBLICATIONS

Adams, R. H., et al., "Essential role of p38α MAP kinase in placental but not embryonic cardiovascular development," Molecular Cell, 6:109-116 (2000).

Allen, M., et al., "Deficiency of the stress kinase p38a results in embryonic lethality: characterization of the kinase dependance of stress responses of enzyme-deficient embryonic stem cells," J. Exp. Med. 191(5):859-869 (2000).

Amato, J. S., et al., "Synthesis of 1-tert-Butyl-4-chlorpiperidine: generation of an N-tert-Butyl group by the reaction of a dimethyliminium salt with methylmagnesium chloride," The Journal of Organic Chemistry, 70(5):1930-1933 (2005).

Balaban, A. T., "Aminyloxides (nitroxides) from 1-hydroxy-2-indolinones," Tetrahedron, 30:739-744 (1974).

Bao, J. et al., "p38 MAP kinase inhibitors: metabolically stabilized piperidine-substituted quinolinones and naphthyridinones," Bioorganic & Medicinal Chemistry Letters, 16:64-68 (2006).

Baxter, I. et al., "The oxidation of 5-arylsulphonamido-3,3-dimethyloxindoles and related compounds," Journal of the Chemical Society (C), pp. 952-955 (1971).

Beardmore, V. A., et al., "Generation and characterization of p38β (MAPK11) gene targeted mice," Molecular and Cellular Biology, 25(23):10454-10464 (2005).

Brancho, D., et al., "Mechanism of p38 MAP kinase activation in vivo," Genes & Development, 17:1969-1978 (2003).

Cheng, C., et al., "The friedlander synthesis of quinolines," Org. React., Chapter 2:37-201 (1982).

English Language Abstract for CN 1502608 (2004).

English Language Abstract for JP 57-203068 from esp@cenet, dated Dec. 13, 1982.

English Language Abstract for JP 1996-005887 (1996).

English Language Abstract for JP 10-79183 (1989).

English Language Abstract for JP 09-104638 (1997).

English Language Abstract for WO 1987/04928, (1987).

English Language Abstract for WO 1991/04974, (1991).

English Language Abstract for WO 1991/06545.

English Language Abstract for WO 2004/011470.

English Language Abstract for WO 2007/063925.

Fang, Cheng-Lin, et al., "Dimerization of a 3-substituted oxidindole at C-3 and Its application to the synthesis of (±)-folicanthine," Journal of the American Chemical Society, 116:9480-9486 (1994).

Gavrin, L. K., et al., "Inhibition of Tpl2 kinase and TNF-α production with 1,7-naphthyridine-3-carbonitriles: synthesis and structure-activity relationships," Bioorganic & Medicinal Chemistry Letters, 15:5288-5292 (2005).

Gilman, H., et al., "Some substituted Isoquinolines," Journal of American Chemical Society, 69(8):1946-1948 (1947).

Hale, K. K., et al., "Differential expression and activation of p38 mitogen-activated protein kinase α, β, γ, and δ in inflammatory cell lineages," The Journal of Immunology, 162:4246-4252 (1999).

Hideshima, T., et al., "Targeting p38 MAPK inhibits multiple myeloma cell growth in the bone marrow milieu," Blood, 101(2):703-705 (2003).

Hildesheim, J., et al., "p38 Mitogen-activated protein kinase inhibitor protects the epidermis against the acute damaging effects of ultraviolet Irradiation by blocking apoptosis and inflammatory responses," The Journal of Investigative Dermatology, 122:497-502 (2004).

Hollenbach, E., et al., "Inhibition of RICK/Nuclear factor-κb and p38 signaling attenuates the inflammatory response in a murine model of crohn disease," The Journal of Biological Chemistry, 280(15):14981-14988 (2005).

International Search Report, PCT/EP2007/006981, mailed Oct. 18, 2007.

International Search Report, PCT/EP2008/003357, mailed Aug. 12, 2008.

International Search Report, PCT/EP2008/001616, mailed May 28, 2008.

International Search Report, PCT/EP2010/006817, mailed May 2, 2011.

Jin, Shan-Xue, et al., "p38 Mitogen-activated protein kinase is activated after a spinal nerve ligation in spinal cord microglia and dorsal root ganglion neurons and contributes to the generation of neuropathic pain," The Journal of Neuroscience, 23(10):4017-4022 (2003).

Karp, G., et al., "Preparation and alkylation of regioisomeric tetrahydrophthalimide-substituted Indolin-2(3H)-ones," Journal of Heterocyclic Chemistry, 31:1513-1520 (1994).

Katsoulidis, E., et al., "Role of the p38 mitogen-activated protein kinase pathway in cytokine-mediated hematopoietic suppression in myelodysplastic syndromes," Cancer Research, 65(19):9029-9037 (2005).

Kotlyarov, A., et al., "MAPKAP Kinase 2 is essential for LPS-induced TNF-α biosynthesis," Nature Cell Biology, 1:94-97 (1999).

Kumar, S., et al., "p38 Map kinases: key signaling molecules as therapeutic targets for inflammatory diseases," Nature Reviews Drug Discovery, 2:717-726 (2003).

Kyriakis, J. M., et al., "Mammalian mitogen-activated protein kinase signal transduction pathways activated by stress and inflammation," Physiological Reviews, 81(2):807-869 (2001).

Lee, H. J., et al., "Biochemical and physiological effects of benzheterocycles and related compounds," Journal of Agricultural and Food Chemistry, 43:2722-2727 (1995).

Lee, J. C., et al., "A protein kinase involved in the regulation of inflammatory cytokine biosynthesis," Nature, 372(22/29):739-746 (1994).

Lyga, J., et al., "Structural replacements for the benzoxazinone protox Inhibitors," Pesticide Science, 55:281-287 (1999).

Miyaura, N., et al., "Palladium-catalyzed cross-coupling reactions of organoboron compounds," Chem. Rev., 95(7):2457-2483 (1995).

Moran, D. B., et al., "Synthesis of (pyridinyl)-1,2,4-triazolo[4,3-a]pyridines," J. Heterocyclic Chem., 23:1071-1077 (1986).

Müller, C., et al., "Chiral Pyrrolo[2,3-d]pyrimidine and Pyrimido[4,5-b]indole derivatives: structure-activity relationships of potent, highly stereoselective $A_1$-adenosine receptor antagonists," Journal of Medicinal Chemistry, 39:2482-2491 (1996).

Negishi, E., et al., "Novel stereoselective alkenyl-aryl coupling via nickel-catalysed reaction of alkenylalanes with aryl halides," J.C.S. Chem. Comm.,pp. 596-597 (1976).

Nick, J. A., et al., "Selective suppression of neutrophil accumulation in ongoing pulmonary inflammation by systemic Inhibition of p38 mitogen-activated protein kinase," The Journal of Immunology, 169:5260-5269 (2002).
Notice of Allowance dated Nov. 8, 2010 for U.S. Appl. No. 12/376,499.
Notice of Allowance dated May 10, 2012 for U.S. Appl. No. 12/529,490.
Office Action dated Aug. 2, 2010 for U.S. Appl. No. 12/376,499.
Office Action dated Oct. 28, 2011 for U.S. Appl. No. 12/529,490.
Office Action dated Feb. 8, 2012 for U.S. Appl. No. 12/597,187.
Pargellis, C., et al., "Inhibitors of p38 mitogen-activated protein kinase for the treatment of rheumatoid arthritis," Current Opinion in Investigational Drugs, 4(5):566-571 (2003).
Patani, G. A., et al., "Bioisosterism: a rational approach in drug design," Chemical Reviews, ACS, 96(8):3147-3176 (1996).
Sabio, G., et al., "p38γ regulates the localisation of SAP97 in the cytoskeleton by modulating its interaction with GKAP," The EMBO Journal, 24(6):1134-1145 (2005).
Saccani, S., et al., "p38-dependent marking of inflammatory genes for increased NF-κb recruitment," Nature Immunology, 3(1):69-75 (2002).
Santilli, A. A., et al., "7-Deazapurines v. synthesis and reactions of 7-amino-5,7-dihydro-4-methyl-2-phenyl-6H-pyrrolo[2,3-d]pyrimidin-6-one," Journal of Heterocyclic Chemistry, 12:12911293 (1975).
Schäfers, M., et al., "Tumor necrosis factor-α induces mechanical allodynia after spinal nerve ligation by activation of p38 MAPK in primary sensory neurons," The Journal of Neuroscience, 23(7):2517-2521 (2003).
See, F., et al., "p38 MAP kinase as a therapeutic target in cardiovascular disease," Drug Discovery Today: Therapeutic Strategies, 1(2):149-154 (2004).
Shi, Y., et al., "In the cellular garden of forking paths: how p38 MAPKs signal for downstream assistance," Biol. Chem., 383(10):1519-1536 (2002).
Tamura, K., et al., "Requirement for p38α in erythropoietin expression: a role for stress kinases in erythropoiesis," Cell, 102:221-231 (2000).
Tsuda, M., et al., "Activation of p38 mitogen-activated protein kinase in spinal hyperactive microglia contributes to pain hypersensitivity following peripheral nerve injury," GLIA, 89:89-95 (2004).
Underwood, D. C., et al., "SB 239063, a p38 MAPK inhibitor, reduces neutrophilia, inflammatory cytokines, MMP-9, and fibrosis in lung," Am. J. Physiol. Lung Cell Mol. Physiol., 279:L895-L902 (2000).
Waetzig, G. H., et al., "p38 Mitogen-activated protein kinase Is activated and linked to TNF-α signaling in inflammatory bowel disease," The Journal of Immunology, 168:5342-5351 (2002).
Wang, X. S., et al., "Molecular cloning and characterization of a novel p38 mitogen-activated protein kinase," The Journal of Biological Chemistry, 272(38):23668-23674 (1997).
Zhou, Z., et al., "TNFR-induced the NF-κB, but not the ERK, p38MAPK or JNK activation, mediates TNF-induced ICAM-1 and VCAM-1 expression on endothelial cells," Cellular Signalling, 19:1238-1248 (2007).

SUBSTITUTED INDOLIN-2-ONE DERIVATIVES AND THEIR USE AS P38 MITOGEN-ACTIVATED KINASE INHIBITORS

This application is a national stage filing under 35 U.S.C. §371 of International Application No. PCT/EP2009/002783 filed on Apr. 16, 2009, which claims priority to European Application No. 08382017.5 filed on Apr. 28, 2008, the disclosures of which are incorporated herein by reference in their entireties.

The present invention relates to new inhibitors of the p38 mitogen-activated protein kinase.

MAP kinases are evolutionary conserved enzymes translating membrane signals into gene expression responses. In mammals, four MAPK families can be distinguished: extracellular signal-related kinases (ERK1/2), Jun amino terminal kinases (JNK1/2/3), p38 proteins (alpha, beta, gamma and delta) and ERK5. The regulation of these proteins is exerted by a three-tier cascade composed of MAPK, MAPK kinase, and MAPK kinase.

p38 MAPK was originally identified as the target of CSAIDs (cytokine suppressive anti-inflammatory drugs), having a central role in the signal transduction pathway leading to the production of TNF-alpha and other cytokines (Lee et al, 1984). p38 is activated by phosphorylation of Thr and Tyr by either MKK3, MKK4, or MKK6 (Kyriakis and Avruch, 2001) in response to stress and pro-inflammatory stimuli. In turn, p38 phosphorylates its effectors in Ser and Thr residues, namely protein kinase phosphatases and transcription factors, such as ATF-2, MEF2, MAPKAPK2, MSK1/2 or MNK1/2. Altogether this activation cascade results in control of gene expression through four different mechanisms: transcription factor activation; mRNA stabilization; mRNA translation; and histone phosphorylation at NF-kB binding sites in chromatin (Shi and Gaestel, 2002; Sacanni et al, 2001).

There are four different p38 isoforms encoded by separate genes: p38 alpha, beta, gamma and delta, each one showing a distinct tissue expression pattern. As assessed by mRNA and protein levels (Beardmore et al, 2005; Wang et al, 1997), p38 alpha and beta are ubiquitously expressed, with p38 beta expression being more relevant in CNS tissues (brain, cortex, cerebellum, hippocampus, etc). The expression of p38 gamma is more prominent in skeletal muscle while p38 delta is localized mainly in the heart, kidney, lung and adrenal gland. At the cellular level, p38 alpha and delta seem to be the most relevant isoforms in immune cells (monocytes, macrophages, neutrophils and T cells) (Hale et al, 1999). Pharmacological inhibition with specific p38alpha/beta inhibitors as well as gene targeting studies have indicated that p38alpha is the isoform regulating inflammatory responses most probably through its downstream substrate MAPKAP-K2 (Kotlyarov et al, 1999). Likewise, this isoform is necessary in early embryonic development as p38alpha KO (knock-out) mice die in embryonic day 12.5 due to placental insufficiency and vascular defects (Allen et al, 2000; Tamura et al, 2000; Adams et al, 2000), a phenotype that is also reproduced in the MKK3/MKK6 double KO mice (Brancho et al, 2003). In contrast, p38 beta, gamma and delta knock-out mice do not show any developmental deficiencies (Beardmore et al, 2005; Sabio et al, 2005). p38 beta KO mice appear to respond similarly to pro-inflammatory stimuli (LPS) as wild type controls, indicating that this isoform does not have a role in inflammation (Beardmore et al 2005).

The contribution of the p38MAPK pathway to inflammation has been studied both in vitro and in vivo by employing different chemical series of p38 inhibitors (Pargellis and Regan, 2003; Kumar et al, 2003). The most widely used inhibitor molecule, SB203580, is, in fact, a dual p38alpha/beta inhibitor. Inhibition of p38 abrogates the release of TNF-alpha as well as other pro-inflammatory cytokines like IL-1, IL-6, and IL-8, in PBMC, whole blood, or the human monocytic cell line THP-1.

By virtue of the involvement of p38 in TNF-alpha production, inhibitors of p38 have been tested in animal models of diseases in which TNF-alpha has a pathophysiological role. p38 inhibition decreases murine collagen-induced arthritis and rat adjuvant-induced arthritis severity (Pargellis and Regan, 2003). Furthermore, p38 inhibitors also improve bone resorption in animal models of arthritis, probably due to the implication of p38 MAPK in the differentiation of osteoclasts. p38 inhibition attenuates the inflammatory response in a murine model of Crohn's disease and diminishes TNF-alpha production in human Crohn's disease patient biopsies (Hollenbach et al 2005; Waetzig et al, 2002). Due to the exclusive usage of the p38 pathway by neutrophils, p38 has also been considered a target for chronic obstructive pulmonary disease (COPD) (Nick et al, 2002). p38 inhibition reduces neutrophilia, inflammatory cytokines, MMP-9 and fibrosis in lung (Underwood et al, 2000). In skin models of irradiation, inhibition of p38 protects the epidermis against acute ultraviolet radiation exposure by blocking apoptosis and inflammatory responses (Hildesheim et al, 2004). p38 inhibition also reverses hematopoietic defects in bone marrow from patients with myelodysplastic syndromes, in which TNF-alpha overproduction has a pathophysiological role (Katsoulidis et al, 2005).

In hematopoietic malignancies, a study has shown that p38 inhibitors can block the proliferation of multiple myeloma cells by inhibiting the production of IL-6 and VEGF in bone marrow stromal cells (Hideshima et al, 2002).

p38 is involved in key cellular mechanisms such as apoptosis, fibrosis and cellular hypertrophy, which are common to cardiac and vascular pathologies. Pharmacological inhibition of p38 has proven useful in improving ischemia-reperfusion injury, cerebral focal ischemia, acute coronary syndrome, chronic heart failure and post-myocardial infarction remodelling (See et al, 2004).

Experimental inhibition of p38 has been reported effective in reducing pain in animal models of neuropathy that rely on COX-2 expression and TNF-alpha production by glial cells (Schafers et al, 2003; Jin et al, 2003; Tsuda et al, 2004).

Therefore, the compounds of the invention may be useful in the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include, without limitation, autoimmune diseases, immune and inflammatory diseases, destructive bone disorders, neoplastic disorders, neurodegenerative disorders, viral diseases, infectious diseases, cardiovascular diseases, angiogenesis-related disorders, and pain-related disorders.

Autoimmune diseases which may be prevented or treated include, but are not limited to, rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, and Addison's disease.

Immune and inflammatory diseases which may be prevented or treated include, but are not limited to, asthma, COPD, respiratory distress syndrome, acute or chronic pancreatitis, graft versus-host disease, Behcet syndrome, inflammatory eye conditions such as conjunctivitis and uveitis, psoriasis, contact dermatitis, atopic dermatitis, sarcoidosis, gout, pyresis, transplant rejection, allergic rhinitis and allergic conjunctivitis.

Cardiovascular diseases which may be prevented or treated include, but are not limited to, ischemia-reperfusion injury, cerebral focal ischemia, acute coronary syndrome, congestive heart failure, cardiomyopathy, myocarditis, atherosclerosis, vasculitis and restenosis.

Destructive bone disorders which may be prevented or treated include, but are not limited to, osteoporosis, osteoarthritis and multiple myeloma-related bone disorder.

Neoplastic disorders which may be prevented or treated include, but are not limited to, solid tumors such as Kaposi's sarcoma, metastatic melanoma, and hematopoietic malignancies such as acute or chronic myelogenous leukemia and multiple myeloma.

Neurodegenerative diseases which may be prevented or treated include, but are not limited to, Parkinson's disease, Alzheimer's disease, neurodegenerative disease caused by traumatic injury, and Huntington's disease.

Viral diseases which may be prevented or treated include, but are not limited to, acute hepatitis infection (including hepatitis A, hepatitis B and hepatitis C), HIV infection, Epstein-Barr infection, CMV retinitis, SARS or avian influenza A infection.

Infectious diseases which may be prevented or treated include, but are not limited to, sepsis, septic shock, endotoxic shock, Gram negative sepsis, toxic shock syndrome, Shigellosis, and cerebral malaria.

Angiogenesis-related disorders which may be prevented or treated include, but are not limited to, hemangiomas, ocular neovascularization, macular degeneration and diabetic retinopathy.

Pain-related disorders which may be prevented or treated include, but are not limited to, neuropathic pain (such as diabetic neuropathy, post-herpetic or trigeminal neuralgia), cancer-related pain, chronic pain (such as lower back pain syndrome), and inflammatory pain.

Other miscellaneous diseases or disorders which may be prevented or treated include, but are not limited to, myelodysplastic syndrome, cachexia, endometriosis, acute skin injuries such as sunburn, and wound healing.

In view of the physiological effects mediated by inhibition of the p38 mitogen-activated protein kinase, several compounds have been recently disclosed for the treatment or prevention of rheumatoid arthritis, ischemia-reperfusion injury, cerebral focal ischemia, acute coronary syndrome, COPD, Crohn's disease, irritable bowel syndrome, adult respiratory distress syndrome, osteoporosis, neurodegenerative diseases such as Alzheimer's disease, rheumatoid spondylitis, psoriasis, atherosclerosis, osteoarthritis and multiple myeloma. See for example WO 99/01449, WO 00/63204, WO 01/01986, WO 01/29042, WO 02/046184, WO 02/058695, WO 02/072576, WO 02/072579, WO 03/008413, WO 03/033502, WO 03/087087, WO 03/097062, WO 03/103590, WO 2004/010995, WO 2004/014900, WO 2004/020438, WO 2004/020440, WO 2005/018624, WO 2005/032551, WO 2005/073219.

It has now been found that certain substituted indolin-2-one derivatives are novel potent inhibitors of the p38 mitogen-activated protein kinase and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible of being improved by inhibition of the p38 mitogen-activated protein kinase; and methods of treatment of pathological conditions or diseases susceptible to amelioration by inhibition of the p38 mitogen-activated protein kinase comprising the administration of the compounds of the invention to a subject in need of treatment.

FIG. 1. depicts synthetic routes to compounds of formula (I).

Figure 2:
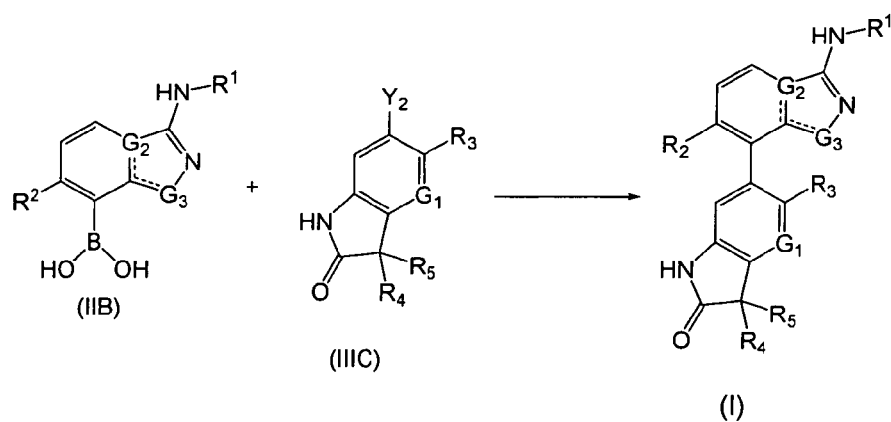

FIG. 2. depicts an alternative synthetic route to compounds of formula (I).

Figure 3:
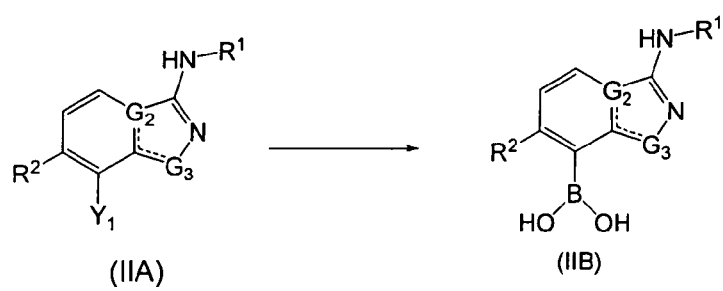

FIG. 3. depicts a synthetic route to compounds of formula (IIB).

Figure 4:
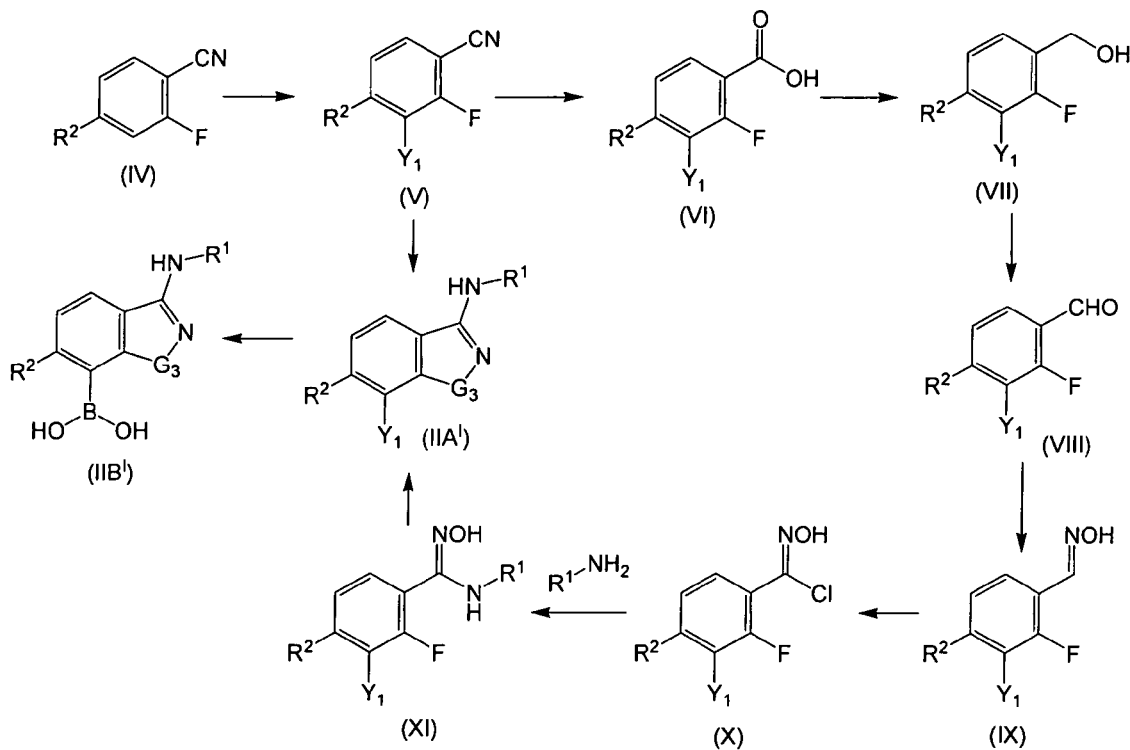

FIG. 4. depicts synthetic routes to compounds of formula (IIA$^I$) and (IIB$^I$).

Figure 5:
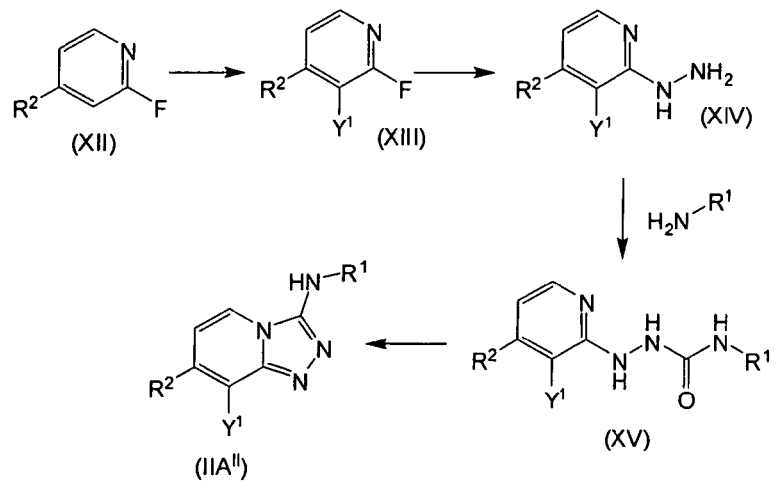

FIG. 5. depicts a synthetic route to compounds of formula (IIA$^{II}$).

Figure 6:
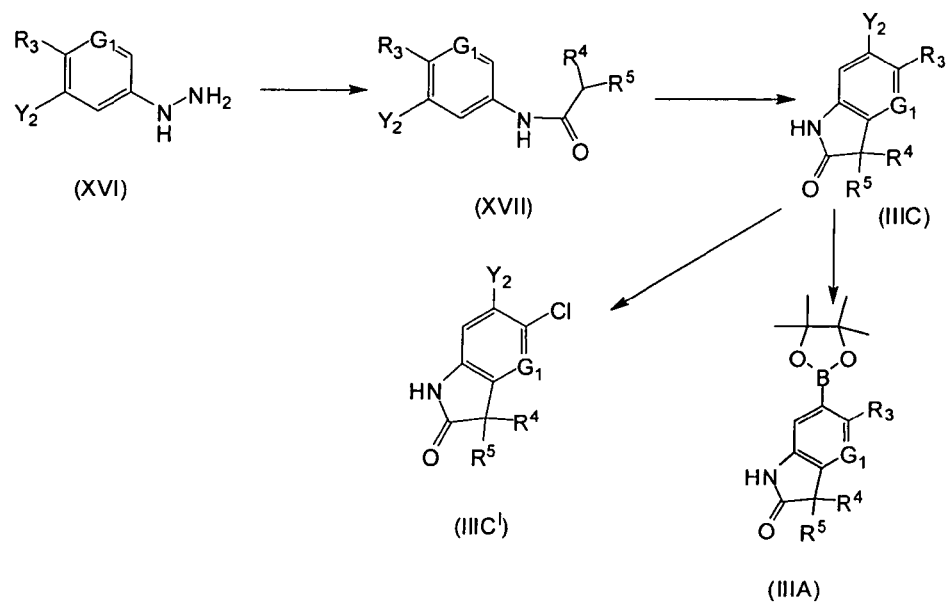

FIG. 6. depicts a synthetic route to intermediate compounds of formula (IIIA), (IIIC) and (IIIC$^I$).

Figure 7:
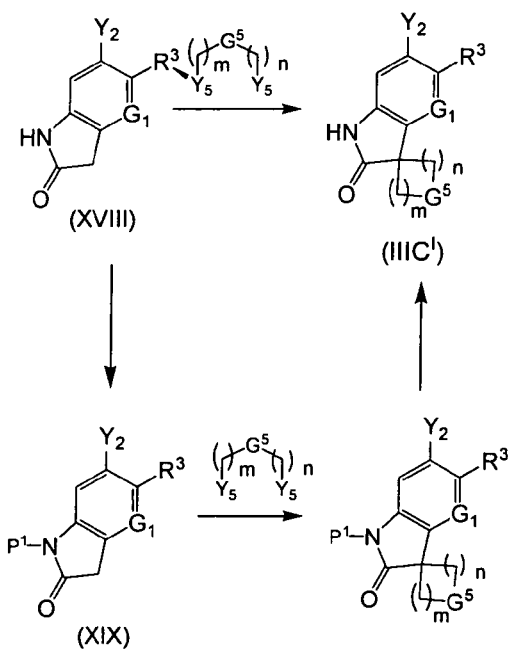

FIG. 7. depicts synthetic routes to intermediate compounds of formula (IIIC$^I$).

Figure 8:
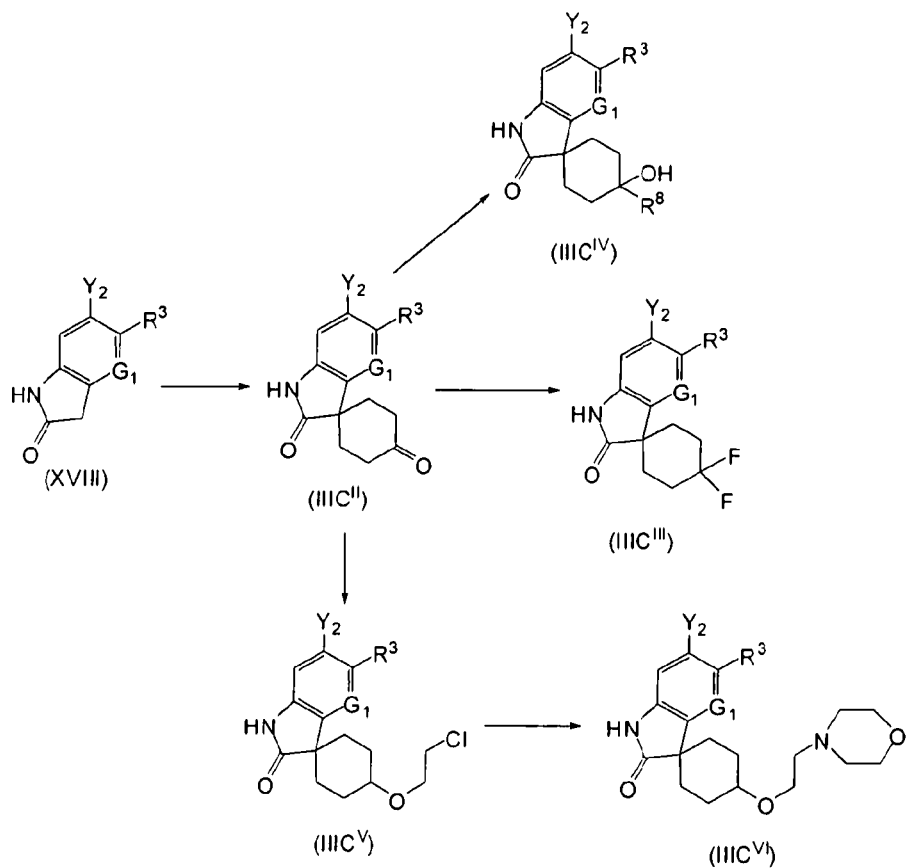

FIG. 8. depicts synthetic routes to compounds of formula (IIIC$^{II}$ to IIIC$^{VI}$).

Figure 9:
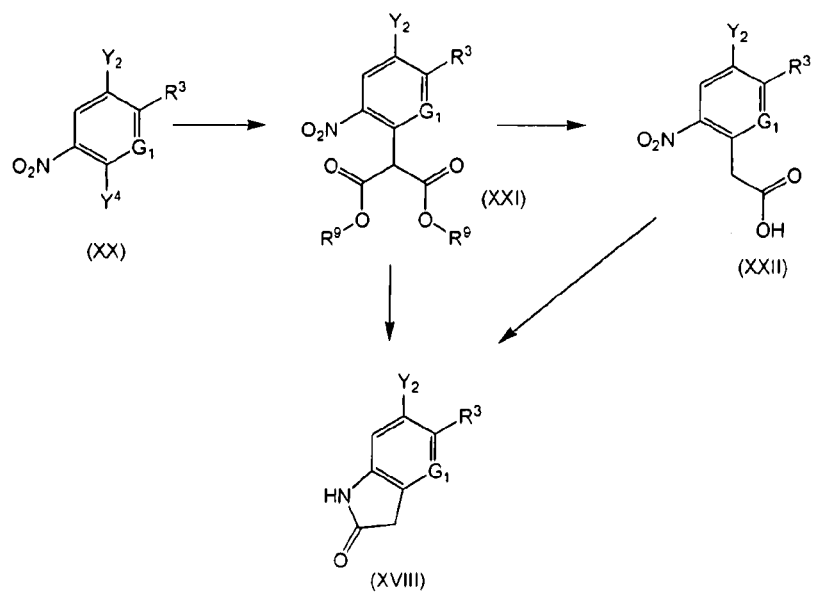

FIG. 9. depicts synthetic routes to compounds of formula (XVIII).

The present invention is directed to new substituted derivatives represented by formula (I):

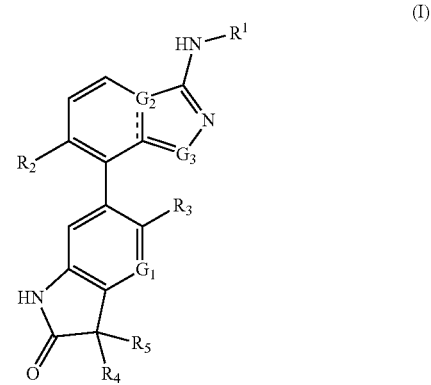

wherein
$R^1$ is selected from the group consisting of a hydrogen atom, a $C_{3-6}$ cycloalkyl group, a $C_{3-6}$ cycloalkyl-$C_{1-2}$ alkylene group and $C_{5-10}$ aryl-$C_{1-2}$ alkylene group, wherein the cycloalkyl and aryl group are optionally substituted by 1 or 2 substituents selected from linear or branched $C_{1-4}$ alkyl or $C_{1-4}$ alkoxy groups.

$R^2$ is selected from the group consisting of hydrogen atoms and methyl groups.

R³ is selected from the group consisting of hydrogen atoms and halogen atoms.

R⁴ and R⁵ each independently represent a $C_{1-3}$ alkyl group, or

R⁴ and R⁵ form together with the carbon atom to which they are attached a cyclic group of formula

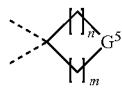

wherein n and m each independently represent an integer from 1 to 2 and G⁵ is selected from —O— and —C(R⁷R⁸)— wherein R⁷ is selected from the group consisting of hydrogen atom, halogen atom, hydroxyl group, morpholine and morpholino-ethoxy group, R⁸ is selected from the group consisting of hydrogen atom, halogen atom and $C_{1-4}$ alkyl group, G¹ is selected from a nitrogen atom or a group —CH=

G² is selected from a nitrogen atom or an aromatic carbon atom, and

G³ is selected from a nitrogen atom or an oxygen atom and pharmaceutically acceptable salts and N-oxides thereof.

As used herein the term $C_{1-4}$ alkyl embraces optionally substituted, linear or branched hydrocarbon radicals having 1 to 4 carbon atoms, for example 1 to 3 carbon atoms. Thus, the alkyl radical may be unsubstituted or substituted with one or more, for example 1, 2 or 3, halogen atoms, hydroxy or $C_{1-4}$ alkoxy groups. When an alkyl radical carries 2 or more substituents, the substituents may be the same or different. Preferably said alkyl radical is unsubstituted.

Examples include methyl, ethyl, n-propyl, i-propyl, n-butyl, sec-butyl and tert-butyl radicals.

As used herein the term $C_{1-4}$ alkoxy embraces linear or branched oxygen containing radicals each having 1 to 4 carbon atoms. The $C_{1-4}$ alkoxy may be unsubstituted or substituted with one or more, for example 1, 2 or 3, halogen atoms, preferably fluorine or chlorine atoms. Preferably said $C_{1-4}$ alkoxy group is unsubstituted.

Examples include methoxy, ethoxy, n-propoxy, i-propoxy, n-butoxy, sec-butoxy and tert-butoxy radicals.

As used herein, the term cycloalkyl embraces saturated carbocyclic radicals and, unless otherwise specified, a cycloalkyl radical typically has from 3 to 7 carbon atoms, preferably from 3 to 6, more preferably from 3 to 5 carbon atoms and most preferably from 3 to 4 carbon atoms.

Examples include cyclopropyl, cyclobutyl, cyclopentyl, cyclohexyl and cycloheptyl.

As used herein, the term $C_5$-$C_{14}$ aryl radical embraces typically a monocyclic or polycyclic aryl radical such as phenyl or naphthyl, anthranyl or phenanthryl, and is preferably a $C_5$-$C_{10}$ aryl radical such as phenyl or naphthyl. Phenyl is preferred. When an aryl radical carries 2 or more substituents, the substituents may be the same or different. Preferably said aryl radical is unsubstituted.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X−) is associated with the positive charge of the N atom. X− may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X− is preferably an anion selected from chloride, bromide, iodide, sulphate, nitrate, acetate, maleate, oxalate, succinate or trifluoroacetate. More preferably X− is chloride, bromide, trifluoroacetate or methanesulphonate.

As used herein, an N-oxide is formed from the tertiary basic amines or imines present in the molecule, using a convenient oxidising agent.

When G² represents an aromatic carbon atom and G³ represents a nitrogen atom, one of the nitrogen atoms in the ring system including G² and G³ is protonated.

Typically, R¹ represents a hydrogen atom, a cyclopropyl group, a cyclopropylmethyl group, or a benzyl group wherein the benzyl group is optionally substituted by a methoxy group. Preferably, R¹ represents a hydrogen atom or a cyclopropyl group.

Typically, R² presents a methyl group.

Typically, R³ represents a hydrogen atom.

Typically, R⁴ and R⁵ each independently represent a methyl group, or R⁴ and R⁵ form together with the carbon atom to which they are attached a cyclic group of formula

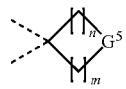

wherein n and m each independently represent an integer from 1 to 2 and G⁵ is selected from —O— and —C(R⁷R⁸)—, wherein R⁷ is selected from the group consisting of a hydrogen atom, a fluorine atom, a hydroxyl group and a morpholino-ethoxy group, R⁸ is selected from a hydrogen atom, a fluorine atom or a methyl group, Typically, G² represents an aromatic carbon atom.

Typically, G³ represents an oxygen atom.

In a preferred embodiment of the invention, R¹ represents a hydrogen atom or a cyclopropyl group, R² represents a methyl group, R³ represents a hydrogen atom, R⁴ and R⁵ each independently represent a methyl group, or R⁴ and R⁵ form together with the carbon atom to which they are attached a cyclic group of formula

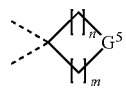

wherein n and m each independently represent an integer from 1 to 2 and G⁵ is selected from —O— and —C(R⁷R⁸)—, wherein R[7] is selected from the group consisting of a hydrogen atom, a fluorine atom, a hydroxyl group and a morpholino-ethoxy group, R[8] is selected from a hydrogen atom, a fluorine atom or a methyl group, $G^2$ represents an aromatic carbon atom and $G^3$ represents an oxygen atom.

Particular individual compounds of the invention include:
6'-(3-(Cyclopropylamino)-6-methylbenzo[d]isoxazol-7-yl) spiro[cyclopentane-1,3'-indolin]-2'-one
6'-(3-(Cyclopropylamino)-benzo[d]isoxazol-7-yl)spiro[cyclopentane-1,3'-indolin]-2'-one
5'-Chloro-6'-(3-(cyclopropylamino)benzo[d]isoxazol-7-yl) spiro[cyclopentane-1,3'-indolin]-2'-one
6-(3-(Cyclopropylamino)-6-methylbenzo[d]isoxazol-7-yl)-2',3',5',6'-tetrahydrospiro[indoline-3,4'-pyran]-2-one
6'-(3-(Cyclopropylamino)-6-methylbenzo[d]isoxazol-7-yl)-4,4-difluorospiro[cyclohexane-1,3'-indolin]-2'-one
6-(3-(Cyclopropylamino)-6-methylbenzo[d]isoxazol-7-yl)-3,3-dimethylindolin-2-one
6'-(3-(Cyclopropylamino)-6-methylbenzo[d]isoxazol-7-yl)-2,3,5,6-tetrahydrospiro[pyran-4,3'-pyrrolo[3,2-b]pyridin]-2'(1'H)-one
6'-(3-(Cyclopropylamino)-6-methylbenzo[d]isoxazol-7-yl)-4-hydroxy-4-methylspiro[cyclohexane-1,3'-pyrrolo[3,2-b]pyridin]-2'(1'H)-one
6'-(3-(Cyclopropylamino)-6-methylbenzo[d]isoxazol-7-yl)-4-hydroxy-4-methylspiro[cyclohexane-1,3'-pyrrolo[3,2-b]pyridin]-2'(1'H)-one
6-(3-(4-Methoxybenzylamino)-6-methylbenzo[d]isoxazol-7-yl)-2',3',5',6'-tetrahydrospiro[indoline-3,4'-pyran]-2-one
6-(3-Amino-6-methylbenzo[d]isoxazol-7-yl)-2',3',5',6'-tetrahydrospiro[indoline-3,4'-pyran]-2-one
6'-(3-Amino-6-methylbenzo[d]isoxazol-7-yl)-4-hydroxy-4-methylspiro[cyclohexane-1,3'-indolin]-2'-one
6'-(3-Amino-6-methylbenzo[d]isoxazol-7-yl)-4-(2-morpholinoethoxy)spiro[cyclohexane-1,3'-indolin]-2'-one
6'-(3-Amino-6-methyl-1,2-benzisoxazol-7-yl)-4,4-difluorospiro[cyclohexane-1,3'-indol]-2'(1H)-one
6-(3-Amino-6-methyl-1,2-benzisoxazol-7-yl)-3,3-dimethyl-1,3-dihydro-2H-indol-2-one
6-(3-Amino-6-methyl-1H-indazol-7-yl)-2',3',5',6'-tetrahydrospiro[indoline-3,4'-pyran]-2-one
6'-[3-(Cyclopropylamino)][1,2,4]triazolo[4,3-a]pyridin-8-yl] spiro[cyclopentane-1,3'-indol]-2'(1'H)-one
6'-(3-Amino[1,2,4]triazolo[4,3-a]pyridin-8-yl)spiro[cyclopentane-1,3'-indol]-2'(1'H)-one
6'-{3-[(Cyclopropylmethyl)amino][1,2,4]triazolo[4,3-a]pyridin-8-yl}spiro-[cyclopentane-1,3'-indol]-2'(1'H)-one
6'-(3-(Cyclopropylmethylamino)-7-methyl-[1,2,4]triazolo [4,3-a]pyridin-8-yl)spiro[cyclopentane-1,3'-indolin]-2'-one and pharmaceutically acceptable salts and N-oxides thereof.

Of outstanding interest are:
6'-(3-(Cyclopropylamino)-6-methylbenzo[d]isoxazol-7-yl) spiro[cyclopentane-1,3'-indolin]-2'-one
6-(3-(Cyclopropylamino)-6-methylbenzo[d]isoxazol-7-yl)-2',3',5',6'-tetrahydrospiro[indoline-3,4'-pyran]-2-one
6'-(3-(Cyclopropylamino)-6-methylbenzo[d]isoxazol-7-yl)-4,4-difluorospiro[cyclohexane-1,3'-indolin]-2'-one
6-(3-(Cyclopropylamino)-6-methylbenzo[d]isoxazol-7-yl)-3,3-dimethylindolin-2-one
6'-(3-(Cyclopropylamino)-6-methylbenzo[d]isoxazol-7-yl)-4-hydroxy-4-methylspiro[cyclohexane-1,3'-pyrrolo[3,2-b]pyridin]-2'(1'H)-one
6'-(3-(Cyclopropylamino)-6-methylbenzo[d]isoxazol-7-yl)-4-hydroxy-4-methylspiro[cyclohexane-1,3'-pyrrolo[3,2-b]pyridin]-2'(1'H)-one
6'-(3-Amino-6-methylbenzo[d]isoxazol-7-yl)-4-hydroxy-4-methylspiro[cyclohexane-1,3'-indolin]-2'-one
6'-(3-Amino-6-methylbenzo[d]isoxazol-7-yl)-4-(2-morpholinoethoxy)spiro[cyclohexane-1,3'-indolin]-2'-one
6'-(3-Amino-6-methyl-1,2-benzisoxazol-7-yl)-4,4-difluorospiro[cyclohexane-1,3'-indol]-2'(1H)-one According to a further feature of the present invention, compounds of general formula (I) may be prepared by synthetic routes as illustrated in FIG. 1.

Compounds of formula (I) may be obtained by coupling of a suitable halo derivative (IIA) wherein $R^1$, $R^2$, $G^2$ and $G^3$ are as defined above, and $Y^1$ is an halogen atom such as an iodine atom, with the corresponding boronate of formula (IIIA), $R^3$, $R^4$, $R^5$ and $G^1$ are as defined above, or boronic acid of formula (IIIB), using a Suzuki-type reaction (Miyaura, N.; Suzuki, A. Chem. Rev. 1995, 95, 2457). Such reactions may be catalyzed by a suitable palladium catalyst such as [1,1'-bis(diphenylphosphino)-ferrocene] dichloropalladium (II) complex with dichloromethane (1:1), in a solvent such as 1,4-dioxane, in the presence of a base such as aqueous cesium carbonate, at a temperature ranging from 80-120° C.

Alternatively, compounds of formula (I) may be prepared following the scheme depicted in FIG. 2, by reacting boronic acids of formula (IIB), wherein $R^1$, $R^2$, $G^2$ and $G^3$ are as defined above, with halo derivatives of formula (IIIC), wherein $R^3$, $R^4$, $R^5$ and $G^1$ are as defined above and $Y^2$ is an halogen atom such as a bromine atom, under Suzuki coupling conditions following the same synthetic procedure as described above.

Compounds of general formula (IIB) may be obtained via the synthetic pathway as depicted in FIG. 3.

Addition of a suitable organometallic reagent such as isopropylmagnesium chloride or bromide to a solution of (IIA), wherein $R^1$, $R^2$, $G^2$, $G^3$ and $Y^1$ are as defined above, in a suitable solvent such as tetrahydrofuran at temperatures ranging from −78° C. to room temperature followed by addition of a suitable alkyl borate such as triisopropyl borate and allowing the reaction to proceed at temperatures ranging from −78° C. to room temperature, gives, after work-up, boronic acids of general formula (IIB).

In the particular case where $G_2$ represents an aromatic carbon atom, compounds of formula (IIA') and (IIB'), are synthesized following the synthetic routes as depicted in FIG. 4.

Compounds of formula (V), wherein $R^2$ and $Y^1$ are as defined above, can be prepared by addition of a strong base such as lithium 2,2,6,6-tetramethylpiperidine to compounds of formula (IV) in a solvent such as tetrahydrofuran at a temperature ranging from −78 to −50° C. followed by addition of an electrophilic halogenating reagent such as molecular iodine and subsequently allowing the reaction to proceed at temperatures ranging from −78° C. to room temperature. Treatment of intermediates of type (V) with an acidic medium such as sulphuric acid in 1,4-dioxane at temperatures ranging from 50° C. to reflux temperature gives rise to intermediates of formula (VI) which may be transformed to compounds of formula (VII) by reaction with a suitable reducing agent such as borane-methylsulfide complex in a suitable solvent such as tetrahydrofuran at temperatures ranging from 0° C. to room temperature.

Aldehydes of formula (VIII) can be prepared by addition of a suitable oxidizing agent such as manganese (IV) oxide to compounds of formula (VII) in a suitable solvent such as dichloromethane or chloroform at temperatures ranging from room temperature to 50° C. Compounds of formula (VIII) may be transformed to compounds of formula (IX) by treatment with hydroxylamine hydrochloride in a suitable solvent such as ethanol at room temperature. Reaction of compounds of type (IX) with a suitable electrophilic chlorinating reagent such as N-chlorosuccinimide in a solvent such as N,N'-dimethylformamide at temperatures ranging from room temperature to 55° C. gives rises to compounds of formula (X) which may be subsequently reacted with amines of formula $R^1$—$NH_2$, wherein $R^1$ is as defined above, in a suitable solvent such as tetrahydrofuran or N,N'-dimethylformamide at room temperature to give intermediates of type (XI).

Derivatives of formula (IIA$^I$), wherein $G_3$ represents an oxygen atom, may be obtained by heating compounds of formula (XI) in a solvent such as tetrahydrofuran using a suitable base such as 2,3,4,6,7,8,9,10-octahydropyrimido[1,2-a]azepine or 1,8-diazabicyclo[5.4.0]undec-7-ene at temperatures ranging from 130-180° C. under microwave conditions.

In the particular case, wherein $G_3$ represents an oxygen atom and $R^1$ represents a hydrogen atom, compounds of formula (IIA$^I$), may be obtained from compounds of formula (V) by treatment with N-hydroxyacetamide in the presence of a suitable base such as potassium tert-butoxide in a solvent such as N,N'-dimethylformamide at room temperature.

Derivatives of formula (IIA$^I$), wherein $G_3$ represents a nitrogen atom, may be obtained by treatment of compounds of formula (V) with a hydrazine derivative in suitable solvent such as in ethanol at temperatures ranging from room temperature to 150° C.

Addition of a suitable organometallic reagent such as isopropylmagnesium chloride or bromide to a solution of (IIA$^I$) in a suitable solvent such as tetrahydrofuran at temperatures ranging from –78° C. to room temperature followed by addition of a suitable alkyl borate such as triisopropyl borate and allowing the reaction to proceed at temperatures ranging from –78° C. to room temperature, gives, after work-up, boronic acids of general formula (IIB$^I$).

In the particular case wherein both $G^2$ and $G^3$ are nitrogen atoms, compounds of formula (IIA$^{II}$), may be synthesized following the synthetic pathway as described in FIG. 5.

Compounds of formula (XIII), wherein $R^2$ and $Y^1$ are as defined above, may be obtained from compounds of formula (XII) following the experimental procedure as described in *J. Org. Chem.*, 1993, 58 (27), 7832-7838. Treatment of intermediates (XIII) with hydrazine hydrate in a solvent such as ethanol at temperatures ranging from room temperature to reflux gives rise to compounds of type (XIV). Reaction of compounds of formula (XIV) with a suitable reagent such triphosgene in a solvent such as dichloromethane at 0° C. followed by addition of an appropriate amine of formula $R^1$—$NH_2$, wherein $R^1$ is as defined above, in the presence of a suitable base such as triethylamine in a solvent such as dichloromethane at temperatures ranging from 0° C. to room temperature gives rise to compounds of formula (XV). Compounds of formula (IIA$^{II}$) are obtained by treatment of compounds of formula (XV) with a suitable dehydrating agent such as phosphorous oxychloride at temperatures ranging from room temperature to reflux.

Intermediates of formula (IIIA), (IIIC) and (IIIC$^I$) can be obtained following the synthetic pathways as depicted in FIG. 6.

Treatment of hydrazines of formula (XVI), wherein $G^1$, $R^3$ and $Y^2$ are as defined above, with a suitable acid chloride or acid anhydride in the presence of a base such as triethylamine in a solvent such as dichloromethane at a temperature ranging from –40° C. to room temperature gives intermediates of formula (XVII). Derivatives of formula (XVII) cyclise upon treatment with a suitable base such as calcium hydride or calcium (II) oxide either without solvent or with a suitable high-boiling inert solvent such as quinoline or tetralin at temperatures ranging from 200-280° C. to give compounds of type (IIIC).

Intermediates of formula (IIIC) may be transformed to the corresponding boronates of formula (IIIA) with a suitable reagent such as bis(pinacolato)diboron in the presence of a suitable base such as potassium acetate and a palladium catalyst such as [1,1'-bis(diphenylphosphino)ferrocene]dichloropalladium(II) complex with dichloromethane (1:1) in an aprotic organic solvent such as N,N'-dimethylformamide or dimethylsulphoxide at a temperature ranging from 80 to 120° C.

Intermediates of formula (IIIC) may be also be transformed to the corresponding derivatives of formula (IIIC$^I$), by treatment of (IIIC) with a suitable electrophilic halogenating agent such as N-chlorosuccinimide in a solvent such as chloroform at reflux temperature.

Intermediate compounds of type (IIIC$^I$) may also be prepared by following the synthetic route as depicted in FIG. 7.

Intermediates (IIIC$^I$) may be obtained by reaction of the compounds of formula (XVIII) with a suitable base such as butyl lithium, lithium bis(trimethylsilyl)amide, cesium carbonate or sodium bis(trimethylsilyl)amide possibly in the presence of a additive such as N,N,N',N'-tetramethylethylenediamine in a solvent such as tetrahydrofuran or N,N'-dimethylformamide at a temperature ranging from –78° C. to room temperature followed by addition of a corresponding dihalo derivative and then allowing the reaction to proceed at temperatures ranging from –78° C. to room temperature. Alternatively, compounds of formula (XVIII) may be converted first to an intermediate of formula (XIX) where P1 represents a suitable protecting group such as tert-butoxycarbonyl (BOC). Treatment of compounds of formula (XIX) with a dihaloderivative following the conditions as described above followed by subsequent deprotection with a suitable reagent furnishes compounds of formula (IIIC$^I$).

In the particular case wherein the spiroalkyl group represents a 4-substituted cyclohexyl moiety, compounds of formula (IIIC$^{II}$ to IIIC$^{VI}$) may be synthesized following the synthetic routes depicted in FIG. 8.

Compounds of formula (XVIII), wherein $G^1$, $R^3$ and $Y^2$ are as defined above, may be treated with methyl acrylate in the presence of a suitable base such as potassium tert-butoxide in a solvent such as dimethylsulfoxide to give, after hydrolysis with water, cyclohexanone derivatives of formula (IIIC$^{II}$). These derivatives may be transformed into the difluoro compounds of formula (IIIC$^{III}$) by treatment with a suitable reagent such as (diethylamino) sulfur trifluoride in a solvent such as dichloromethane at room temperature.

In another synthetic pathway, compounds of formula (IIIC$^{II}$) may be treated with an organometallic reagent such as methyl lithium in a solvent such as tetrahydrofuran at temperatures ranging from –78° C. to reflux to furnish alcohols of formula (IIIC$^{IV}$).

Finally, compounds of formula (IIIC$^{II}$) may be transformed to intermediates of type (IIIC$^V$) by treatment of compounds of formula (IIIC$^{II}$) with 2-chloroethanol in the presence of an acid such as methanesulphonic acid in a solvent such as dichloromethane/toluene at ambient temperature followed by treatment of the intermediate compound with a reducing agent such as zinc borohydride in the presence of trimethylsilyl chloride in a solvent such as dichloromethane or diethyl ether to give compounds of formula (IIIC$^V$). Compounds of formula (IIIC$^V$) may be converted to compounds of formula (IIIC$^{VI}$) by treatment of (IIIC$^V$) with an amine ($R_4R_5NH$) such as morpholine in the presence of an activating agent such as sodium iodide in a solvent such as N,N'-dimethylformamide at temperatures ranging from ambient temperature to reflux.

Intermediate compounds of formula (XVIII) may be prepared by following the synthetic route as depicted in FIG. 9.

Nitroderivatives of formula (XX), wherein $G^1$, $R^3$ and $Y^2$ are as defined above and $Y^4$ represents a halogen atom such as chlorine or fluorine atom, react with alkyl malonate salts, prepared by the addition of the corresponding alkyl malonate to a mixture of a suitable base such as sodium hydride in an appropriate solvent such as 1,2-dimethoxyethane or N,N'-dimethylformamide at a temperature ranging from 10 to 80° C., to give the corresponding intermediates of formula (XXI). Treatment of derivatives of formula (XXI) with an inorganic mineral acid such as aqueous hydrochloric acid in a suitable solvent such as dimethylsulphoxide at temperatures ranging from 20-130° C., gives carboxylic acid derivatives of formula (XXII). Derivatives of both formula (XXI) and (XXII) may be converted into oxindole derivatives of formula (XVIII) by treatment with a suitable reducing agent such as iron powder in a solvent such as ethanol/aqueous hydrochloric acid or acetic acid at temperatures ranging from 80-150° C.

Biological Testing
Inhibition Assay

Enzymatic activity assay was performed in 96-well microtiter plates (Corning, catalog number #3686) using a total volume of 50 μl of an assay buffer composed of 50 mM HEPES pH 7.5, 10 mM $MgCl_2$, 1.75 mM $Na_3VO_4$.

Various concentrations of the test compound or vehicle controls were pre-incubated for one hour with 0.055 μg/ml of the human p38alfa (SAPKa) enzyme (obtained from University of Dundee). The reaction was started by addition of biotinylated ATF2 substrate and ATP in concentrations around their Km values (final concentration 0.62 μM and 60 μM respectively) and took place for one hour at 25° C. Addition of the detection reagents, streptavidin-XL665 and anti-phosphoresidue antibody coupled to Europium cryptate, caused the juxtaposition of the cryptate and the XL665 fluorophore, resulting in fluorescence energy transfer (FRET). The FRET intensity depends on the amount of bounded cryptate antibody, which is proportional to the extent of substrate phosphorylation. FRET intensity was measured using Victor 2V spectrofluorometer.

Data were analyzed by non-linear regression (Hill equation) to generate a dose-response curve. The calculated $IC_{50}$ value is the concentration of the test compound that caused a 50% decrease in the maximal FRET intensity.

Table 1 shows the results obtained from the above-mentioned assay with a selection of compounds from the present invention.

TABLE 1

| Example | p38α $IC_{50}$ (nM) |
|---|---|
| 1 | 0.9 |
| 2 | 39 |
| 3 | 4 |
| 4 | 0.2 |
| 5 | 0.06 |
| 6 | 0.4 |
| 7 | 6.3 |
| 8 | 0.65 |
| 9 | 0.4 |
| 11 | 10 |
| 12 | 0.9 |
| 13 | 3.3 |
| 14 | 1 |
| 15 | 38 |
| 20 | 20 |

It can be seen from Table 1 that the compounds of formula (I) are potent inhibitors of the p38 mitogen-activated protein kinase. Preferred substituted indolin-2-one derivatives of the invention possess a $IC_{50}$ value of inhibition of p38α of less than 100 nM, more preferably less than 80 nM and most preferably less than 50 nM.

Functional Assay

The activity of compounds in inhibiting TNFα production was measured in a cellular assay using the human monocytic cell line THP-1. For this purpose, $2\times10^5$ cells/well were plated in tissue-culture treated round-bottom 96-well plates in RPMI (containing 10% FCS, L-Gln 2 mM, Hepes buffer 10 mM, sodium pyruvate 1 mM, glucose 4.5 gr/L, $HNaCO_3$ 1.5 g/L and beta-mercaptoethanol 50 μM), together with compounds at the desired test concentration and LPS (Sigma, L2630) at a final 10 μg/ml concentration. Compounds were resuspended in 100% DMSO at a concentration of 1 mM and titrated thereof in 10× dilutions in medium. Controls included stimulated cells alone and stimulated cells treated with the highest concentration of compound vehicle (1% DMSO). Cells were incubated for 5 h at 37° C. in a 5% $CO_2$ atmosphere. Cell supernatant was recovered by centrifugation and diluted 5-fold prior to testing in a standard human TNFα ELISA (RnD systems).

Data were analyzed by non-linear regression (Hill equation) to generate a dose-response curve. The calculated $IC_{50}$ value is the concentration of the test compound that caused a 50% decrease in the maximal TNFα production.

Compounds of the present invention are good inhibitors of TNFα production. Preferred derivatives of the invention possess an $IC_{50}$ value for inhibiting TNFα production of less than 100 μM, preferably less than 10 μM, more preferably less than 1 μM and most preferably less than 100 nM.

The substituted indolin-2-one derivatives of the invention are useful in the treatment or prevention of diseases known to be susceptible to improvement by inhibition of the p38 mitogen-activated protein kinase. Such diseases are, for example rheumatoid arthritis, ischemia-reperfusion injury, cerebral focal ischemia, acute coronary syndrome, asthma, COPD, Crohn's disease, irritable bowel syndrome, adult respiratory distress syndrome, osteoporosis, Alzheimer's disease, rheumatoid spondylitis, psoriasis, atherosclerosis, osteoarthritis or multiple myeloma.

Accordingly, the substituted indolin-2-one derivatives of the invention and pharmaceutically acceptable salts thereof, and pharmaceutical compositions comprising of such compound and/or salts thereof, may be used in a method of treatment of disorders of the human body which comprises administering to a subject requiring such treatment an effective amount of substituted indolin-2-one derivatives of the invention or a pharmaceutically acceptable salt thereof.

When the substituted indolin-2-one derivatives of the invention are used for the treatment of respiratory diseases such as asthma, chronic obstructive pulmonary disorder, pulmonary fibrosis or emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) cortiocosteroids, (5) leukotriene D4 antagonists, (6) inhibitors of egfr-kinase, (7) antagonists of the $A_{2B}$ adenosine receptor, (8) NK1 receptor agonists, (9) CRTh2 antagonists, (10) syk kinase inhibitors, (11) CCR3 antagonists and (12) VLA-4 antagonists.

The present invention also provides pharmaceutical compositions comprising a substituted indolin-2-one derivative of the invention and another active compound selected from the groups consisting of (1) antagonists of M3 muscarinic receptors, (2) β2-agonists, (3) PDE 4 inhibitors, (4) cortiocosteroids, (5) leukotriene D4 antagonists, (6) inhibitors of egfr-kinase, (7) antagonists of the $A_{2B}$ adenosine receptor, (8) NK1 receptor agonists, (9) CRTh2 antagonists, (10) syk kinase inhibitors, (11) CCR3 antagonists, (12) VLA-4 antagonists and (13) disease modifying antirheumatic drugs (DMARDs) such as methotrexate.

When substituted indolin-2-one derivatives of the invention are used for the treatment of respiratory diseases such as asthma, chronic obstructive pulmonary disorder, pulmonary fibrosis and emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) cortiocosteroids, (5) CysLT1 and/or CysLT2 antagonists, (6) inhibitors of egfr-kinase, (7) A2b antagonists, (8) NK1 receptor agonists, (9) CRTh2 antagonists, (10) syk kinase inhibitors, (11) CCR3 antagonists and (12) VLA-4 antagonists.

When substituted indolin-2-one derivatives of the invention are used for the treatment of autoimmune diseases such as psoriasis, rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease it may be advantageous to use them in combination with other active compounds known to be useful in the treatment of autoimmune diseases such as PDE4 inhibitors, CysLT1 and/or CysLT2 antagonists, inhibitors of egfr-kinase, A2b antagonists, NK1 receptor agonists, CCR3 antagonists, VLA-4 antagonists and disease modifying antirheumatic drugs (DMARDs).

Examples of suitable M3 antagonists (anticholinergics) that can be combined with the inhibitors of the p38 mitogen-activated protein kinase of the present invention are tiotropium salts, oxitropium salts, flutropium salts, ipratropium salts, glycopyrronium salts, trospium salts, revatropate, espatropate, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo [2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3, 3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N-[N-[2-[N-[1-(Cyclohexylmethyl)piperidin-3(R)-ylmethyl] carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts, chlorides, bromides, iodides and methanesulphonates are preferred.

Examples of suitable β2-agonists that can be combined with the inhibitors of the p38 mitogen-activated protein kinase of the present invention are: arformoterol, bambuterol, bitolterol, broxaterol, carbuterol, clenbuterol, dopexamine, fenoterol, formoterol, hexoprenaline, ibuterol, isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, milveterol, GSK-678007, GSK-642444, GSK-159802, LAS100977, HOKU-81, KUL-1248, carmoterol, indacaterol and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl] sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol and 1-(4-ethoxycarbonylamino-3-cyano-5-fluorophenyl)-2-(tert-butylamino)ethanol optionally in the form of their racemates, their enantiomers, their diastereomers, and mixtures thereof, and optionally their pharmacologically-compatible acid addition salts and the compounds claimed in International Patent application numbers WO2006/122788A1 and WO2007/124898. When the β2-agonists are in the form of a salt or derivative it is particularly preferred that it is in a form selected from the sodium salts, sulfobenzoates, phosphates, isonicotinates, acetates, propionates, dihydrogen phosphates, palmitates, pivalates, fumarates, furoates, xinafoates or mixtures thereof.

The following β2-agonists are of special interest for the combination with the compounds of formula (I): arformoterol, bambuterol, bitolterol, broxaterol, carbuterol, clenbuterol, dopexamine, fenoterol, formoterol, hexoprenaline, ibuterol, isoprenaline, levosalbutamol, mabuterol, meluadrine, nolomirole, orciprenaline, pirbuterol, procaterol, (R,R)-formoterol, reproterol, ritodrine, rimoterol, salbutamol, salmeterol, sibenadet, sulfonterol, terbutaline, tulobuterol, GSK-597901, milveterol, LAS100977, KUL-1248, carmoterol and indacaterol optionally in the form of their racemates, their enantiomers, their diastereomers, and mixtures thereof, and optionally their pharmacologically-compatible acid addition salts Still most preferred are the following β2-agonists: formoterol, salmeterol and GSK-597901, GSK-159797, indacaterol optionally in the form of their racemates, their enantiomers, their diastereomers and mixtures thereof, and optionally their pharmacologically-compatible acid addition salts. Still more preferred are salmeterol and formoterol.

Examples of suitable PDE4 inhibitors that can be combined with the inhibitors of the p38 mitogen-activated protein kinase of the present invention are denbufylline, rolipram, cipamfylline, arofylline, filaminast, piclamilast, mesopram, drotaverine hydrochloride, lirimilast, cilomilast, oglemilast, apremilast, 6-[2-(3,4-Diethoxyphenyl)thiazol-4-yl]pyridine-2-carboxylic acid (tetomilast), (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluororomethoxyphenyl)cyclohexan1-one, cis[4-cyano-4-(3-cyclopropylmethoxy-4-difluoromethoxyphenyl)cyclohexan-1-ol, ONO-6126 (Eur Respir J 2003, 22(Suppl. 45): Abst 2557) and the compounds claimed in the PCT patent applications number WO03/097613, WO2004/058729, WO 2005/049581, WO 2005/123693 and WO 2005/123692

Examples of suitable corticosteroids and glucocorticoids that can be combined with β2-agonists are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, butixocort propionate, RPR-106541, halometasone, methylprednisolone suleptanate, mometasone furoate, rimexolone, prednisolone farnesylate, ciclesonide, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable CysLT1 and/or CysLT2 antagonists that can be combined with the inhibitors of the p38 mitogen-activated protein kinase of the present invention are montelukast, Ibudilast, pobilukast, pranlukast hydrate, zafirlukast, ritolukast, verlukast, sulukast, tipelukast, cinalukast, iralukast sodium, masilukast, montelukast sodium, 5-[3-[3-(2-Quinolinylmethoxy)phenoxy]propyl]-1H-tetrazole, (E)-8-[2-[4-[4-(4-Fluorophenyl)butoxy]phenyl]vinyl]-2-(1H-tetrazol-5-yl)-4H-benzopyran-4-one sodium salt, 2-[N-[4-(4-Chlorophenylsulfonamido)butyl]-N-[3-(4-isopropylthiazol-2-ylmethoxy)benzyl]sulfamoyl]benzoic acid, (3R,4R)-3-[6-(5-Fluorobenzothiazol-2-ylmethoxy)-4-hydroxy-3,4-dihydro-2H-1-benzopyran-3-ylmethyl]benzoic acid, 2-[2-[2-(4-tert-Butylthiazol-2-yl)benzofuran-5-yloxymethyl]phenyl]acetic acid hydrochloride, 5-[2-[4-(Quinolin-2-ylmethoxy)phenoxymethyl]benzyl]-1H-tetrazole, (E)-2,2-Diethyl-3'-[2-[2-(4-isopropyl)thiazolyl]ethenyl]succinanilic acid; 4-[4-[3-(4-Acetyl-3-hydroxy-2-propylphenoxy)propylsulfonyl]phenyl]-4-oxobutyric acid, [[5-[[3-(4-Acetyl-3-hydroxy-2-propylphenoxy)propyl]thio]-1,3,4-thiadiazol-2-yl]thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl]phenyl]-8-(N,N-dimethylcarbamoyl)-4,6-dithiaoctanoic acid sodium salt; 3-[1-[3-[2-(7-Chloroquinolin-2-yl)vinyl]phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d]pyrimidin-9(1H)-one, (R)-3-[2-Methoxy-4-[N-(2-methylphenylsulfonyl)carbamoyl]benzyl]-1-methyl-N-(4,4,4-trifluoro-2-methylbutyl)indole-5-carboxamide, MCC-847 (from AstraZeneca), (+)-4(S)-(4-Carboxyphenylthio)-7-[4-(4-phenoxybutoxy)phenyl]-5(Z)-heptenoic acid and the compounds claimed in PCT patent application WO2004/043966A1.

Examples of suitable inhibitors of egfr-kinase that can be combined with the inhibitors of the p38 mitogen-activated protein kinase of the present invention are palifermin, cetuximab, gefitinib, repifermin, erlotinib hydrochloride, canertinib dihydrochloride, lapatinib, and N-[4-(3-Chloro-4-fluorophenylamino)-3-cyano-7-ethoxyquinolin-6-yl]-4-(dimethylamino)-2(E)-butenamide.

Examples of suitable antagonists of the A2b adenosine receptor that can be combined with the inhibitors of the p38 mitogen-activated protein kinase of the present invention are CVT-6883 from CV Therapeutics, 4-(1-butylxanthin-8-yl)benzoic acid, 8-[1-[3-(4-chlorophenyl)-1,2,4-oxadiazol-5-ylmethyl]-1H-pyrazol-4-yl]-1,3-dipropylxanthine, N-(1,3-benzodioxol-5-yl)-2-[5-(1,3-dipropylxanthin-8-yl)-1-methyl-1H-pyrazol-3-yloxy]acetamide, 8-[4-[5-(2-methoxyphenyl)-1,2,4-oxadiazol-3-ylmethoxy]phenyl]-1,3-dipropylxanthine, 3-[5-(2-methyl-1H-imidazol-1-yl)-2-(pyrazin-2-ylamino)thiazol-4-yl]benzonitrile, 4-(2,6-dioxo-1-propyl-2,3,6,7-tetrahydro-1H-purin-8-yl)benzenesulfonic acid, 1-[2-[8-(3-fluorophenyl)-9-methyl-9H-adenin-2-yl]ethynyl]cyclopentanol hydrochloride, N-(2-acetylphenyl)-2-[4-(1,3-dipropylxanthin-8-yl)phenoxy]acetamide, N-(4-acetylphenyl)-2-[4-(1,3-dipropylxanthin-8-yl)phenoxy]acetamide, N-(4-cyanophenyl)-2-[4-(1,3-dipropylxanthin-8-yl)phenoxy]acetamide, 4-(3,4-dichlorophenyl)-5-(4-pyridinyl)thiazol-2-amine or the compounds of international patent applications WO 2005/040155 A1, WO2005/100353 A1 WO 2007/039297A1 and WO2007/017096 A1.

Examples of suitable NK1-receptor antagonists that can be combined with the inhibitors of the p38 mitogen-activated protein kinase of the present invention are nolpitantium besilate, dapitant, lanepitant, vofopitant hydrochloride, aprepitant, ezlopitant, N-[3-(2-Pentylphenyl)propionyl]-threonyl-N-methyl-2,3-dehydrotyrosyl-leucyl-D-phenylalanyl-allothreonyl-asparaginyl-serine C-1.7-O-3.1 lactone, 1-Methylindol-3-ylcarbonyl-[4(R)-hydroxy]-L-prolyl-[3-(2-naphthyl)]-L-alanine N-benzyl-N-methylamide, (+)-(2S,3S)-3-[2-Methoxy-5-(trifluoromethoxy)benzylamino]-2-phenylpiperidine, (2R,4S)-N-[1-[3,5-Bis(trifluoromethyl)benzoyl]-2-(4-chlorobenzyl)piperidin-4-yl]quinoline-4-carboxamide, 3-[2(R)-[1(R)-[3,5-Bis(trifluoromethyl)phenyl]ethoxy]-3(S)-(4-fluorophenyl)morpholin-4-ylmethyl]-5-oxo-4,5-dihydro-1H-1,2,4-triazole-1-phosphinic acid bis(N-methyl-D-glucamine) salt; [3-[2(R)-[1(R)-[3,5-bis(trifluoromethyl)phenyl]ethoxy]-3(S)-(4-fluorophenyl)-4-morpholinylmethyl]-2,5-dihydro-5-oxo-1H-1,2,4-triazol-1-yl]phosphonic acid 1-deoxy-1-(methylamino)-D-glucitol (1:2) salt, 1'-[2-[2(R)-(3,4-Dichlorophenyl)-4-(3,4,5-trimethoxybenzoyl)morpholin-2-yl]ethyl]spiro[benzo[c]thiophen-1(3H)-4'-piperidine]2(S)-oxide hydrochloride and the compound CS-003 described in Eur Respir J 2003, 22(Suppl. 45): Abst P2664.

Examples of suitable CRTh2 antagonists that can be combined with the inhibitors of the p38 mitogen-activated protein kinase of the present invention are 2-[5-Fluoro-2-methyl-1-[4-(methylsulfonyl)phenylsulfonyl]-1H-indol-3-yl]acetic acid, Ramatroban, [(3R)-4-(4-chlorobenzyl)-7-fluoro-5-

(methylsulfonyl)-1,2,3,4tetrahydrocyclopenta[b]indol-3-yl] acetic acid and (1R,2R,3S,5S)-7-[2-(5-Hydroxybenzothiophen-3-ylcarboxamido)-6,6-dimethylbicyclo[3.1.1] hept-3-yl]-5(Z)-heptenoic acid.

Examples of suitable Syk kinase inhibitors that can be combined with the inhibitors of the p38 mitogen-activated protein kinase of the present invention are piceatannol, 2-(2-Aminoethylamino)-4-[3-(trifluoromethyl)phenylamino]pyrimidine-5-carboxamide, R-091 (from Rigel), R-112 (from Rigel), R-343 (from Rigel), R-788 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate, 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide, 2-[7-(3,4-Dimethoxyphenyl)imidazo[1,2-c]pyrimidin-5-ylamino] pyridine-3-carboxamide dihydrochloride and AVE-0950 (from Sanofi-Aventis).

Examples of CCR3 antagonists that can be combined with the inhibitors of the p38 mitogen-activated protein kinase of the present invention are 4-[3-[4-(3,4-Dichlorobenzyl)morpholin-2(S)-ylmethyl]ureidomethyl]benzamide, N-[1(R)-[4-(3,4-Dichlorobenzyl)piperidin-1-ylmethyl]-2-methylpropyl]-N'-(3,4,5-trimethoxyphenyl)urea, N-[1(S)-[4-(4-Chlorobenzyl)piperidin-1-ylmethyl]-2-hydroxypropyl]-N'-(3,4,5-trimethoxyphenyl)urea, 3-[3-(3-Acetylphenyl) ureido]-2-[4-(4-fluorobenzyl)piperidin-1-ylmethyl]-N-methylbenzamide, 4-(3,4-Dichlorobenzyl)-1-methyl-1-[3-methyl-2(R)-[3-(3,4,5-trimethoxyphenyl)ureido]butyl] piperidinium chloride, N-[2-[4(R)-(3,4-Dichlorobenzyl) pyrrolidin-2(S)-yl]ethyl]-2-[5-(3,4-dimethoxyphenyl) pyrimidin-2-ylsulfanyl]acetamide, CRIC-3 (from IPF Pharmaceuticals), 2(R)-[1-[1-(2,4-Dichlorobenzyl)-4(S)-(3-thienyl)pyrrolidin-3(S)-ylmethyl]piperidin-4-ylmethyl]pentanoic acid, 8-[1-(2,4-Dichlorobenzyl)-4(S)-(3-thienyl)pyrrolidin-3(S)-ylmethyl]-3,3-dipropyl-1-oxa-8-azaspiro[4.5] decane-2(S)-carboxylic acid, 11-[1-(2,4-Dichlorobenzyl)-4 (S)-(3-thienyl)pyrrolidin-3(S)-ylmethyl]-3,14-dioxa-11-azadispiro[5.1.5.2]pentadecane-15(S)-carboxylic acid, W-56750 (from Mitsubishi Pharma), N-[1(S)-[3endo-(4-Chlorobenzyl)-8-azabicyclo[3.2.1]oct-8-ylmethyl]-2(S)-hydroxypropyl]-N'-(3,4,5-trimethoxyphenyl)urea, N-(3-Acetylphenyl)-N'-[(1R,2S)-2-[3(S)-(4-fluorobenzyl) piperidin-1-ylmethyl]cyclohexyl]urea benzenesulfonate, trans-1-(Cycloheptylmethyl)-4-(2,7-dichloro-9H-xanthen-9-ylcarboxamido)-1-methylpiperidinium iodide, GW-782415 (from GlaxoSmithKline), GW-824575 (from GlaxoSmithKline), N-[1'-(3,4-Dichlorobenzyl)-1,4'-bipiperidin-3-ylmethyl]quinoline-6-carboxamide, N-[1-(6-Fluoronaphthalen-2-ylmethyl)pyrrolidin-3(R)-yl]-2-[1-(3-hydroxy-5-methylpyridin-2-ylcarbonyl)piperidin-4-ylidene] acetamide fumarate and DIN-106935 (from Bristol-Myers Squibb).

Examples of VLA-4 antagonists that can be combined with the inhibitors of the p38 mitogen-activated protein kinase of the present invention are N-[4-[3-(2-Methylphenyl)ureido] phenylacetyl]-L-leucyl-L-aspartyl-L-valyl-L-proline, 3(S)-[2(S)-[4,4-Dimethyl-3-[4-[3-(2-methylphenyl)ureido]benzyl]-2,5-dioxoimidazolidin-1-yl]-4-methylpentanoylamino]-3-phenylpropionic acid, 2(S)-(2,6-Dichlorobenzamido)-3-(2',6'-dimethoxybiphenyl-4-yl) propionic acid, RBx-4638 (from Ranbaxy), R-411 (from Roche), RBx-7796 (from Ranbaxy), SB-683699 (from GlaxoSmithKline), DW-908e (from Daiichi Pharmaceutical), RO-0270608 (from Roche), AJM-300 (from Ajinomoto), PS-460644 (from Pharmacopeia) and the compounds claimed in PCT patent application numbers WO 02/057242 A2 and WO 2004/099126 A1.

Examples of disease modifying antirheumatic drugs (DMARs) that can be combined with the inhibitors of the p38 mitogen-activated protein kinase of the present invention are auranofin, azathioprine, bucillamine, cyclosporine, iguratimod, leflunomide, methotrexate, pentostatin, rimacalib hydrochloride, romazarit, salazodine, sulphasalazine, teriflunomide, (E)-5-(3,5-Di-tert-butyl-4-hydroxybenzylidene)-2-ethylisothiazolidine 1,1-dioxide, cis-2-(4-Chlorophenyl)-4,5-diphenyl-4,5-dihydro-1H-imidazole hydrochloride, 2-[8-[2-[6-(Methylamino)pyridyl-2-ylethoxy]-3-oxo-2-(2,2,2-trifluoroethyl)-2,3,4,5-tetrahydro-1H-2-benzazepin-4-(S)-yl]acetic acid, 4-acetoxy-2-(4-methylphenyl)benzothiazole, 3-[4-Methyl-3-[N-methyl-N-(7H-pyrrolo[2,3-d]pyrimidin-4-yl)amino]piperidin-1-yl]-3-oxopropionitrile (CP-690550), 3-Deazaadenosine, 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406), AD-452 from Sosei, AD-827 from Arakis, BB-2983 from British Biotech, SC-12267 from 4SC, CPH-82 from Conpharm, R-1295 from Roche, R-1503 from Roche and N2-[3-[1(S)-(2-Fluorobiphenyl-4-yl)ethyl]isoxazol-5-yl] morpholine-4-carboxamidine hydrochloride (SMP-114).

The combinations of the invention may be used in the treatment of disorders which are susceptible to amelioration by inhibition of the p38 mitogen-activated protein kinase. Thus, the present application encompasses methods of treatment of these disorders, as well as the use of the combinations of the invention in the manufacture of a medicament for the treatment of these disorders, especially for the treatment of rheumatoid arthritis.

The present invention also provides pharmaceutical compositions which comprise, as an active ingredient a substituted indolin-2-one derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, inhaled, nasal, rectal, percutaneous or injectable administration. Compositions for oral administration may be in the form of syrups, tablets, capsules, lozenges, controlled-release preparations, fast-dissolving preparations, etc. Compositions for topical administration may be in the form of creams, ointments, lotions, nasal sprays or aerosols, etc). Compositions for administration by injection may be in the form of subcutaneous, intradermic, intramuscular or intravenous compositions. Compositions for administration by inhalation may be in the form of a dry powder, a solution, a dispersion, etc.

The active compounds in the combination, i.e. the inhibitors of the p38 mitogen-activated protein kinase of the invention, and the other optional active compounds may be administered together in the same pharmaceutical composition or in different compositions intended for separate, simultaneous, concomitant or sequential administration by the same or a different route.

One execution of the present invention consists of a kit of parts comprising of inhibitors of the p38 mitogen-activated protein kinase of the present invention together with instructions for simultaneous, concurrent, separate or sequential use in combination with another active compound useful in the treatment of a respiratory disease which responds to inhibition of the p38 mitogen-activated protein kinase.

Another execution of the present invention consists of a package comprising of inhibitors of the p38 mitogen-activated protein kinase of formula (I) and another active compound useful in the treatment of a respiratory disease for the simultaneous, concurrent, separate or sequential use in the treatment of a respiratory disease which responds to the inhibition of the p38 mitogen-activated protein kinase.

The pharmaceutically acceptable excipients which are admixed with the active compound or salts of such compound, to form the compositions of this invention are well-known per se and the actual excipients used depend inter alia on the intended method of administering the compositions.

The diluents which may be used in the preparation of the compositions include those liquid and solid diluents which are compatible with the active ingredient, together with colouring or flavouring agents, if desired. Tablets or capsules may conveniently contain between 1 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For single dose inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients. Other drawbacks related to the use of hard gelatine capsules for inhalation powders are (a) poor protection against moisture uptake from the ambient air; (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported.

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described in the following patent applications Nos.: WO97/000703, WO03/000325 and WO03/061742.

Apart from applications through dry powder inhalers the compositions of the invention can also be administered in aerosols which operate via propellant gases or by means of so-called atomisers, via which solutions of pharmacologically-active substances can be sprayed under high pressure so that a mist of inhalable particles results. Such atomisers are described, for example, in WO 91/14468 and WO 97/12687.

Effective doses are normally in the range of 1-2000 mg of active ingredient per day. Daily dosage may be administered in one or more treatments, preferably from 1 to 4 treatments, per day.

The syntheses of the compounds of the invention and of the intermediates for use therein are illustrated by the following examples (1-20) including preparation examples (intermediates 1-28) which do not limit the scope of the invention in any way.

$^1$H Nuclear Magnetic Resonance Spectra were recorded on a Varian Gemini 300 spectrometer. Melting points were recorded using a Büchi B-540 apparatus. The LCMS chromatographic separations were obtained using a Waters 2795 system equipped with a Symmetry C18 (2.1×100 mm, 3.5 mm) column. As detectors a Micromass ZMD mass spectrometer using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time

PREPARATION 1

6-Bromoindolin-2-one

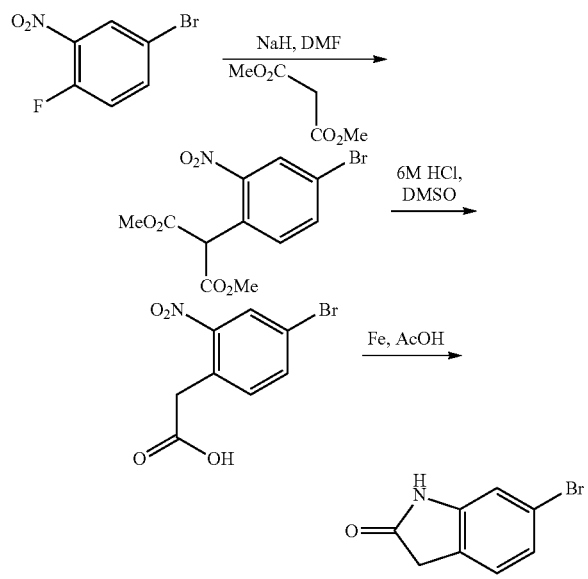

a) Dimethyl 2-(4-bromo-2-nitrophenyl)malonate

Dimethyl malonate (40.34 g, 0.305 mol) in N,N'-dimethylformamide (45 mL) was added dropwise to a stirred suspension of sodium hydride (60% dispersion in mineral oil, 16.2 g, 405 mmol) in N,N'-dimethylformamide (500 mL) at 10° C. The mixture was stirred for 1 hour at room temperature then 4-bromo-1-fluoro-2-nitrobenzene (44.38 g, 202 mmol) in N,N'-dimethylformamide (45 mL) was added dropwise to the reaction mixture. The mixture was stirred 75 minutes at room temperature and then was warmed to 65° C. After 1 hour, the solvent was removed under reduced pressure, the residue was taken up in a mixture of ethyl acetate and water and 2M aqueous hydrochloric acid was added until the mixture became pale yellow in colour. The organic layer was separated, washed with water, brine, dried (MgSO$_4$) and evaporated. The crude product was recrystallized from diisopropyl ether to give the title compound (55.0 g, 83%) as a pale yellow solid.

LRMS (m/z): 330/332 (M−1)⁻.

$^1$H-NMR δ (CDCl$_3$): 3.81 (s, 6H), 5.28 (s, 1H), 7.43 (d, J=9.0 Hz, 1H), 7.78 (dd, J=9.0 and 3.0 Hz, 1H), 8.21 (d, J=4.0 Hz, 1H).

b) 2-(4-Bromo-2-nitrophenyl)acetic acid

6M Aqueous hydrochloric acid (200 mL) was added to a stirred solution of dimethyl 2-(4-bromo-2-nitrophenyl)malonate (preparation 1a, 55.45 g, 170 mmol) in dimethylsulphoxide (250 mL) at room temperature and then mixture was warmed to 130° C. with stirring. After 5 hours, the mixture was cooled and water (400 mL) was added with stirring and the mixture was left to cool overnight. The precipitate was filtered, washed with water and dried in vacuo to give the title compound (41.0 g, 94%) as a white solid.

LRMS (m/z): 258/260 (M−1)⁻.

$^1$H-NMR δ (DMSO-d$_6$): 3.98 (s, 2H), 7.53 (d, J=9.0 Hz, 1H), 7.95 (d, J=9.0 Hz, 1H), 8.27 (s, 1H), 12.66 (s, 1H).

c) 6-Bromoindolin-2-one

Iron (40.0 g, 700 mmol) was added slowly to a stirred solution of 2-(4-bromo-2-nitrophenyl)acetic acid (preparation 1b, 46.6 g, 200 mmol) in acetic acid (390 mL) at 75° C., and then mixture was stirred for 1 hour at 100° C. Then the mixture was cooled and ethyl acetate was added. The mixture was filtered through Celite® and the solvent evaporated. The crude product was washed with 0.1M aqueous hydrochloric acid, water, diethyl ether and dried to give the title compound (22.0 g, 58%) as a solid.

LRMS (m/z): 212/214 (M+1)⁺.

$^1$H-NMR δ (DMSO-d$_6$): 3.45 (s, 2H), 6.94 (s, 1H), 7.09-7.17 (m, 2H), 10.50 (s, 1H).

PREPARATION 2

6'-Bromospiro[cyclopentane-1,3'-indolin]-2'-one

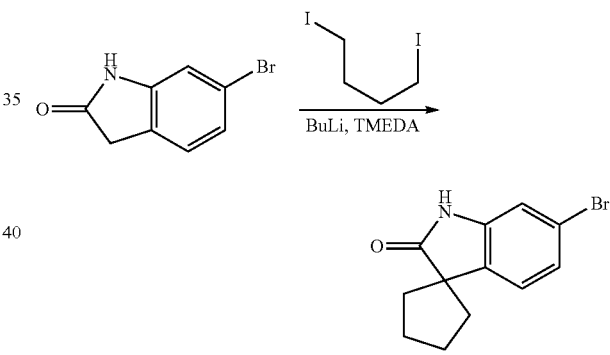

n-Butyl lithium (2.5 M in hexanes, 3.8 mL, 9.5 mmol) was added dropwise over 30 minutes to a stirred suspension of 6-bromoindolin-2-one (preparation 1, 1.00 g, 4.7 mmol) and N,N,N',N'-tetramethylethylenediamine (1.42 mL, 9.4 mmol) in tetrahydrofuran (20 mL) at −78° C. The mixture was stirred for 1 hour, then 1,4-diiodobutane (3.11 mL, 23.6 mmol) was added dropwise over 5 minutes. The mixture was warmed to −20° C. over a 1 hour period, was stirred for a further hour at this temperature and was then warmed to room temperature. After 3 hours stirring at room temperature, saturated aqueous ammonium chloride solution was added to the reaction and the mixture was extracted with ethyl acetate. The organic layer was washed with water, brine, dried (MgSO$_4$) and evaporated. Purification of the residue by flash chromatography (10:1 hexanes/ethyl acetate) gave the title compound (0.57 g, 45%) as a pale pink solid.

LRMS (m/z): 266/268 (M+1)⁺.

$^1$H-NMR δ (CDCl$_3$): 1.81-2.20 (m, 8H), 7.02-7.06 (m, 2H), 7.14-7.18 (m, 1H), 7.83 (br s, 1H).

PREPARATION 3

6'-Bromo-5'-chlorospiro[cyclopentane-1,3'-indolin]-2'-one

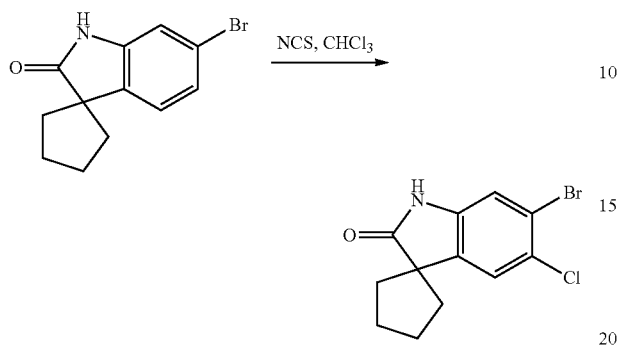

N-Chlorosuccinimide (500 mg, 3.75 mmol) was added to a solution of 6'-bromospiro[cyclopentane-1,3'-indolin]-2'-one (preparation 2, 0.20 g, 0.75 mmol) in chloroform (5 mL). The mixture was stirred and heated to reflux. After 6 hours, the mixture was cooled to room temperature. Saturated aqueous sodium hydrogen carbonate solution was added to the reaction and the mixture was extracted with chloroform. The organic layer was washed with brine, dried (MgSO$_4$) and evaporated. Purification of the residue by flash chromatography (8:2 hexanes/ethyl acetate) gave the title compound (0.17 g, 75%) as a white solid.

LRMS (m/z): 298/300 (M−1)⁻.

$^1$H-NMR δ (CDCl$_3$): 1.84-1.99 (m, 4H), 2.07-2.14 (m, 2H), 2.18-2.24 (m, 2H), 7.26 (br s, 2H).

PREPARATION 4

6'-(4,4,5,5-Tetramethyl-1,3,2-dioxaborolan-2-yl)spiro[cyclopentane-1,3'-indolin]-2'-one

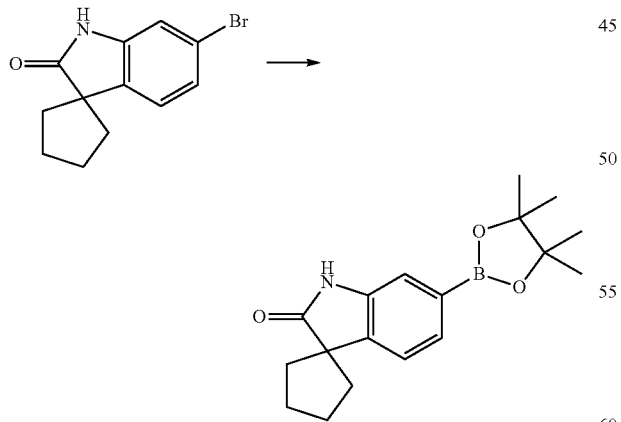

A mixture of 6'-bromospiro[cyclopentane-1,3'-indolin]-2'-one (preparation 2, 0.20 g, 0.77 mmol), bis(pinacolato)diboron (0.29 g, 1.15 mmol), potassium acetate (0.38 g, 3.85 mmol) and 1,1'-bis(diphenylphosphino)ferrocene-palladium(II) dichloride dichloromethane complex (0.06 g, 0.08 mmol) in N,N'-dimethylformamide (2 mL) was heated at 120° C. for 30 minutes in Biotage Initiator Microwave Synthesizer. The mixture was then cooled and the solvent was evaporated. Ethyl acetate was added to the residue and the organic layer was washed with saturated aqueous sodium hydrogen carbonate solution, dried (MgSO$_4$) and evaporated. Purification of the residue by flash chromatography (3:1 hexanes/ethyl acetate) gave the title compound (0.07 g, 30%) as a solid.

LRMS (m/z): 314 (M+1)⁺.

$^1$H-NMR δ (CDCl$_3$): 1.34 (s, 12H), 1.83-1.91 (m, 2H), 1.94-2.10 (m, 4H), 2.15-2.23 (m, 2H), 7.21 (d, J=9.0 Hz, 1H), 7.29 (s, 1H), 7.45 (br s, 1H), 7.45 (d, J=9.0 Hz, 1H).

PREPARATION 5

6-Bromo-2',3',5',6'-tetrahydrospiro[indoline-3,4'-pyran]-2-one

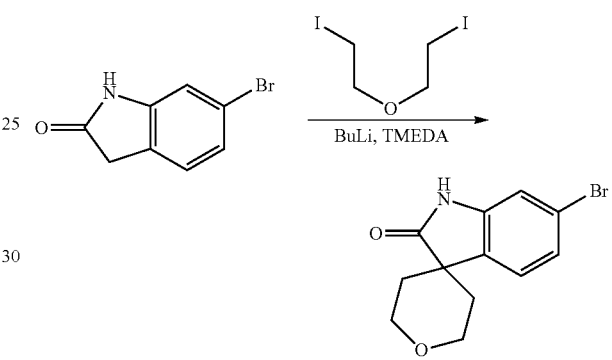

Obtained as a white solid (33%) from 6-bromoindolin-2-one (preparation 1) and 1-iodo-2-(2-iodoethoxy)ethane following the experimental procedure as described in preparation 2 followed by trituration of the crude product with diethyl ether/hexanes (1:1) followed by ethyl acetate and finally diethyl ether.

LRMS (m/z): 282/284 (M+1)⁺.

$^1$H-NMR δ (DMSO-d$_6$): 1.71 (m, 4H), 3.81 (m, 2H), 4.01 (m, 2H), 6.98 (d, J=1.65 Hz, 1H), 7.14 (dd, J=7.97 Hz, J=1.65 Hz, 1H), 7.47 (d, J=7.97 Hz, 1H), 10.55 (s, NH).

PREPARATION 6

6-Bromo-2',3',5',6'-tetrahydrospiro[indoline-3,4'-pyran]-2-one

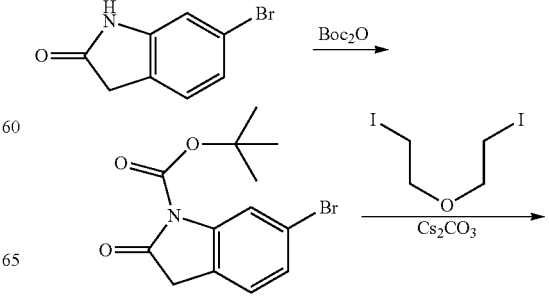

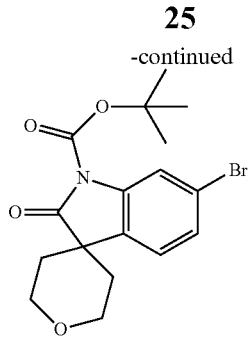

a) tert-butyl 6-bromo-2-oxoindoline-1-carboxylate

Di-tert-butyl dicarbonate (4.63 g, 21.2 mmol) and sodium hydrogen carbonate (10.7 g, 127 mmol) were added to a stirred solution of 6-bromoindolin-2-one (preparation 1, 3.0 g, 14.2 mmol) in tetrahydrofuran (150 mL) and the mixture was heated to reflux. After 3 hours the mixture was cooled and filtered and the filtrate was concentrated in vacuo. Purification of the residue by flash chromatography (10:1 hexanes/ethyl acetate) gave the title compound (3.58 g, 81%) as a white solid.

LRMS (m/z): 312/314 (M+1)$^+$.

$^1$H-NMR δ (CDCl$_3$): 1.65 (s, 9H), 3.66 (s, 2H), 7.10 (d, 1H), 7.27 (d, 1H), 8.03 (s, 1H).

b) tert-butyl 6-bromo-2-oxo-2',3',5',6'-tetrahydrospiro[indoline-3,4'-pyran]-1-carboxylate Cesium carbonate (20.7 g, 63.5 mmol) was added portionwise over a 20 minute period to a stirred solution of tert-butyl 6-bromo-2-oxoindoline-1-carboxylate (preparation 6a, 6.0 g, 16.0 mmol) and 1-iodo-2-(2-iodoethoxy)ethane (6.58 g, 17.6 mmol) in N,N'-dimethylformamide (250 mL) at −20° C. under an argon atmosphere. After the addition the mixture was warmed to room temperature and stirred for 3 hours. Acetic acid (1.1 mL) followed by ethyl acetate and water were added to the reaction mixture and the organic layer was separated, washed with water, dried (MgSO$_4$) and evaporated. Purification of the residue by flash chromatography (10:1 to 5:1 hexanes/ethyl acetate) gave the title compound (4.50 g, 61%) as a pale yellow solid.

LRMS (m/z): 382/384 (M+1)$^+$.

$^1$H-NMR δ (CDCl$_3$): 1.65 (s, 9H), 1.86 (m, 4H), 3.90 (m, 2H), 4.23 (m, 2H), 7.17 (d, J=7.97 Hz, 1H), 7.33 (d, J=7.97 Hz, 1H), 8.07 (s, 1H)

c) 6-bromo-2',3',5',6'-tetrahydrospiro[indoline-3,4'-pyran]-2-one

A mixture of tert-butyl 6-bromo-2-oxo-2',3',5',6'-tetrahydrospiro[indoline-3,4'-pyran]-1-carboxylate (preparation 6b, 4.20 g, 11.0 mmol) and a 5M solution of hydrogen chloride in 1,4-dioxane (25 mL) was stirred at room temperature. After 5 hours, the mixture was concentrated in vacuo to give the title compound (3.20 g, 98%) as a pale pink solid.

LRMS (m/z): 278/280 (M−1)$^+$.

$^1$H-NMR δ (DMSO-d$_6$): 1.71 (m, 4H), 3.81 (m, 2H), 4.01 (m, 2H), 6.98 (d, J=1.65 Hz, 1H), 7.14 (dd, J=7.97 Hz, J=1.65 Hz, 1H), 7.47 (d, J=7.97 Hz, 1H), 10.55 (s, NH).

PREPARATION 7

6-(4,4,5,5-Tetramethyl-1,3,2-dioxaborolan-2-yl)-2',3',5',6'-tetrahydrospiro[indoline-3,4'-pyran]-2-one

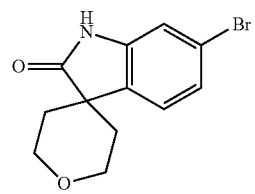

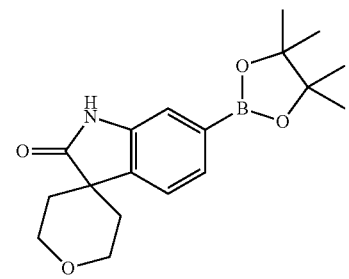

An oven dried resealable Schlenk tube was charged with 6-bromo-2',3',5',6'-tetrahydrospiro[indoline-3,4'-pyran]-2-one (preparation 6, 0.10 g, 0.35 mmol), bis(pinacolato)diboron (0.18 g, 0.71 mmol), potassium acetate (0.07 g, 0.70 mmol) and dimethylsulphoxide (1 mL). The Schlenk tube was subjected to three cycles of evacuation-backfilling with argon, and 1,1'-bis(diphenylphosphino)ferrocene-palladium (II) dichloride dichloromethane complex (0.02 g, 0.02 mmol) was added. After three further cycles of evacuation-backfilling with argon, the Schlenk tube was capped and placed in an oil bath at 90° C. After 16 h, the mixture was cooled and ethyl acetate was added. The organic layer was washed with water, dried (MgSO$_4$) and evaporated. The mixture was filtered through a silica cartridge eluting with hexanes/ethyl acetate to give the title compound in quantitative yield as a pale-yellow oily residue, which was used without further purification.

LRMS (m/z): 330 (M+1)$^+$.

$^1$H-NMR δ (CDCl$_3$): 1.35 (m, 12H), 1.89-1.91 (m, 4H), 3.91-3.95 (m, 2H), 4.23-4.27 (m, 2H), 7.33 (s, 1H), 7.40 (d, J=7.5 Hz, 1H), 7.56 (d, J=7.5 Hz, 1H), 7.77 (br s, 1H).

PREPARATION 8

6-Bromo-3,3-dimethylindolin-2-one

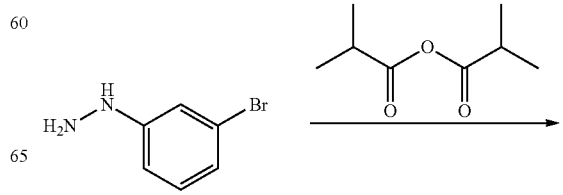

-continued

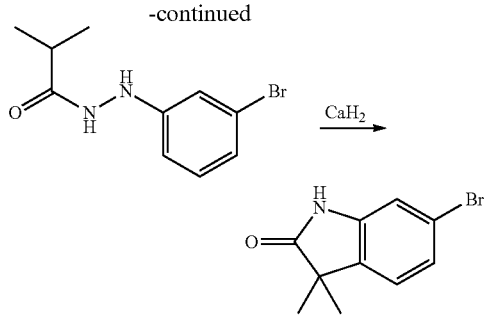

a) N'-(3-Bromophenyl)isobutyrohydrazide

Isobutyric anhydride (4.80 mL, 28.70 mmol) was added dropwise to a stirred solution of 3-bromophenylhydrazine (6.10 g, 27.30 mmol) and triethylamine (7.60 mL, 54.50 mmol) in dichloromethane at 0° C. After the addition the mixture was warmed to ambient temperature and stirred for three hours. The mixture was then concentrated in vacuo and the residue was partitioned between ethyl acetate and water. The organic layer was washed with saturated aqueous sodium hydrogen carbonate, dried (MgSO$_4$) and evaporated. The residue was triturated with diethyl ether and the solid was filtered and dried to give the title compound (5.50 g, 78%) as a white solid.

LRMS (m/z): 257/259 (M+1)$^+$.
$^1$H-NMR δ (CDCl$_3$): 1.22-1.25 (d, 6H), 2.43-2.51 (m, 1H), 6.16 (br s, 1H), 6.72-6.75 (m, 1H), 6.95 (br s, 1H), 7.00-7.11 (m, 2H), 7.33 (br s, 1H).

b) 6-Bromo-3,3-dimethylindolin-2-one

A mixture of the N'-(3-bromophenyl)isobutyrohydrazide (preparation 8a, 3.10 g, 11.90 mmol) and calcium hydride (0.75 g, 17.9 mmol) in a glass tube equipped with an air condenser was heated to 180° C. over 25 minutes then to 210° C. over 15 minutes, and finally to 230° C. over 30 minutes. The mixture was then cooled to room temperature and a mixture of methanol and water was added with stirring and, after gas evolution had ceased, concentrated hydrochloric acid was added until the pH was 1-2. Water was then added and the mixture was heated to 100° C. After 1 hour the mixture was cooled to 0° C., taken to pH 3 with 6N aqueous sodium hydroxide solution and extracted with ethyl acetate. The organic layer was washed with water and brine, dried (MgSO$_4$) and evaporated and the residue was purified by flash chromatography (10:1 hexanes/EtOAc) to give the title compound (0.70 g, 24%) as a white solid.

LRMS (m/z): 240/242 (M+1)$^+$.
$^1$H-NMR δ (CDCl$_3$): 1.39 (s, 6H), 7.06 (d, J=9.0 Hz, 1H), 7.09 (s, 1H), 7.19 (d, J=9.0 Hz, 1H), 8.24 (br s, 1H).

PREPARATION 9

3,3-Dimethyl-6-(4,4,5,5-tetramethyl-1,3,2-dioxaborolan-2-yl)indolin-2-one

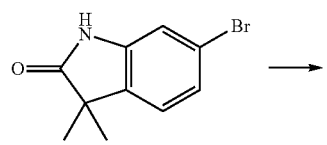

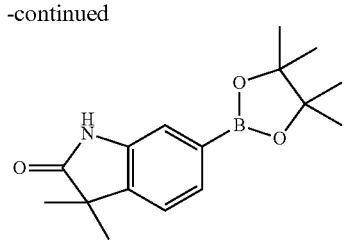

Obtained as a solid from 6-bromo-3,3-dimethylindolin-2-one (preparation 8) following the experimental procedure as described in preparation 7. The desired crude compound was obtained in quantitative yield and was used without further purification.

LRMS (m/z): 288 (M+1)$^+$.
$^1$H-NMR δ (CDCl$_3$): 1.26-1.40 (m, 18H), 7.23 (d, J=7.5 Hz, 1H), 7.34 (s, 1H), 7.54 (d, J=7.5 Hz, 1H), 8.00 (br s, 1H).

PREPARATION 10

6'-Bromo-4,4-difluorospiro[cyclohexane-1,3'-indolin]-2'-one

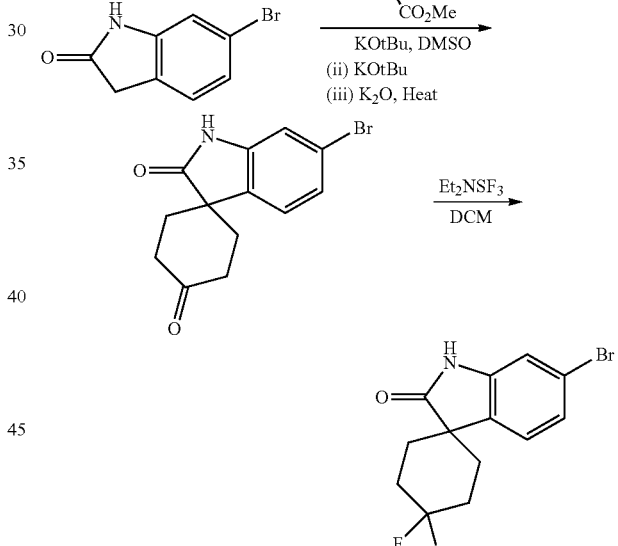

a) 6'-Bromospiro[cyclohexane-1,3'-indoline]-2',4-dione

Potassium tert-butoxide (0.085 g, 0.80 mmol) was added to a suspension of 6-bromoindolin-2-one (preparation 1, 3.00 g, 14.2 mmol) in dimethylsulphoxide (7 mL) and, after stirring for 10 minutes at ambient temperature, the mixture was heated to 40-45° C. and methyl acrylate (4.00 mL, 44.40 mmol) was added dropwise over 70 minutes. After the addition, the mixture was stirred for 1 hour and then further potassium tert-butoxide (3.82 g, 34.00 mmol) was added portionwise over 30 minutes keeping the temperature below 50° C. The mixture was then heated to 100° C. and stirred for 1.5 hours. Water (45 mL) was added and heating was continued at 85° C. for 4 hours and then the mixture was left to cool overnight. The resultant precipitate was filtered and the solid washed with water and hexanes to give the crude product. Recrystallization from ethyl alcohol gave the title compound (1.95 g, 42%) as a white solid.

LRMS (m/z): 292/294 (M−1)⁻.

¹H-NMR δ (DMSO-d₆): 1.99-2.08 (m, 2H), 2.13-2.22 (m, 2H), 2.41-2.50 (m, 2H), 2.82-2.92 (m, 2H), 7.07 (d, J=3.0 Hz, 1H), 7.21 (dd, J=9.0/3.0 Hz, 1H), 7.50 (d, J=9.0 Hz, 1H), 10.70 (br s, 1H).

b) 6'-Bromo-4,4-difluorospiro[cyclohexane-1,3'-indolin]-2'-one (Diethylamino)sulfur trifluoride (0.40 mL, 3.10 mmol) was added dropwise to a suspension of 6'-bromospiro[cyclohexane-1,3'-indoline]-2',4-dione (preparation 10a, 0.30 g, 1.00 mmol) in dichloromethane (3 mL). The mixture was stirred at ambient temperature overnight and then added dropwise to an ice-water mixture. After stirring for 20 minutes, the mixture was neutralized with a 4% aqueous sodium hydrogen carbonate solution and extracted with ethyl acetate. The organic layer was dried (MgSO₄) and evaporated to give an oil. Purification by reverse phase chromatography (C-18 silica from Waters©, water/acetonitrile/methanol as eluents [0.1% v/v formic acid buffered] 0% to 60%) gave the title compound (0.13 g, 41%) as a white solid.

LRMS (m/z): 314/316 (M−1)⁻.

¹H-NMR δ (CDCl₃): 1.80-2.20 (m, 6H), 2.60 (m, 2H), 7.02-7.21 (m, 3H), 7.80 (br s, 1H).

PREPARATION 11

4,4-Difluoro-6'-(4,4,5,5-tetramethyl-1,3,2-dioxaborolan-2-yl)spiro[cyclohexane-1,3'-indolin]-2'-one

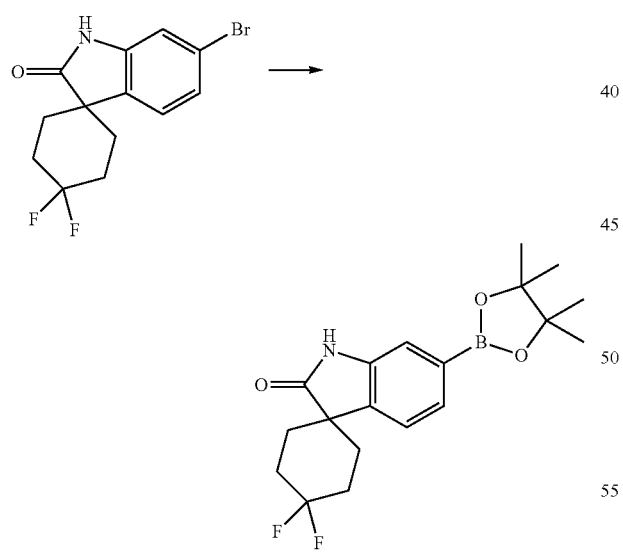

Obtained as a white solid (76%) from 6'-bromo-4,4-difluorospiro[cyclohexane-1,3'-indolin]-2'-on (preparation 10) following the experimental procedure as described in preparation 7, followed by purification of the crude product by flash chromatography (1:1 hexanes/ethyl acetate).

LRMS (m/z): 362 (M−1)⁻.

¹H-NMR δ (CDCl₃): 1.36 (s, 12H), 1.94-2.18 (m, 6H), 2.54-2.75 (m, 2H), 7.27 (d, J=6.0 Hz, 1H), 7.36 (s, 1H), 7.55 (d, J=6.0 Hz, 1H), 8.26 (br s, 1H).

PREPARATION 12

6'-bromo-4-hydroxy-4-methylspiro[cyclohexane-1,3'-indolin]-2'-one

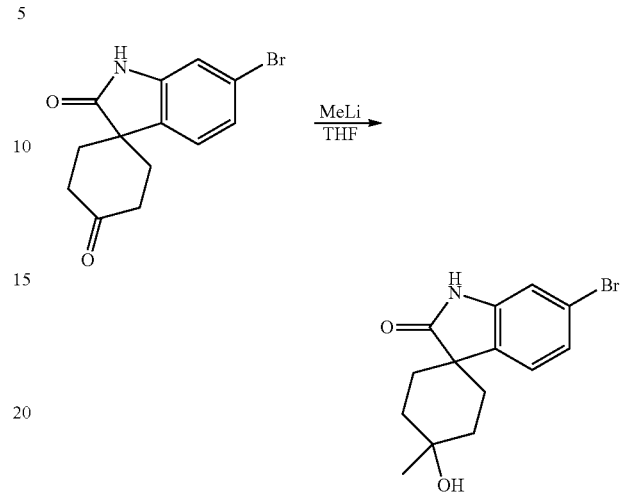

Methyllithium (1.6 M in diethyl ether, 4.89 mL, 7.82 mmol) was added dropwise to a stirred solution of 6'-bromospiro[cyclohexane-1,3'-indoline]-2',4-dione (preparation 10a, 1.00 g, 3.40 mmol) in tetrahydrofuran (30 mL) at −78° C. The mixture was warmed to 0° C. over 3 hours and stirred at room temperature for additional 4.5 hours. Saturated aqueous ammonium chloride (20 mL) was added to the reaction and the mixture was extracted with ethyl acetate. The organic layer was separated, washed with brine, dried (MgSO₄) and evaporated. Purification of the residue by flash chromatography (97:3 dichloromethane/methanol) gave the two pure isomers of the title compound.

The major isomer (661 mg, 63%) was obtained as a white solid

LRMS (m/z): 310/312 (M+1)⁺.

¹H-NMR δ (CDCl₃): 1.39 (s, 3H), 1.47-1.60 (m, 3H), 1.78-1.97 (m, 4H), 2.16-2.26 (m, 2H), 7.08 (d, J=1.6 Hz, 1H), 7.15 (dd, J=8.0/1.65 Hz, 1H), 7.21 (d, J=8.0 Hz, 1H), 7.66 (br s, 1H).

The minor isomer (244 mg, 23%) was obtained as a white solid

LRMS (m/z): 310/312 (M+1)⁺.

¹H-NMR δ (CDCl₃): 1.15 (br s, 1H), 1.39 (s, 3H), 1.61-1.73 (m, 2H), 2.02-2.12 (m, 3H), 2.19-2.28 (m, 3H), 7.01 (s, 1H), 7.16 (s, 2H), 7.51 (br s, 1H).

PREPARATION 13

4-hydroxy-4-methyl-6'-(4,4,5,5-tetramethyl-1,3,2-dioxaborolan-2-yl)spiro[cyclohexane-1,3'-indolin]-2'-one

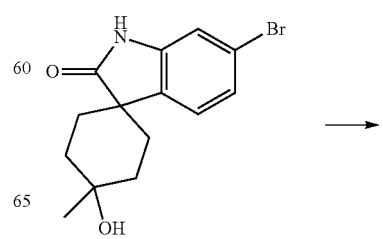

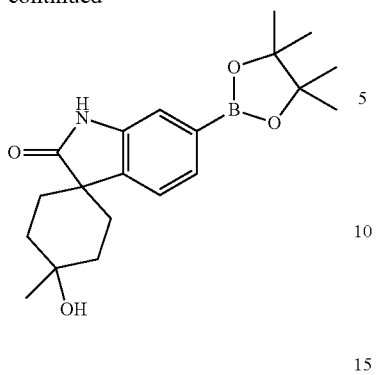

Obtained as a solid from 6'-bromo-4-hydroxy-4-methyl-spiro[cyclohexane-1,3'-indolin]-2'-one (preparation 12, major isomer) following the experimental procedure as described in preparation 7. The desired crude compound was obtained in quantitative yield and was used without further purification.

LRMS (m/z): 358 (M+1)$^+$.

PREPARATION 14

6'-bromo-4-(2-morpholinoethoxy)spiro[cyclohexane-1,3'-indolin]-2'-one

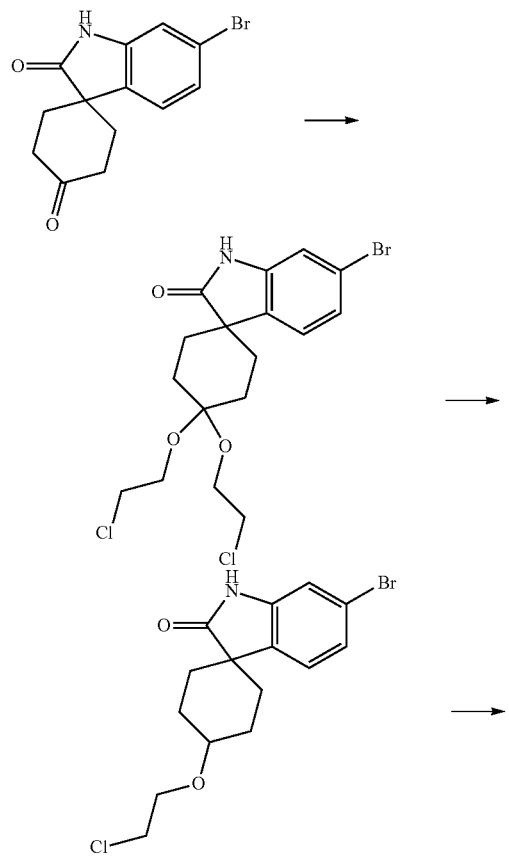

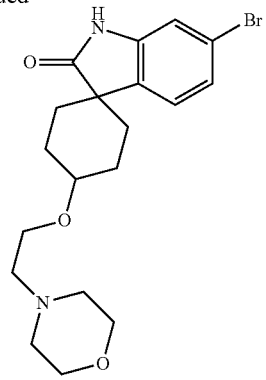

a) 6'-bromo-4,4-bis(2-chloroethoxy)spiro[cyclohexane-1,3'-indolin]-2'-one

A mixture of 6'-bromospiro[cyclohexane-1,3'-indoline]-2',4-dione (preparation 10a, 4.0 g, 13.6 mmol), 2-chloroethanol (20 mL), methanesulphonic acid (0.25 mL) and freshly activated molecular sieves (20 g) in dichloromethane (20 mL) and toluene (40 mL) was stirred at ambient temperature for 4 days. Solid sodium hydrogen carbonate was added to neutralize the mixture and the suspension was filtered and the filter cake was washed with several portions of dichloromethane. The filtrate and washings were combined and evaporated and the residue was purified by flash chromatography (200:1 dichloromethane/methanol) to give the title compound (3.9 g, 66%) as a white solid.

LRMS (m/z): 436 (M−1)$^+$.
$^1$H-NMR δ (DMSO-d$_6$): 1.69 (m, 4H), 1.86 (m, 2H), 2.15 (m, 2H), 3.74 (m, 6H), 3.81 (m, 2H), 6.96 (s, 1H), 7.16 (m, 2H), 10.48 (s, 1H).

b) 6'-bromo-4-(2-morpholinoethoxy)spiro[cyclohexane-1,3'-indolin]-2'-one

A solution of zinc borohydride (0.25 M in diethyl ether, 3.48 mL, 0.87 mmol) was added dropwise over a 5 minute period to a stirred, cooled (ice-bath) suspension of 6'-bromo-4,4-bis(2-chloroethoxy)spiro[cyclohexane-1,3'-indolin]-2'-one (preparation 14a, 0.81 g, 1.9 mmol) in dichloromethane (5 mL). Subsequently, trimethylsilyl chloride (0.46 mL, 3.64 mmol) was added dropwise and the mixture was warmed to ambient temperature and stirred overnight. Saturated aqueous sodium hydrogen carbonate solution and ethyl acetate were added to the mixture and stirring was continued for 1 hour. The organic layer was separated, washed with brine, dried (MgSO$_4$) and evaporated to give a white solid. The solid was taken up in N,N'-dimethylformamide (6 mL), morpholine (0.45 mL, 5.1 mmol) and sodium iodide (0.2 g, 1.6 mmol) were added, and the mixture was heated with stirring to 85° C. in a sealed tube. After stirring overnight, the mixture was diluted with water, saturated aqueous sodium hydrogen carbonate solution was added and the mixture was extracted with ethyl acetate. The organic layer was extracted with 2M aqueous hydrochloric acid solution (3×20 mL) and the combined aqueous layer was washed with ethyl acetate. The resulting aqueous solution was made strongly basic with solid sodium hydroxide and then extracted with ethyl acetate. The organic layer was dried (MgSO$_4$) and evaporated and the residue was purified by flash chromatography (100:1 to 25:1 dichloromethane/methanol) to give the title compound (0.21 g, 28%, 92:8 mixture of isomers) as a white solid.

LRMS (m/z): 409/411 (M+1)⁺.

PREPARATION 15

4-(2-morpholinoethoxy)-6'-(4,4,5,5-tetramethyl-1,3,2-dioxaborolan-2-yl)spiro[cyclohexane-1,3'-indolin]-2'-one

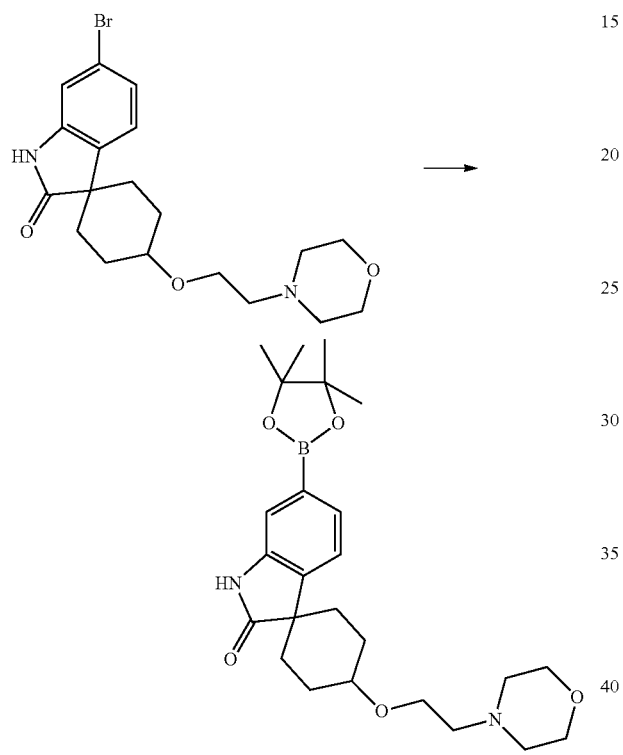

Obtained as a brown oil from 6'-bromo-4-(2-morpholinoethoxy)spiro[cyclohexane-1,3'-indolin]-2'-one (preparation 14) following the experimental procedure as described in preparation 7. The desired crude compound was obtained in quantitative yield and was used without further purification.

LRMS (m/z): 457 (M+1)⁺.

PREPARATION 16

6'-bromo-2,3,5,6-tetrahydrospiro[pyran-4,3'-pyrrolo[3,2-b]pyridin]-2'(1'H)-one

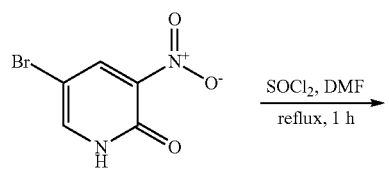

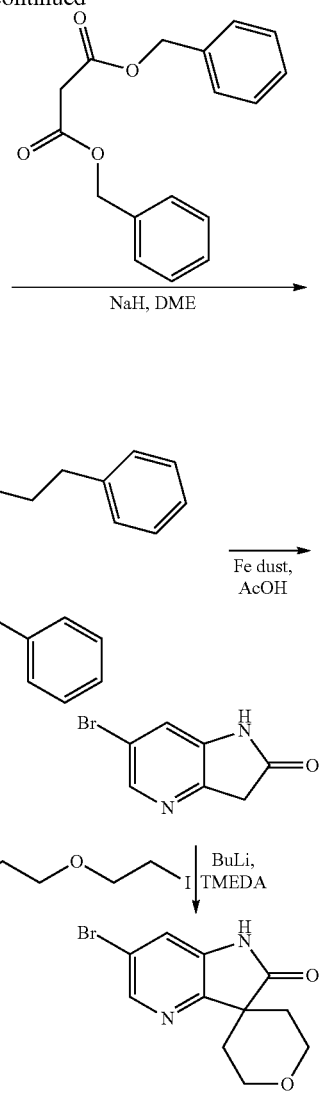

a) 5-Bromo-2-chloro-3-nitropyridine

N,N'-dimethylformamide (3 mL) was added to a mixture of 5-bromo-2-hydroxy-3-nitropyridine (16.54 g, 80 mmol) and thionyl chloride (43 mL) and the mixture was stirred and heated to reflux. After 1 hour, the solution was cooled and the solvent was evaporated. The mixture was co-evaporated with toluene to give a dark solid. Purification by flash chromatography (10:1 hexanes/ethyl acetate) gave the title compound (14.63 g, 82%) as a yellow solid.

¹H-NMR δ (CDCl₃): 8.38 (d, J=3.0 Hz, 1H), 8.70 (d, J=3.0 Hz, 1H).

b) Dibenzyl 2-(5-bromo-3-nitropyridin-2-yl)malonate

Dibenzyl malonate (14.35 g, 50.5 mmol) in dimethoxyethane (40 mL) was added dropwise to a suspension of sodium hydride (60% in mineral oil, 2.00 g, 50.5 mmol) in dimethoxyethane (55 mL). After the addition the mixture was stirred an additional 30 minutes, a solution of bromo-2-chloro-3-nitropyridine (preparation 16a, 6.00 g, 25.3 mmol) in dimethoxymethane (50 mL) was added dropwise, and the red mixture was stirred overnight. The mixture was poured into water, the pH of the solution was adjusted to 3 with 1M aqueous hydrochloric acid and the mixture was extracted with ethyl acetate. The organic layer was washed with brine, dried (MgSO$_4$) and evaporated. The residue was dissolved in the minimum amount of toluene and several volumes of hexanes were added whilst scratching the reaction vessel to give a solid which after filtration and drying furnished the title compound (10.60 g, 80%).

LRMS (m/z): 485/487 (M+1)$^+$.

$^1$H-NMR δ (CDCl$_3$): 5.24 (s, 1H), 5.25 (s, 1H), 7.30-7.35 (m, 10H), 8.61 (s, 1H), 8.80 (s, 1H).

c) 6-Bromo-1H-pyrrolo[3,2-b]pyridin-2(3H)-one

Iron dust (0.82 g, 14.60 mmol) was added to a solution of dibenzyl 2-(5-bromo-3-nitropyridin-2-yl)malonate (preparation 16b, 1.78 g, 3.70 mmol) in glacial acetic acid (50 mL) and the mixture was heated with stirring to 120° C. After 7 hours, the mixture was cooled and left to stand overnight. The reaction was poured onto ice-water and extracted first with ethyl acetate and then with chloroform. The combined organic extract was washed with brine, dried (MgSO$_4$) and evaporated in vacuo. Purification of the residue by flash chromatography (98:2 dichloromethane/methanol) gave the title compound (0.42 g, 54%) as a pink solid.

LRMS (m/z): 213/215 (M+1)$^+$.

$^1$H-NMR δ (DMSO-d$_6$): 3.58 (s, 2H), 7.31 (d, J=3.0 Hz, 1H), 8.18 (d, J=3.0 Hz, 1H), 10.69 (br s, 1H).

d) 6'-bromo-2,3,5,6-tetrahydrospiro[pyran-4,3'-pyrrolo[3,2-b]pyridin]-2'(1'H)-one Obtained as a off-white solid (13%) from 6-bromo-1H-pyrrolo[3,2-b]pyridin-2(3H)-one (preparation 16c) and 1-iodo-2-(2-iodoethoxy)ethane following the experimental procedure as described in preparation 2 followed by purification by flash chromatography (98:2 dichloromethane/methanol).

LRMS (m/z): 283/285 (M+1)$^+$.

$^1$H-NMR δ (DMSO-d$_6$): 1.63-1.84 (m, 4H), 3.87-4.07 (m, 4H), 7.41 (s, 1H), 8.26 (s, 1H), 10.78 (br s, 1H).

PREPARATION 17

2'-oxo-1',2,2',3,5,6-hexahydrospiro[pyran-4,3'-pyrrolo[3,2-b]pyridine]-6'-ylboronic acid

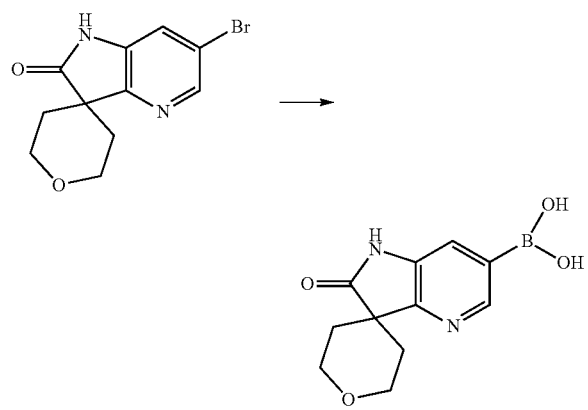

An oven dried resealable Schlenk tube was charged with 6'-bromo-2,3,5,6-tetrahydrospiro[pyran-4,3'-pyrrolo[3,2-b]pyridin]-2'(1'H)-one (preparation 16, 0.350 g, 1.24 mmol), bis(pinacolato)diboron (0.470 g, 1.85 mmol), potassium acetate (0.240 g, 2.48 mmol) and dimethylsulphoxide (4 mL). The Schlenk tube was subjected to three cycles of evacuation-backfilling with argon, and 1,1'-bis(diphenylphosphino)ferrocene-palladium(II) dichloride dichloromethane complex (0.06 g, 0.07 mmol) was added. After three further cycles of evacuation-backfilling with argon, the Schlenk tube was capped and placed in an oil bath at 110° C. After 16 hours, the mixture was cooled and ethyl acetate was added and the organic layer was extracted with 2M aqueous hydrochloric acid solution. The aqueous phase was washed with ethyl acetate and then the pH of the solution was adjusted to 6 with 6M aqueous sodium hydroxide solution and extracted with ethyl acetate. The organic layer was dried (MgSO$_4$) and evaporated to give the title compound in quantitative yield as a brown oily residue, which was used without further purification.

LRMS (m/z): 249 (M+1)$^+$.

PREPARATION 18

6'-bromospiro[cyclohexane-1,3'-pyrrolo[3,2-b]pyridine]-2',4(1'H)-dione

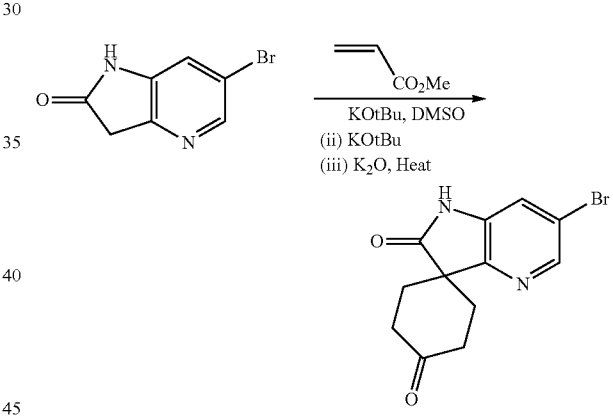

Potassium tert-butoxide (0.03 g, 0.27 mmol) was added to a suspension of 6-bromo-1H-pyrrolo[3,2-b]pyridin-2(3H)-one (preparation 16c, 0.87 g, 4.1 mmol) in dimethylsulphoxide (4 mL) and, after stirring for 10 minutes at room temperature, the mixture was heated to 40-45° C. and methyl acrylate (1.14 mL, 12.71 mmol) was added dropwise over 60 minutes. After the addition, the mixture was stirred for 2 hours and then further potassium tert-butoxide (1.4 g, 12.21 mmol) was added portionwise over 30 minutes keeping the temperature below 50° C. The mixture was then heated to 100° C. and stirred for 2 hours. Water (20 mL) was added and heating was continued at 85° C. for 2 hours and then the mixture was left to cool overnight. Ethyl acetate was added and the organic layer was washed with water, brine, dried (MgSO$_4$) and evaporated to give the title compound (0.60 g, 50%) as a white solid.

LRMS (m/z): 293/295 (M−1)$^+$.

$^1$H-NMR δ (CDCl$_3$): 2.14 (m, 2H), 2.27 (m, 2H), 2.73 (m, 2H), 3.01 (m, 2H), 7.40 (d, J=1.5 Hz, 1H), 8.29 (d, J=1.5 Hz, 1H), 8.44 (br s, 1H).

PREPARATION 19

6'-bromo-4-hydroxy-4-methylspiro[cyclohexane-1, 3'-pyrrolo[3,2-b]pyridin]-2'(1'H)-one

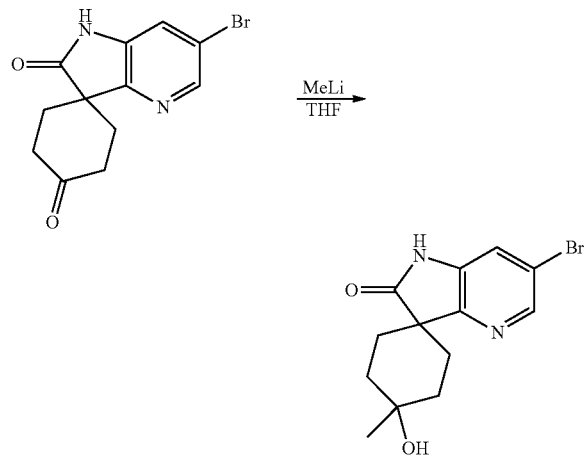

Methyllithium (1.6 M in diethyl ether, 4.88 mL, 7.81 mmol) was added dropwise to a stirred solution of 6'-bromo-spiro[cyclohexane-1,3'-pyrrolo[3,2-b]pyridine]-2',4(1'H)-dione (preparation 18, 1.00 g, 3.39 mmol) in tetrahydrofuran (30 mL) at −78° C. The mixture was warmed to 0° C. over 3 h and stirred overnight at ambient temperature. Additional methyllithium (1.6 M in diethyl ether, 4.24 mL, 6.78 mmol) was added dropwise at −78° C. and the mixture was warmed to ambient temperature stirred overnight at ambient temperature. Saturated aqueous ammonium chloride solution (20 mL) was added to the reaction and the mixture was extracted with ethyl acetate. The organic layer was separated, washed with brine, dried (MgSO$_4$) and evaporated. Purification of the residue by flash chromatography (0.1% Et$_3$N in 1:1 to 3:1 ethyl acetate/hexanes) gave the two pure isomers of the title compound.

The major isomer (283 mg, 27%) was obtained as a white solid

LRMS (m/z): 309/311 (M−1)⁻.

The minor isomer (260 mg, 25%) was obtained as a white solid

LRMS (m/z): 309/311 (M−1)⁻.

PREPARATION 20

4-hydroxy-4-methyl-2'-oxo-1',2'-dihydrospiro[cyclo-hexane-1,3'-pyrrolo[3,2-b]pyridine]-6'-ylboronic acid

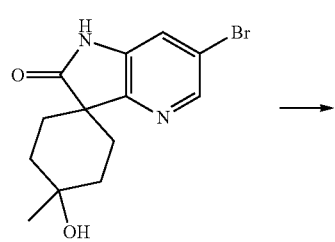

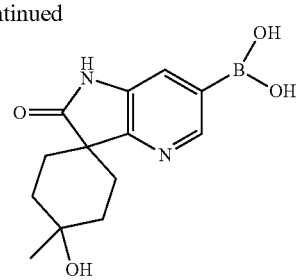

Obtained as a solid from 6'-bromo-4-hydroxy-4-methyl-spiro[cyclohexane-1,3'-pyrrolo[3,2-b]pyridin]-2'(1'H)-one (preparation 19, major isomer) following the experimental procedure as described in preparation 17. The desired crude compound was obtained in quantitative yield and was used without further purification.

LRMS (m/z): 275 (M−1)⁻.

PREPARATION 21

4-hydroxy-4-methyl-2'-oxo-1',2'-dihydrospiro[cyclo-hexane-1,3'-pyrrolo[3,2-b]pyridine]-6'-ylboronic acid

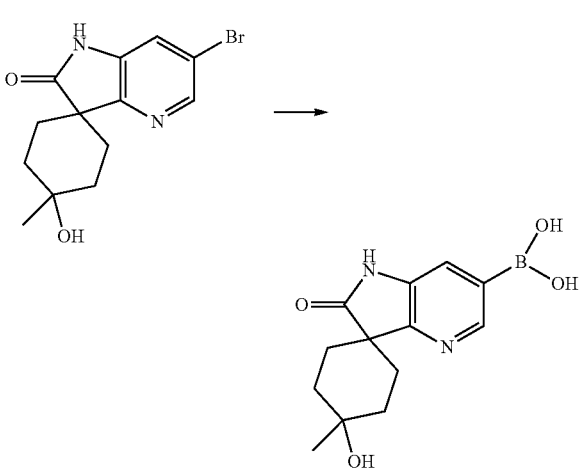

Obtained as a white solid (27%) from 6'-bromo-4-hydroxy-4-methylspiro[cyclohexane-1,3'-pyrrolo[3,2-b]pyridin]-2'(1'H)-one (preparation 19, minor isomer) following the experimental procedure as described in preparation 17 followed by purification by flash chromatography (100% dichloromethane to 70:29:1 dichloromethane/methanol/acetic acid). The residue obtained was dissolved in dichloromethane, washed with a saturated solution of NaHCO$_3$, dried (MgSO$_4$) and evaporated to give the title compound.

LRMS (m/z): 275 (M−1)⁻.

PREPARATION 22

3-(Cyclopropylamino)benzo[d]isoxazol-7-ylboronic acid

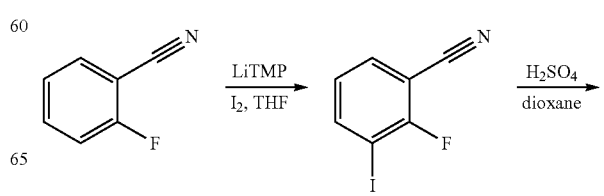

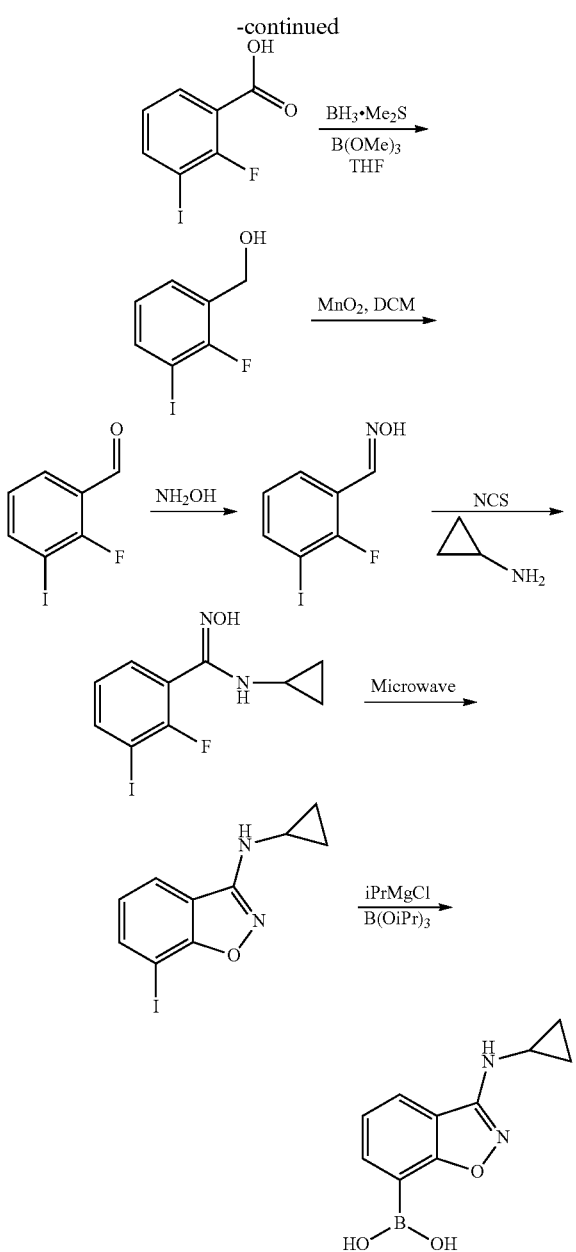

a) 2-Fluoro-3-iodobenzonitrile n-Butyl lithium (2.5 M in hexanes, 16.8 mL, 42 mmol) was added dropwise to a stirred solution of 2,2,6,6-tetramethylpiperidine (6.90 mL, 141 mmol) in tetrahydrofuran (60 mL) at −78° C. The mixture was stirred for 30 minutes at −50° C. then 2-fluorobenzonitrile (4.4 g, 37 mmol) in tetrahydrofuran (25 mL) was added dropwise to the mixture at −78° C. The reaction was warmed to −50° C. over a 30 minute period and then recooled to −78° C. and a solution of iodine (10.20 g, 40 mmol) in tetrahydrofuran (25 mL) was added. Then the mixture was warmed to ambient temperature. After 1 hour, saturated aqueous sodium thiosulphate solution was added to the reaction and the mixture was extracted with diethyl ether. The organic layer was washed with water, brine, dried (MgSO$_4$) and evaporated. Purification of the residue by flash chromatography (20:1 hexanes/ethyl acetate) gave the title compound (7.86 g, 87%) as a solid.

$^1$H-NMR δ (CDCl$_3$): 7.04 (t, J=9.0 Hz, 1H), 7.60-7.65 (m, 1H), 7.99-8.04 (m, 1H).

b) 2-Fluoro-3-iodobenzoic acid

A mixture of 2-fluoro-3-iodobenzonitrile (preparation 22a, 5.00 g, 20.2 mmol), dioxane (16 mL) and sulphuric acid (25 mL) was heated to 115° C. After 4 hours, the mixture was cooled and filtered. Water was added to the filtrate and the mixture was extracted with ethyl acetate. The organic layer was dried (MgSO$_4$) and evaporated to give the title compound (4.42 g, 82%) as a solid.

LRMS (m/z): 265 (M−1)$^-$.

$^1$H-NMR δ (CDCl$_3$): 6.94-7.01 (m, 1H), 7.90-7.97 (m, 2H).

c) (2-Fluoro-3-iodophenyl)methanol

Trimethyl borate (1.92 mL, 17.2 mmol) was added dropwise to a stirred solution of 2-fluoro-3-iodobenzoic acid (preparation 22b, 4.39 g, 16.5 mmol) in tetrahydrofuran (25 mL) at 0° C. and the mixture was stirred for a further 15 minutes at this temperature. Then borane-methyl sulfide complex (10 M, 4.4 mL, 44 mmol) in tetrahydrofuran (3 mL) was added dropwise to the mixture at 0° C. and the mixture was then allowed to warm to room temperature. After 1 hour, the mixture was carefully quenched by dropwise addition of methanol (10 mL). After stirring overnight, the mixture was concentrated in vacuo and ethyl acetate was added to the residue. The organic layer was washed with saturated aqueous potassium carbonate solution, brine, dried (MgSO$_4$) and evaporated to give the title compound (4.03 g, 97%) as an oil.

$^1$H-NMR δ (CDCl$_3$): 1.85 (t, J=6.0 Hz, 1H), 4.78 (d, J=6.0 Hz, 2H), 6.93 (t, J=9.0 Hz, 1H), 7.39-7.44 (m, 1H), 7.66-7.71 (m, 1H).

d) 2-Fluoro-3-iodobenzaldehyde

Manganese (IV) oxide (15.40 g, 177 mmol) was added portionwise to a stirred solution of (2-fluoro-3-iodophenyl)methanol (preparation 22c, 4.03 g, 16 mmol) in dichloromethane (140 mL) and the mixture was stirred at 50° C. After 3 hours, the mixture was filtered through Celite® and the solvent was evaporated to give the title compound (2.10 g, 53%) as a white solid.

$^1$H-NMR δ (CDCl$_3$): 7.07 (t, J=9.0 Hz, 1H), 7.82-7.88 (m, 1H), 7.99-8.04 (m, 1H), 10.34 (s, 1H).

e) 2-Fluoro-3-iodobenzaldehyde oxime

A 50% aqueous solution of hydroxylamine hydrochloride (9 mL, 64.8 mmol) was added to a stirred suspension of 2-fluoro-3-iodobenzaldehyde (preparation 22d, 2.10 g, 8.4 mmol) in ethanol (10 mL) and the mixture was warmed slightly until a solution was formed. After stirring for 3 days at room temperature, the mixture was concentrated in vacuo and water was added to the residue. The mixture was extracted with ethyl acetate and the organic layer was washed with brine, dried (MgSO$_4$) and evaporated to give the title compound (2.15 g, 97%) as a solid.

$^1$H-NMR δ (CDCl$_3$): 6.91-6.96 (m, 1H), 7.71-7.80 (m, 2H), 7.91 (s, 1H), 8.35 (s, 1H).

f) N-Cyclopropyl-2-fluoro-N'-hydroxy-3-iodobenzimidamide

N-chlorosuccinimide (1.20 g, 8.9 mmol) was added portionwise to a stirred solution of 2-fluoro-3-iodobenzaldehyde oxime (preparation 22e, 2.15 g, 8.1 mmol) in N,N'-dimethylformamide (3 mL) and the mixture was stirred for 15 minutes at 55° C. After cooling to ambient temperature, water was added and the mixture was extracted with ethyl acetate. The organic layer was washed with brine, dried (MgSO$_4$) and evaporated. The residue was taken up in tetrahydrofuran (10 mL), cooled by means of an ice-water bath and cyclopropylamine (2.90 mL, 41.9 mmol) was added dropwise. After stirring 3 hours at room temperature, water was added to the reaction and the mixture was extracted with ethyl acetate. The organic layer was washed with brine, dried (MgSO$_4$) and evaporated to give the title compound (2.53 g, 96%) as a white solid.

LRMS (m/z): 321 (M+1)$^+$.

$^1$H-NMR δ (CDCl$_3$): 0.35-0.43 (m, 4H), 2.41-2.47 (m, 1H), 5.64 (br s, 1H), 6.96 (t, J=6.0 Hz, 1H), 7.34-7.40 (m, 1H), 7.80-7.86 (m, 1H).

g) N-Cyclopropyl-7-iodobenzo[d]isoxazol-3-amine

A mixture of N-cyclopropyl-2-fluoro-N'-hydroxy-3-iodobenzimidamide (preparation 22f, 2.15 g, 8.1 mmol) and 1,8-diazabicyclo[5.4.0]undec-7-ene (1.30 mL, 8.7 mmol) in tetrahydrofuran (13 mL) was heated at 150° C. for 150 minutes in Biotage Initiator Microwave Synthesizer. Then, the mixture was cooled to ambient temperature and evaporated. The residue was partitioned between water and ethyl acetate and the organic layer was washed with brine, dried (MgSO$_4$) and evaporated. The crude residue was purified by flash chromatography (3:1 hexanes/ethyl acetate) to give the title compound (1.61 g, 68%) as a white solid.

LRMS (m/z): 301 (M+1)$^+$.

$^1$H-NMR δ (CDCl$_3$): 0.68-0.73 (m, 2H), 0.84-0.90 (m, 2H), 2.81-2.88 (m, 1H), 6.97 (t, J=9.0 Hz, 1H), 7.55 (d, J=9.0 Hz, 1H), 7.87 (d, J=9.0 Hz, 1H).

h) 3-(Cyclopropylamino)benzo[d]isoxazol-7-ylboronic acid

Isopropylmagnesium chloride (2.0 M in tetrahydrofuran, 2.83 mL, 5.7 mmol) was added dropwise over 20 minutes to a stirred solution of N-cyclopropyl-7-iodobenzo[d]isoxazol-3-amine (preparation 22 g, 0.50 g, 1.7 mmol) in tetrahydrofuran (10 mL) at −10° C. The mixture was stirred for 1 hour at 0° C. then triisopropyl borate (1.15 mL, 5.0 mmol) was added dropwise over 10 minutes and the mixture was stirred for 1 hour at 0° C. Then, the mixture was warmed to room temperature and stirred overnight. Water was then added, the mixture was cooled by means of an ice-water bath and the pH was adjusted to 1 with 2M aqueous hydrochloric acid. The mixture was extracted with ethyl acetate and the organic layer was washed with brine, dried (MgSO$_4$) and evaporated. The residue was triturated with diethyl ether and the solid was filtered and dried to give the title compound (140 mg, 39%) as a white solid.

LRMS (m/z): 219 (M+1)$^+$.

PREPARATION 23

7-Iodo-N-(4-methoxybenzyl)-6-methylbenzo[d]isoxazol-3-amine

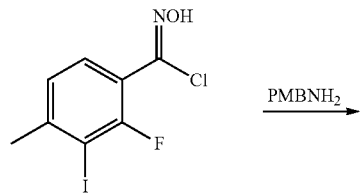

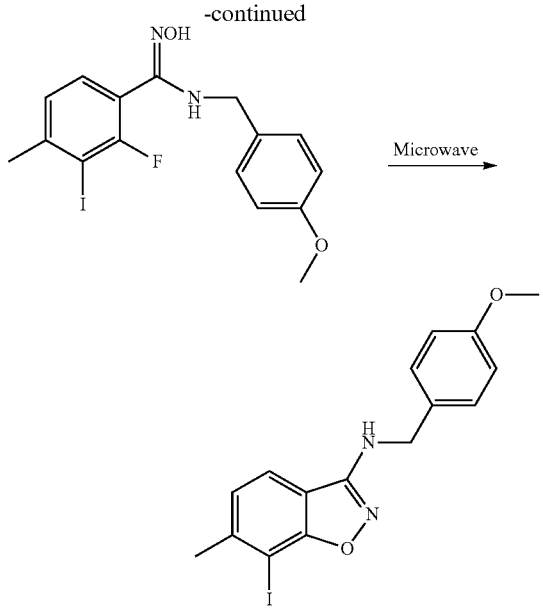

a) 2-Fluoro-N'-hydroxy-3-iodo-N-(4-methoxybenzyl)-4-methylbenzimidamide

4-Methoxybenzylamine (2.00 mL, 15.2 mmol) was added dropwise to a solution of 2-fluoro-N-hydroxy-3-iodo-4-methylbenzimidoyl chloride (WO2006094187, 1.46 g, 4.7 mmol) in tetrahydrofuran (20 mL) and the mixture was stirred at ambient temperature overnight. Water was added and the mixture was extracted with ethyl acetate. The organic layer was washed with brine, dried (MgSO$_4$) and evaporated to give a semi-solid. The solid was triturated with a hexanes/diethyl ether mixture and the solid was filtered and dried to give the title compound (1.66 g, 86%) as a white solid.

LRMS (m/z): 415 (M+1)$^+$.

$^1$H-NMR δ (CDCl$_3$): 2.50 (s, 3H), 3.80 (s, 3H), 4.07 (d, J=6.0 Hz, 2H), 5.61 (br s, 1H), 6.60-6.86 (m, 2H), 7.04-7.12 (m, 3H), 7.21-7.26 (m, 1H).

b) 7-Iodo-N-(4-methoxybenzyl)-6-methylbenzo[d]isoxazol-3-amine 1,8-Diazabicyclo[5.4.0]undec-7-ene (0.31 mL, 2.0 mmol) was added dropwise to a solution of 2-fluoro-N'-hydroxy-3-iodo-N-(4-methoxybenzyl)-4-methylbenzimidamide (preparation 23a, 0.80 g, 1.9 mmol) in tetrahydrofuran (10 mL). The mixture was then heated under microwave conditions ("Initiator sixty" from Biotage®) at 150° C. for 4 hours under an argon atmosphere. The mixture was then poured into water and extracted with ethyl acetate. The organic layer was washed with brine, dried (MgSO$_4$) and evaporated. The residue was purified by flash chromatography (10:1 to 4:1 hexanes/ethyl acetate) to give the title compound (0.29 g, 38%) as a white solid.

LRMS (m/z): 395 (M+1)$^+$.

$^1$H-NMR δ (CDCl$_3$): 2.56 (s, 3H), 3.81 (s, 3H), 4.39 (br s, 1H), 4.51 (d, J=6.0 Hz, 2H), 6.90 (d, J=9.0 Hz, 2H), 7.07 (d, J=9.0 Hz, 1H), 7.25 (d, J=9.0 Hz, 1H), 7.36 (d, J=9.0 Hz, 2H).

PREPARATION 24

7-Iodo-6-methyl-1,2-benzisoxazol-3-amine

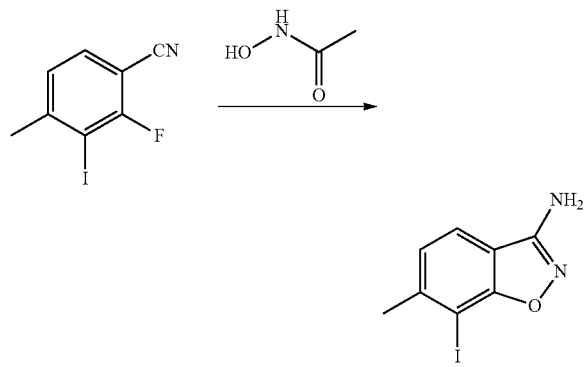

Potassium tert-butoxide (2.20 g, 19.2 mmol) was added to a solution of N-hydroxyacetamide (1.44 g, 19.2 mmol) in N,N'-dimethylformamide (25 mL) under argon. The resulting white suspension was stirred at room temperature for 30 minutes and then 2-fluoro-3-iodo-4-methylbenzonitrile (WO2006094187, 2.00 g, 7.7 mmol) was added and the mixture was stirred at room temperature for 6 hours. Further N-hydroxyacetamide (0.29 g, 3.9 mmol) and potassium tert-butoxide (0.45 g, 3.9 mmol) were added and the mixture was stirred at room temperature overnight. The solvent was evaporated under reduced pressure and water and ethyl acetate were added. The organic layer was separated and the aqueous phase was extracted with further ethyl acetate. The combined organic layers were washed with brine, dried, (MgSO$_4$) and evaporated. The residue was purified by flash chromatography (9:1 hexanes/ethyl acetate to ethyl acetate) to yield the title compound (1.79 g, 81%) as a solid.

LRMS (m/z): 275 (M+1)$^+$.

$^1$H-NMR δ (CDCl$_3$): 2.58 (s, 3H), 7.13 (d, J=8.0 Hz, 1H), 7.36 (d, J=9.0 Hz, 1H).

PREPARATION 25

7-Iodo-6-methyl-1H-indazol-3-amine

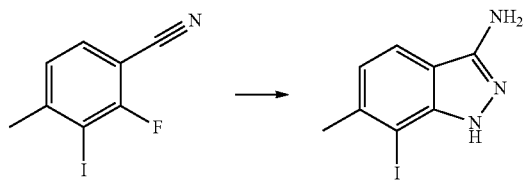

A solution of hydrazine monohydrate (0.56 mL, 11.6 mmol) and 2-fluoro-3-iodo-4-methylbenzonitrile (WO2006094187, 1.00 g, 3.8 mmol) in ethanol (7 mL) was stirred and heated to 100° C. in a sealed tube. After stirring overnight, the mixture was cooled and water was added. The resultant precipitate was filtered, washed with water and hexanes, and then dried in vacuo to give the title compound (0.91 g, 87%) as a yellow solid.

$^1$H-NMR δ (CDCl$_3$): 2.55 (s, 3H), 4.09 (br s, 2H), 6.96 (d, J=9.0 Hz, 1H), 7.41 (d, J=9.0 Hz, 1H), 8.87 (br s, 1H).

PREPARATION 26

N-Cyclopropyl-8-iodo[1,2,4]triazolo[4,3-a]pyridin-3-amine

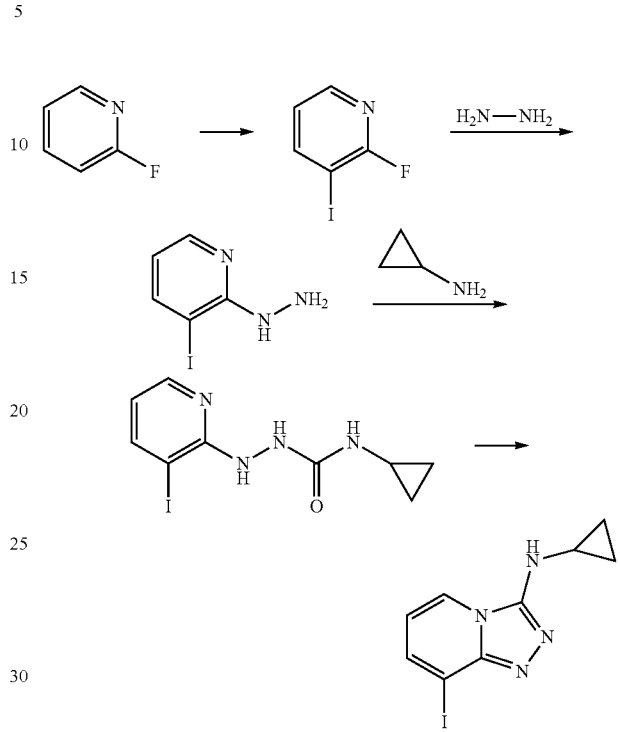

a) 2-Fluoro-3-iodopyridine

Obtained as a yellow solid (63%) following the procedure as described in *J. Org. Chem.* 1993, 58 (27), 7832-7838.

b) 2-Hydrazino-3-iodopyridine

Hydrazine hydrate (12.50 mL, 256 mmol) was added dropwise to a solution of 2-fluoro-3-iodopyridine (preparation 26a, 5.72 g, 25.7 mmol) in ethanol (43 mL) and the resulting mixture was stirred at room temperature for 24 hours and then at 35° C. for a further 24 hours. The solvent was then evaporated in vacuo and water was added. The white solid that formed was filtered, washed with water and dried to yield the title compound (2.78 g, 46%) as a white solid which was used without further purification.

LRMS (m/z): 236 (M+1)$^+$.

c) N-Cyclopropyl-2-(3-iodopyridin-2-yl)hydrazinecarboxamide

Cyclopropylamine (0.12 g, 2.2 mmol) in dichloromethane (3 mL) was added to a solution of triphosgene (0.22 g, 0.74 mmol) in dichloromethane (5 mL) at 0° C. under argon. Triethylamine (0.59 mL, 4.2 mmol) in dichloromethane (3 mL) was then added and the resulting mixture was stirred at room temperature for 2 hours and then cooled to 0° C. 2-Hydrazino-3-iodopyridine (preparation 26b, 0.50 g, 2.1 mmol) in dichloromethane (5 mL) was added and the resulting mixture was stirred at room temperature overnight. The solution was cooled to 0° C. and a solid precipitated. The solid was filtered, washed with diethyl ether and dried to yield the title compound (0.56 g, 83%) as a white solid.

LRMS (m/z): 319 (M+1)+.

$^1$H-NMR δ (DMSO-$d_6$): 0.37 (m, 2H), 0.55 (m, 2H), 2.45 (m, 1H), 6.48 (br s, 1H), 6.49 (br s, 1H), 6.52 (dd, J=7.4/4.7 Hz, 1H), 7.51 (br s, 1H), 7.64 (br s, 1H), 7.98 (dd, J=7.4/1.4 Hz, 1H), 8.07 (dd, J=4.7/1.4 Hz, 1H).

d) N-Cyclopropyl-8-iodo[1,2,4]triazolo[4,3-a]pyridin-3-amine

A mixture of N-cyclopropyl-2-(3-iodopyridin-2-yl)hydrazinecarboxamide (preparation 26c, 0.56 g, 1.8 mmol) and phosphorous oxychloride (7 mL) was stirred at 75° C. overnight. The reaction mixture was cooled to ambient temperature, added slowly to an ice-water mixture and then was basified to pH 8 with aqueous sodium hydroxide solution. The aqueous solution was extracted with ethyl acetate and the organic layer was washed with brine, dried (MgSO$_4$) and the solvent evaporated in vacuo to yield the title compound (0.50 g, 88%) as a solid.

LRMS (m/z): 301/302 (M+1)+.

$^1$H-NMR δ (DMSO-$d_6$): 0.50-0.55 (m, 2H), 0.71-0.77 (m, 2H), 2.75-2.82 (m, 1H), 6.52 (dd, J=6.0/6.0 Hz, 1H), 7.00 (s, 1H), 7.62 (d, J=6.0 Hz, 1H), 8.04 (d, J=6.0 Hz, 1H).

PREPARATION 27

N-(Cyclopropylmethyl)-8-iodo[1,2,4]triazolo[4,3-a]pyridin-3-amine

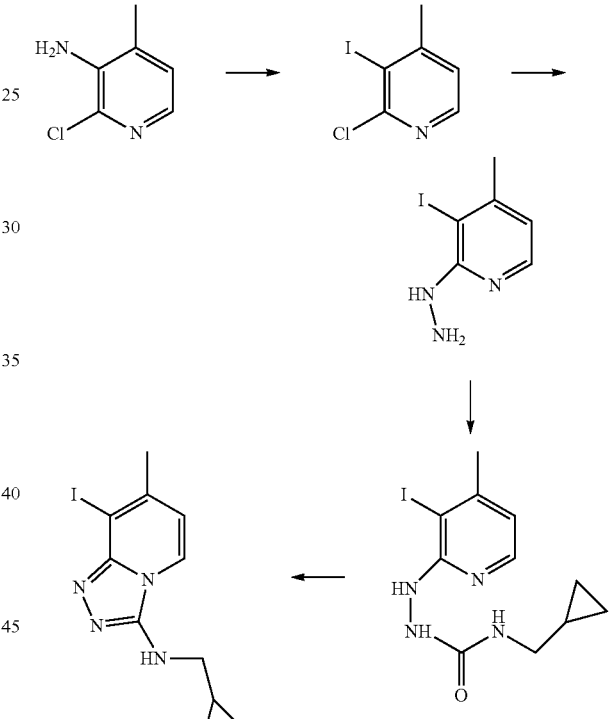

a) N-(Cyclopropylmethyl)-2-(3-iodopyridin-2-yl)hydrazinecarboxamide

Obtained as a white solid (85%) from 2-hydrazino-3-iodopyridine (preparation 26b) and cyclopropylmethanamine following the experimental procedure as described in preparation 26c.

LRMS (m/z): 333 (M+1)+.

$^1$H-NMR δ (CDCl$_3$): 0.15 (m, 2H), 0.43 (m, 2H), 0.92 (m, 1H), 3.13 (t, J=5.8 Hz, 2H), 5.76 (br s, 1H), 6.51-6.65 (m, 3H), 7.96 (d, J=7.8 Hz, 1H), 8.17 (d, J=5.0 Hz, 1H).

b) N-(Cyclopropylmethyl)-8-iodo[1,2,4]triazolo[4,3-a]pyridin-3-amine

Obtained as a solid (33%) from N-(cyclopropylmethyl)-2-(3-iodopyridin-2-yl)hydrazinecarboxamide (preparation 27a) following the experimental procedure as described in preparation 26d.

LRMS (m/z): 315 (M+1)+.

$^1$H-NMR δ (MeOD): 0.39 (m, 2H), 0.67 (m, 2H), 1.29 (m, 1H), 3.74 (m, 2H), 6.97 (m, 1H), 8.21 (m, 1H), 8.46 (m, 1H).

PREPARATION 28

N-(Cyclopropylmethyl)-8-iodo-7-methyl-[1,2,4]triazolo[4,3-a]pyridin-3-amine

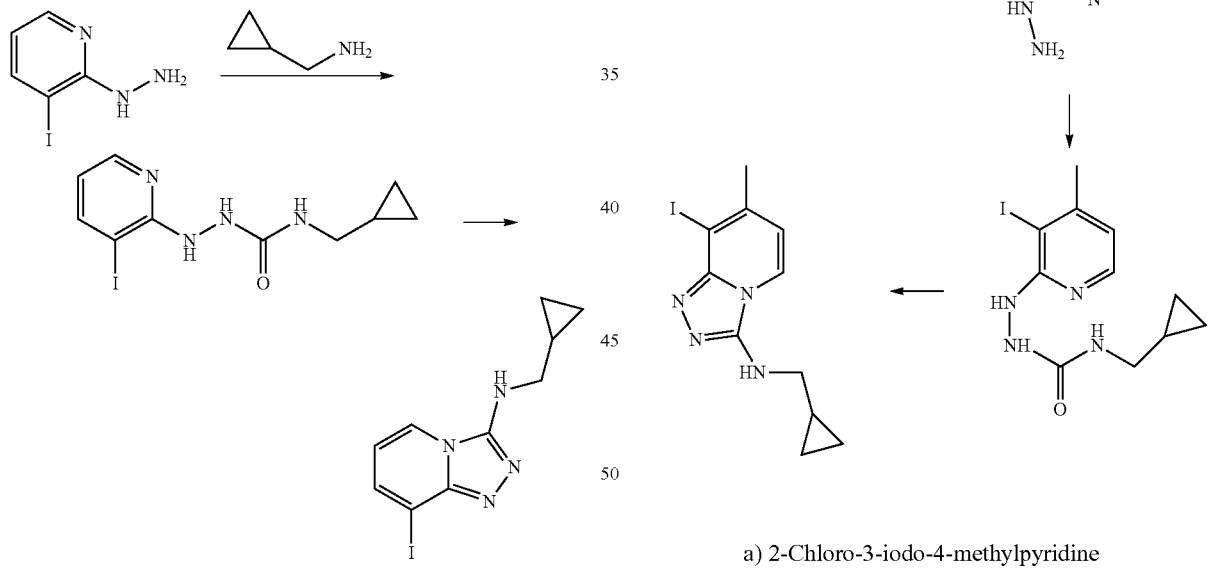

a) 2-Chloro-3-iodo-4-methylpyridine

A mixture of 2-chloro-4-methylpyridin-3-amine (1.0 g, 7.0 mmol) and concentrated hydrochloric acid (4.4 mL) was cooled to 0° C. and a solution of sodium nitrite (0.5 g, 7.5 mmol) in water (8 mL) was added dropwise. The mixture was stirred for 1 hour at 0° C. and then was added dropwise to a stirred solution of potassium iodide (1.6 g, 9.6 mmol) in water (9 mL). The mixture was warmed to ambient temperature and stirred overnight. The mixture was extracted with diethyl ether and the organic phase was washed with aqueous sodium thiosulphate, brine, dried (MgSO$_4$) and evaporated in vacuo. The crude product was recrystallized from hexane to give the title compound (0.88 g, 47%) as a white solid.

LRMS (m/z): 254 (M+1)⁺.

¹H-NMR δ (CDCl₃): 2.50 (s, 3H), 7.05 (d, J=4.9 Hz, 1H), 8.15 (d, J=4.9 Hz, 1H).

b) 2-Hydrazinyl-3-iodo-4-methylpyridine

A mixture of 2-chloro-3-iodo-4-methylpyridine (preparation 28a, 2.0 g, 7.9 mmol) and hydrazine hydrate (1.2 mL, 24.2 mmol) in pyridine (12 mL) under an argon atmosphere was stirred and heated to reflux. After 24 hours, the mixture was cooled and evaporated to dryness. The crude mixture was triturated with water and the solid was filtered and washed with water to give the title compound (1.71 g, 87%) which was used without further purification in the next reaction.

LRMS (m/z): 250 (M+1)⁺.

¹H-NMR δ (CDCl₃): 2.36 (s, 3H), 4.00 (br s, 2H), 6.25 (br s, 1H), 6.57 (d, J=5.0 Hz, 1H), 7.95 (d, J=5.0 Hz, 1H).

c) N-(Cyclopropylmethyl)-2-(3-iodo-4-methylpyridin-2-yl)hydrazinecarboxamide

A solution of cyclopropylmethanamine (0.33 mL, 3.7 mmol) in dichloromethane (2 mL) was added dropwise to a solution of triphosgene (0.39 g, 1.3 mmol) in dichloromethane (15 mL) kept at 0° C. under an argon atmosphere. After 5 minutes, a solution of triethylamine (1.0 mL, 7.2 mmol) in dichloromethane was added dropwise and the mixture was warmed to ambient tempertaure. After stirring two hours, the mixture was cooled to 0° C. and 2-hydrazinyl-3-iodo-4-methylpyridine (preparation 28b, 0.91 g, 3.6 mmol) in dichloromethane (8 mL) was added dropwise. The mixture was warmed to ambient temperature and stirred overnight. The solid precipitate was filtered, washed with diethyl ether and dried to yield the title compound (0.85 g, 68%) as a beige solid.

LRMS (m/z): 347 (M+1)⁺.

¹H-NMR δ (CDCl₃): 0.13-0.18 (m, 2H), 0.40-0.46 (m, 2H), 0.91-0.96 (m, 1H), 2.40 (s, 3H), 3.11 (t, J=6.3 Hz, 2H), 5.69 (br s, 1H), 6.20 (br s, 1H), 6.60 (br s, 1H), 6.74 (d, J=5.0 Hz, 1H), 8.01 (d, J=5.0 Hz, 1H).

d) N-(Cyclopropylmethyl)-8-iodo-7-methyl-[1,2,4]triazolo[4,3-a]pyridin-3-amine

A mixture of N-(cyclopropylmethyl)-2-(3-iodo-4-methylpyridin-2-yl)hydrazinecarboxamide (preparation 28c, 0.85 g, 2.5 mmol) and phosphorous oxychloride (10 mL) was stirred at 75° C. overnight. The reaction mixture was cooled to ambient temperature and added slowly to an ice-water mixture and then ethyl acetate was added. To the cooled, stirred, biphasic mixture was added aqueous sodium hydroxide solution until the aqueous layer reached a pH of 8. The organic layer was washed with water, brine, dried (MgSO₄) and the solvent evaporated in vacuo to yield the title compound (0.77 g, 96%) as a pale yellow solid.

LRMS (m/z): 329 (M+1)⁺.

¹H-NMR δ (DMSO-d₆): 0.24-0.29 (m, 2H), 0.44-0.50 (m, 2H), 1.11-1.21 (m, 1H), 2.38 (s, 3H), 3.21 (m, 2H), 6.66 (d, J=7.0 Hz, 1H), 6.70 (t, J=5.5 Hz, 1H), 8.02 (d, J=7.0 Hz, 1H).

EXAMPLE 1

6'-(3-(Cyclopropylamino)-6-methylbenzo[d]isoxazol-7-yl)spiro[cyclopentane-1,3'-indolin]-2'-one

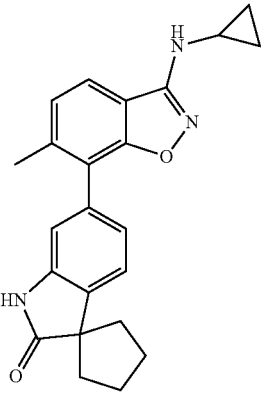 [SMILES: Cc1ccc2c(NC3CC3)noc2c1-c1ccc2c(c1)NC(=O)C21CCCC1]

An oven-dried resealable Schlenk tube was charged with 6'-(4,4,5,5-tetramethyl-1,3,2-dioxaborolan-2-yl)spiro[cyclopentane-1,3'-indolin]-2'-one (preparation 4, 0.060 g, 0.19 mmol), N-cyclopropyl-7-iodo-6-methylbenzo[d]isoxazol-3-amine (WO2006094187, 0.090 g, 0.29 mmol), 1,4-dioxane (1.2 mL) and a 2M aqueous caesium carbonate solution (0.29 mL, 0.58 mmol). The Schlenk tube was subjected to three cycles of evacuation-backfilling with argon, and 1,1'-bis(diphenylphosphino)ferrocene-palladium(II) dichloride dichloromethane complex (0.015 g, 0.02 mmol) was added. After three further cycles of evacuation-backfilling with argon, the Schlenk tube was sealed and the mixture was stirred and heated in an oil bath to 100-110° C. After 20 hours, the mixture was cooled and partitioned between water and ethyl acetate. The organic extract was dried (MgSO₄) and evaporated in vacuo. Purification of the residue by flash chromatography (98:2 dichloromethane/methanol) gave the title compound (0.017 g, 28%) as a yellow solid.

LRMS (m/z): 374 (M+1)⁺.

¹H-NMR δ (DMSO-d₆): 0.71-0.77 (m, 2H), 0.86-0.92 (m, 2H), 1.90-2.30 (m, 8H), 2.38 (s, 3H), 2.79-2.86 (m, 1H), 6.94 (s, 1H), 7.05 (dd, J=1.4, 7.7 Hz, 1H), 7.15 (d, J=8.0 Hz, 1H), 7.26 (d, J=7.7 Hz, 1H), 7.45 (d, J=8.0 Hz, 1H), 8.27 (br s, 1H).

EXAMPLE 2

6'-(3-(Cyclopropylamino)benzo[d]isoxazol-7-yl)spiro[cyclopentane-1,3'-indolin]-2'-one

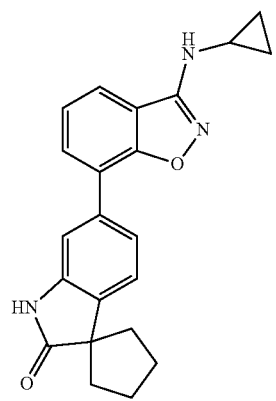 [SMILES: O=C1Nc2cc(-c3cccc4c(NC5CC5)noc34)ccc2C12CCCC2]

Obtained as a white solid (70%) from 3-(cyclopropylamino)benzo[d]isoxazol-7-ylboronic acid (preparation 22) and 6'-bromospiro[cyclopentane-1,3'-indolin]-2'-one (preparation 2) following the experimental procedure as described in example 1 followed by purification by flash chromatography (99:1 dichloromethane/methanol).

LRMS (m/z): 360 (M+1)+.

$^1$H-NMR δ (CDCl$_3$): 0.71-0.77 (m, 2H), 0.86-0.92 (m, 2H), 1.89-1.99 (m, 2H), 2.00-2.15 (m, 4H), 2.17-2.30 (m, 2H), 2.84-2.97 (m, 1H), 7.27 (d, J=6.0 Hz, 1H), 7.29 (d, J=6.0 Hz, 1H), 7.31 (d, J=9.0 Hz, 1H), 7.51 (s, 1H), 7.55 (d, J=9.0 Hz, 1H), 7.67 (d, J=9.0 Hz, 1H), 7.86 (br s, 1H).

EXAMPLE 3

5'-Chloro-6'-(3-(cyclopropylamino)benzo[d]isoxazol-7-yl)spiro[cyclopentane-1,3'-indolin]-2'-one

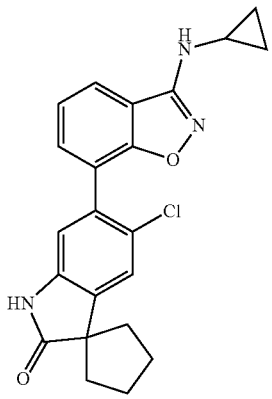 [SMILES: O=C1Nc2cc(-c3cccc4c(NC5CC5)noc34)c(Cl)cc2C12CCCC2]

Obtained as a white solid (14%) from 3-(cyclopropylamino)benzo[d]isoxazol-7-ylboronic acid (preparation 22) and 6'-bromo-5'-chlorospiro[cyclopentane-1,3'-indolin]-2'-one (preparation 3) following the experimental procedure as described in example 1 followed by purification by flash chromatography (1:1 to 1:3 hexanes/ethyl acetate).

LRMS (m/z): 394 (M+1)+.

$^1$H-NMR δ (CDCl$_3$): 0.71-0.76 (m, 2H), 0.85-0.91 (m, 2H), 1.62 (s, 3H), 1.90-2.15 (m, 6H), 2.18-2.28 (m, 2H), 2.85-2.91 (m, 2H), 4.81 (s, 1H), 7.04 (s, 1H), 7.27 (s, 1H), 7.32 (s, 1H), 7.56 (dd, J=7.0/1.5 Hz, 1H), 7.62 (dd, J=7.0/1.5 Hz, 1H), 7.95 (br s, 1H).

EXAMPLE 4

6-(3-(Cyclopropylamino)-6-methylbenzo[d]isoxazol-7-yl)-2',3',5',6'-tetrahydrospiro [indoline-3,4'-pyran]-2-one

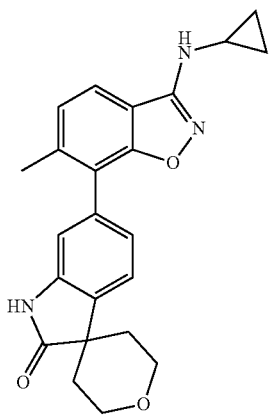 [SMILES: Cc1ccc2c(NC3CC3)noc2c1-c1ccc2c(c1)NC(=O)C21CCOCC1]

Obtained as a white solid (42%) from 6-(4,4,5,5-tetramethyl-1,3,2-dioxaborolan-2-yl)-2',3',5',6'-tetrahydrospiro[indoline-3,4'-pyran]-2-one (preparation 7) and N-cyclopropyl-7-iodo-6-methylbenzo[d]isoxazol-3-amine (WO2006094187) following the experimental procedure as described in example 1 followed by purification by flash chromatography (98:2 dichloromethane/methanol).

LRMS (m/z): 390 (M+1)+.

$^1$H-NMR δ (DMSO-d$_6$): 0.48-0.57 (m, 2H), 0.66-0.75 (m, 2H), 1.72-1.83 (m, 4H), 2.30 (s, 3H), 2.57-2.70 (m, 1H), 3.80-3.92 (m, 4H), 4.01-4.14 (m, 4H), 6.85 (br s, 1H), 6.99 (d, J=7.0 Hz, 1H), 7.19-7.27 (m, 2H), 7.64 (d, J=9.0 Hz, 1H), 10.52 (br s, 1H).

EXAMPLE 5

6'-(3-(Cyclopropylamino)-6-methylbenzo[d]isoxazol-7-yl)-4,4-difluorospiro [cyclohexane-1,3'-indolin]-2'-one

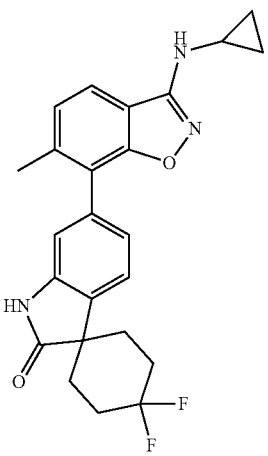 [SMILES: Cc1ccc2c(NC3CC3)noc2c1-c1ccc2c(c1)NC(=O)C21CCC(F)(F)CC1]

Obtained as a white solid (35%) from 4,4-difluoro-6'-(4,4,5,5-tetramethyl-1,3,2-dioxaborolan-2-yl)spiro[cyclohexane-1,3'-indolin]-2'-one (preparation 11) and N-cyclopropyl-7-iodo-6-methylbenzo[d]isoxazol-3-amine (WO2006094187) following the experimental procedure as described in example 1 followed by purification by flash chromatography (60:40 to 25:75 hexanes/ethyl acetate).

LRMS (m/z): 424 (M+1)+.

$^1$H-NMR δ (CDCl$_3$): 0.69-0.74 (m, 2H), 0.84-0.90 (m, 2H), 2.05-2.10 (m, 4H), 2.12-2.22 (m, 2H), 2.40 (s, 3H), 2.55-2.77 (m, 2H), 2.82-2.90 (m, 1H), 4.70 (s, 1H), 6.98 (d, J=1.5 Hz, 1H), 7.10 (dd, J=8.0/1.5 Hz, 1H), 7.17 (d, J=7.0 Hz, 1H), 7.31 (d, J=8.0 Hz, 1H), 7.45 (s, 1H), 7.46 (d, J=7.0 Hz, 1H).

EXAMPLE 6

6-(3-(Cyclopropylamino)-6-methylbenzo[d]isoxazol-7-yl)-3,3-dimethylindolin-2-one

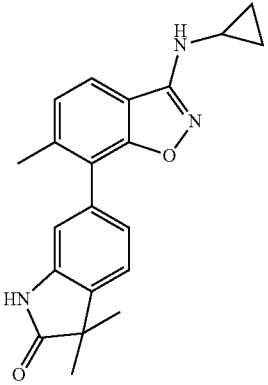 [SMILES: Cc1ccc2c(NC3CC3)noc2c1-c1ccc2c(c1)NC(=O)C2(C)C]

Obtained as a yellowish solid (10%) from 3,3-dimethyl-6-(4,4,5,5-tetramethyl-1,3,2-dioxaborolan-2-yl)indolin-2-one (preparation 9) and N-cyclopropyl-7-iodo-6-methylbenzo[d]isoxazol-3-amine (WO2006094187) following the experimental procedure as described in example 1 followed by purification by flash chromatography (98:2 dichloromethane/methanol).

LRMS (m/z): 348 (M+1)+.

$^1$H-NMR δ (CDCl$_3$): 0.91-0.99 (m, 2H), 1.05-1.14 (m, 2H), 1.72 (s, 6H), 2.33 (s, 1H), 2.66 (s, 3H), 3.03-3.18 (m, 1H), 5.08 (s, 1H), 7.33 (d, J=9.0 Hz, 1H), 7.42 (d, J=6.0 Hz, 1H), 7.53 (d, J=6.0 Hz, 1H), 7.73 (d, J=9.0 Hz, 1H), 8.66 (br s, 1H).

EXAMPLE 7

6'-(3-(cyclopropylamino)-6-methylbenzo[d]isoxazol-7-yl)-2,3,5,6-tetrahydrospiro[pyran-4,3'-pyrrolo[3,2-b]pyridin]-2'(1'H)-one

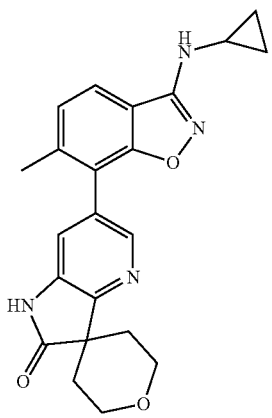 [SMILES: Cc1ccc2c(NC3CC3)noc2c1-c1cnc2c(c1)NC(=O)C21CCOCC1]

Obtained as a white solid (64%) from N-cyclopropyl-7-iodo-6-methyl-1,2-benzisoxazol-3-amine (WO2006094187) and 2'-oxo-1',2,2',3,5,6-hexahydrospiro[pyran-4,3'-pyrrolo[3,2-b]pyridine]-6'-ylboronic acid (preparation 17) following the experimental procedure as described in example 1 followed by purification by reverse phase chromatography (C-18 silica from Waters©, water/acetonitrile/methanol as eluents [0.1% v/v formic acid buffered] 0% to 60%).

LRMS (m/z): 391 (M+1)+.

$^1$H-NMR δ (DMSO-d$_6$): 0.54 (m, 2H), 0.73 (m, 2H), 1.78-1.88 (m, 4H), 2.33 (s, 3H), 2.66 (m, 1H), 3.98 (m, 2H), 4.14 (m, 2H), 7.24-7.29 (m, 2H), 7.70 (d, 1H), 8.17 (s, 1H), 10.77 (s, NH).

EXAMPLE 8

6'-(3-(cyclopropylamino)-6-methylbenzo[d]isoxazol-7-yl)-4-hydroxy-4-methylspiro[cyclohexane-1,3'-pyrrolo[3,2-b]pyridin]-2'(1'H)-one

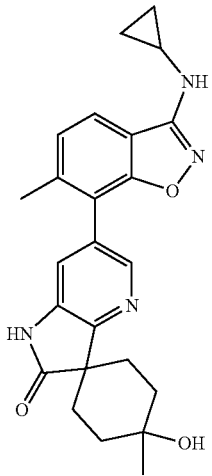 [SMILES: Cc1ccc2c(NC3CC3)noc2c1-c1cnc2c(c1)NC(=O)C21CCC(C)(O)CC1]

Obtained as a grey solid (31%) from 4-hydroxy-4-methyl-2'-oxo-1',2'-dihydrospiro[cyclohexane-1,3'-pyrrolo[3,2-b]pyridine]-6'-ylboronic acid (preparation 21) and N-cyclopropyl-7-iodo-6-methyl-1,2-benzisoxazol-3-amine (WO2006094187) following the experimental procedure as described in example 1 followed by purification by flash chromatography (94:6 dichloromethane/methanol).

LRMS (m/z): 417 (M−1)−.

$^1$H-NMR δ (CD$_3$OD): 0.63 (m, 2H), 0.78 (m, 2H), 1.29 (m, 2H), 1.36 (s, 3H), 1.63 (m, 2H), 1.81 (m, 2H), 2.29 (d, J=6.6 Hz, 2H), 2.38 (s, 3H), 2.66 (m, 1H), 3.12 (m, 1H), 3.47 (m, 1H), 7.24 (d, J=7.9 Hz, 1H), 7.29 (s, 1H), 7.62 (d, J=7.9 Hz, 1H), 8.15 (s, 1H).

EXAMPLE 9

6'-(3-(cyclopropylamino)-6-methylbenzo[d]isoxazol-7-yl)-4-hydroxy-4-methylspiro[cyclohexane-1,3'-pyrrolo[3,2-b]pyridin]-2'(1'H)-one

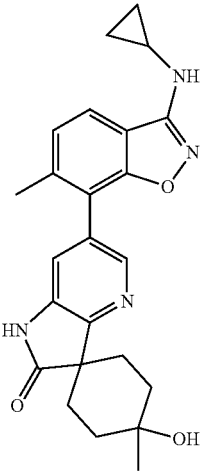 [SMILES: Cc1ccc2c(NC3CC3)noc2c1-c1cnc2c(c1)NC(=O)C21CCC(C)(O)CC1]

Obtained as a white solid (47%) from 4-hydroxy-4-methyl-2'-oxo-1',2'-dihydrospiro[cyclohexane-1,3'-pyrrolo[3,2-b]pyridine]-6'-ylboronic acid (preparation 20) and N-cyclopropyl-7-iodo-6-methyl-1,2-benzisoxazol-3-amine (WO2006094187) following the experimental procedure as described in example 1 followed by purification by reverse phase chromatography (C-18 silica from Waters©, water/acetonitrile/methanol as eluents [0.1% v/v formic acid buffered] 30% to 50%).

LRMS (m/z): 417 (M−1)−.

$^1$H-NMR δ (CD$_3$OD): 0.63 (br s, 2H), 0.79 (br s, 2H), 1.34 (s, 3H), 1.72 (d, J=11.8 Hz, 2H), 1.89 (d, J=12.4 Hz, 2H), 2.16 (t, J=11.8 Hz, 2H), 2.31 (t, J=11.5 Hz, 2H), 2.38 (s, 3H), 2.67 (m, 1H), 7.24 (d, J=7.2 Hz, 1H), 7.29 (s, 1H), 7.63 (d, J=7.2 Hz, 2H), 8.14 (s, 1H).

EXAMPLE 10

6-(3-(4-Methoxybenzylamino)-6-methylbenzo[d]isoxazol-7-yl)-2',3',5',6'-tetrahydrospiro[indoline-3,4'-pyran]-2-one

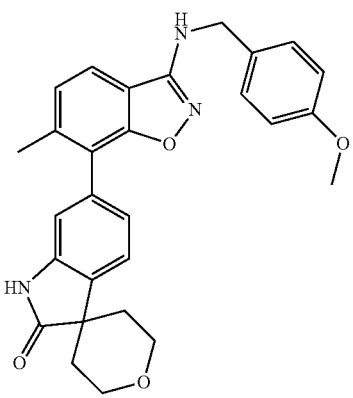 [SMILES: COc1ccc(CNc2noc3c(-c4ccc5c(c4)NC(=O)C54CCOCC4)c(C)ccc23)cc1]

Obtained as a white solid (30%) from 6-(4,4,5,5-tetramethyl-1,3,2-dioxaborolan-2-yl)-2',3',5',6'-tetrahydrospiro[indoline-3,4'-pyran]-2-one (preparation 7) and 7-iodo-N-(4-methoxybenzyl)-6-methylbenzo[d]isoxazol-3-amine (preparation 23) following the experimental procedure as described in example 1 followed by purification by flash chromatography (97:3 dichloromethane:methanol).

LRMS (m/z): 470 (M+1)+.

$^1$H-NMR δ (CDCl$_3$): 1.70 (m, 4H), 2.05 (s, 3H), 2.39 (s, 3H), 3.81 (s, 2H), 3.95-3.99 (m, 2H), 4.25-4.27 (m, 2H). 6.92 (m, 1H), 6.89 (s, 1H), 7.08-7.17 (m, 1H), 7.32-7.47 (m, 5H).

EXAMPLE 11

6-(3-Amino-6-methylbenzo[d]isoxazol-7-yl)-2',3',5',6'-tetrahydrospiro[indoline-3,4'-pyran]-2-one

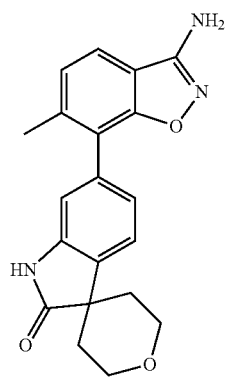 [SMILES: Cc1ccc2c(N)noc2c1-c1ccc2c(c1)NC(=O)C21CCOCC1]

To a solution of 6-(3-(4-methoxybenzylamino)-6-methylbenzo[d]isoxazol-7-yl)-2',3',5',6'-tetrahydrospiro[indoline-3,4'-pyran]-2-one (example 10, 0.12 g, 0.26 mmol) in dichloromethane (2 mL) was added trifluoroacetic acid (2 mL) and the solution was stirred at room temperature for 5 hours. Water and solid sodium hydrogen carbonate were added in order to neutralize the trifluoroacetic acid. Ethyl acetate was added and the organic phase was separated, dried (MgSO$_4$), filtered and evaporated under reduced pressure. The residue was purified by flash chromatography (96:4 dichloromethane/methanol) to yield the title compound (38 mg, 44%) as a white solid.

LRMS (m/z): 350 (M+1)+.

$^1$H-NMR δ (DMSO-d$_6$): 1.76-1.86 (m, 4H), 2.31 (s, 3H), 3.80-3.95 (m, 2H), 4.03-4.12 (m, 2H), 6.36 (s, 2H), 6.85 (s, 1H), 6.99 (d, J=9.0 Hz, 1H), 7.21 (d, J=6.0 Hz, 1H), 7.63 (d, J=9.0 Hz, 1H), 7.67 (d, J=6.0 Hz, 1H), 10.49 (s, 1H).

EXAMPLE 12

6'-(3-amino-6-methylbenzo[d]isoxazol-7-yl)-4-hydroxy-4-methylspiro[cyclohexane-1,3'-indolin]-2'-one

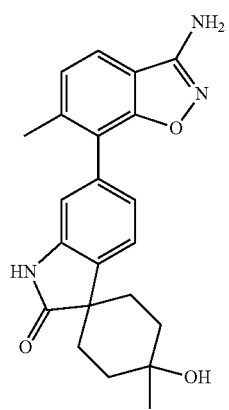 [SMILES: Cc1ccc2c(N)noc2c1-c1ccc2c(c1)NC(=O)C21CCC(C)(O)CC1]

Obtained as a beige solid (62%) from 4-hydroxy-4-methyl-6'-(4,4,5,5-tetramethyl-1,3,2-dioxaborolan-2-yl)spiro[cy-clohexane-1,3'-indolin]-2'-one (preparation 13) and 7-iodo-6-methyl-1,2-benzisoxazol-3-amine (preparation 24) following the experimental procedure as described in example 1 followed by purification by flash chromatography (94:6 dichloromethane/methanol).

LRMS (m/z): 378 (M+1)+.

$^1$H-NMR δ (CD$_3$OD): 1.44 (s, 3H), 1.56 (d, J=13.2 Hz, 2H), 2.00 (m, 4H), 2.35 (m, 2H), 2.42 (s, 3H), 7.02 (s, 1H), 7.09 (d, J=7.7 Hz, 1H), 7.28 (d, J=8.0 Hz, 1H), 7.65 (m, 2H).

EXAMPLE 13

6'-(3-amino-6-methylbenzo[d]isoxazol-7-yl)-4-(2-morpholinoethoxy)spiro[cyclohexane-1,3'-indolin]-2'-one

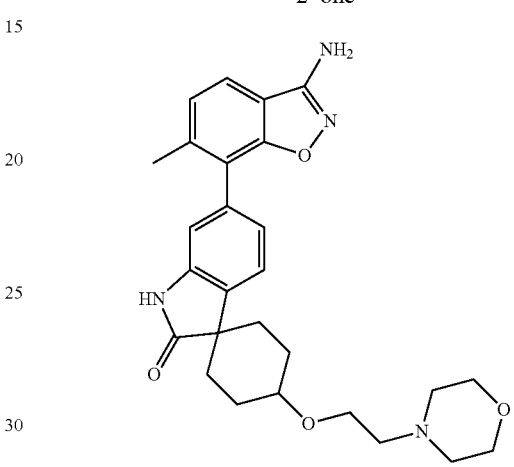

Obtained as a white solid (16%, exact isomeric form not determined) from 7-iodo-6-methyl-1,2-benzisoxazol-3-amine (preparation 24) and 4-(2-morpholinoethoxy)-6'-(4,4,5,5-tetramethyl-1,3,2-dioxaborolan-2-yl)spiro[cyclohexane-1,3'-indolin]-2'-one (preparation 15) following the experimental procedure as described in example 1 followed by purification by flash chromatography (97:3 dichloromethane/methanol).

LRMS (m/z): 477 (M+1)+.

$^1$H-NMR δ (DMSO-d$_6$): 1.61 (m, 2H), 1.91 (m, 4H), 2.0 (m, 2H), 2.31 (s, 3H), 2.44-2.53 (m, 6H), 3.57 (m, 7H), 6.36 (br s, NH$_2$), 6.83 (s, 1H), 6.96 (d, J=7.69 Hz, 1H), 7.21 (d, J=7.97 Hz, 1H), 7.48 (d, J=7.69 Hz, 1H), 7.67 (d, J=7.97 Hz, 1H), 10.36 (br s, NH)

EXAMPLE 14

6'-(3-Amino-6-methyl-1,2-benzisoxazol-7-yl)-4,4-difluorospiro[cyclohexane-1,3'-indol]-2'(1'H)-one

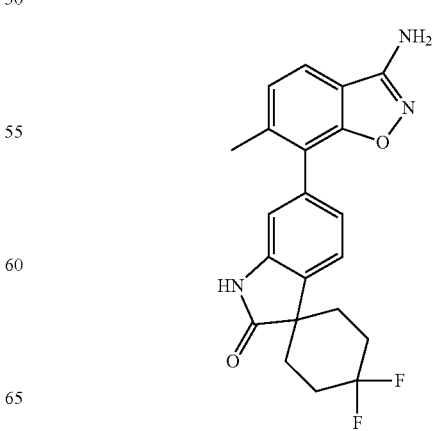

a) 4,4-difluoro-6'-{3-[(4-methoxybenzyl)amino]-6-methyl-1,2-benzisoxazol-7-yl}spiro[cyclohexane-1,3'-indol]-2'(1'H)-one Obtained as a light yellow solid (96%) from 7-iodo-N-(4-methoxybenzyl)-6-methylbenzo[d]isoxazol-3-amine (preparation 23) and 4,4-difluoro-6'-(4,4,5,5-tetramethyl-1,3,2-dioxaborolan-2-yl)spiro[cyclohexane-1,3'-indolin]-2'-one (preparation 11) following the experimental procedure as described in example 1 followed by purification by flash chromatography (dichloromethane to 9:1 dichloromethane/methanol).

LRMS (m/z): 384 (M+1)⁺.

b) 6'-(3-Amino-6-methyl-1,2-benzisoxazol-7-yl)-4,4-difluorospiro[cyclohexane-1,3'-indol]-2'(1'H)-one Obtained as a white solid (57%) from 4,4-difluoro-6'-{3-[(4-methoxybenzyl)amino]-6-methyl-1,2-benzisoxazol-7-yl}spiro[cyclohexane-1,3'-indol]-2'(1'H)-one (example 14a) following the experimental procedure as described for example 11 followed by purification by flash chromatography (dichloromethane to 90:10 dichloromethane/methanol).

LRMS (m/z): 504 (M+1)⁺.

¹H-NMR δ (DMSO-d₆): 1.89-2.00 (m, 4H), 2.08-2.20 (m, 2H), 2.31 (s, 3H), 2.39-2.50 (m, 2H), 6.36 (s, 1H), 6.85 (s, 1H), 6.99 (d, J=8.0 Hz, 1H), 7.21 (d, J=8.0 Hz, 1H), 7.50 (d, J=9.0 Hz, 1H), 7.67 (d, J=9.0 Hz, 1H), 10.57 (s, 1H).

EXAMPLE 15

6-(3-Amino-6-methyl-1,2-benzisoxazol-7-yl)-3,3-dimethyl-1,3-dihydro-2H-indol-2-one

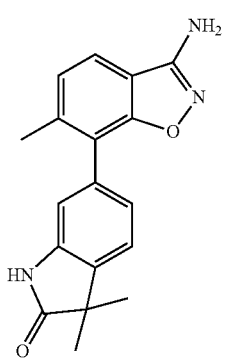 [SMILES: Cc1ccc2c(N)noc2c1-c1ccc2c(c1)NC(=O)C2(C)C]

Obtained as a solid (94%) from 7-iodo-6-methylbenzo[d]isoxazol-3-amine (preparation 24) and 3,3-dimethyl-6-(4,4,5,5-tetramethyl-1,3,2-dioxaborolan-2-yl)indolin-2-one (preparation 9) following the experimental procedure as described in example 1 followed by purification by flash chromatography (dichloromethane to 9:1 dichloromethane/methanol).

LRMS (m/z): 308 (M+1)⁺.

¹H-NMR δ (CD₃OD): 1.41 (s, 6H), 2.35 (s, 3H), 6.93 (s, 1H), 7.03 (d, J=9.0 Hz, 1H), 7.21 (d, J=9.0 Hz, 1H), 7.35 (d, J=8.0 Hz, 1H), 7.60 (d, J=8.0 Hz, 1H).

EXAMPLE 16

6-(3-Amino-6-methyl-1H-indazol-7-yl)-2',3',5',6'-tetrahydrospiro[indoline-3,4'-pyran]-2-one

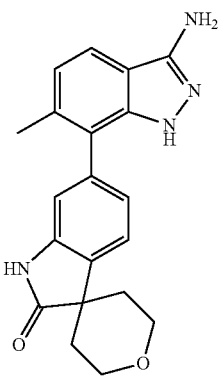 [SMILES: Cc1ccc2c(N)n[nH]c2c1-c1ccc2c(c1)NC(=O)C21CCOCC1]

Obtained as a white solid (29%) from 6-(4,4,5,5-tetramethyl-1,3,2-dioxaborolan-2-yl)-2',3',5',6'-tetrahydrospiro[indoline-3,4'-pyran]-2-one (preparation 7) and 7-iodo-6-methyl-1H-indazol-3-amine (preparation 25) following the experimental procedure as described in example 1 followed by purification by flash chromatography (95:5 dichloromethane/methanol).

LRMS (m/z): 349 (M+1)⁺.

¹H-NMR δ (DMSO-d₆): 1.75-1.85 (m, 4H), 2.20 (s, 3H), 3.80-3.90 (m, 2H), 4.03-4.12 (m, 2H), 5.26 (s, 2H), 6.79 (s, 1H), 6.84 (d, J=8.0 Hz, 1H), 6.93 (d, J=6.0 Hz, 1H), 7.53 (d, J=6.0 Hz, 1H), 7.61 (d, J=8.0 Hz, 1H), 10.48 (s, 1H), 10.90 (s, 1H).

EXAMPLE 17

6'-[3-(Cyclopropylamino)[1,2,4]-triazolo[4,3-a]pyridin-8-yl]spiro[cyclopentane-1,3'-indol]-2'(1'H)-one

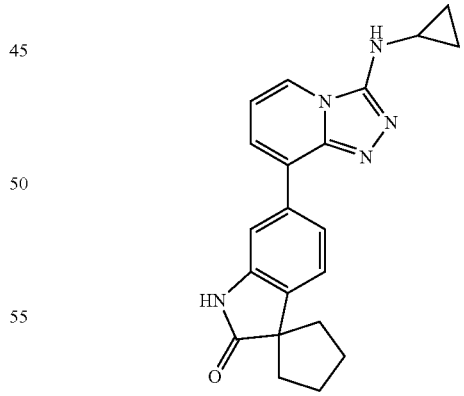

Obtained as a white solid (2%) from N-cyclopropyl-8-iodo-[1,2,4]triazolo[4,3-a]pyridin-3-amine (preparation 26) and 6'-(4,4,5,5-tetramethyl-1,3,2-dioxaborolan-2-yl)spiro[cyclopentane-1,3'-indol]-2'-one (preparation 4) following the experimental procedure as described in example 1 followed by purification by flash chromatography (dichloromethane to 85:15 dichloromethane/methanol).

LRMS (m/z): 360 (M+1)⁺.

EXAMPLE 18

6'-(3-Amino[1,2,4]triazolo[4,3-a]pyridin-8-yl)spiro[cyclopentane-1,3'-indol]-2'(1'H)-one

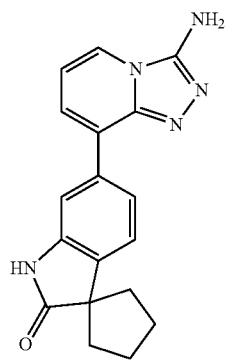 [SMILES: Nc1nnc2c(-c3ccc4c(c3)NC(=O)C43CCCC3)cccn12]

Obtained as a by-product (12%) from N-cyclopropyl-8-iodo-[1,2,4]triazolo[4,3-a]pyridin-3-amine (preparation 26) and 6'-(4,4,5,5-tetramethyl-1,3,2-dioxaborolan-2-yl)spiro[cyclopentane-1,3'-indolin]-2'-one (preparation 4) following the experimental procedure as described in example 1 followed by purification by flash chromatography (dichloromethane to 85:15 dichloromethane/methanol).

LRMS (m/z): 320 (M+1)$^+$.

$^1$H-NMR δ (DMSO-d$_6$): 1.75-2.05 (m, 8H), 6.44 (s, 2H), 6.85 (d, J=8.0, 1H), 7.34 (d, J=6.0 Hz, 1H), 7.62 (d, J=8.0 Hz, 1H), 7.80 (s, 1H), 8.04 (d, J=6.0 Hz, 1H).

EXAMPLE 19

6'-{3-[(Cyclopropylmethyl)amino][1,2,4]triazolo[4,3-a]pyridin-8-yl}spiro-[cyclopentane-1,3'-indol]-2'(1'H)-one

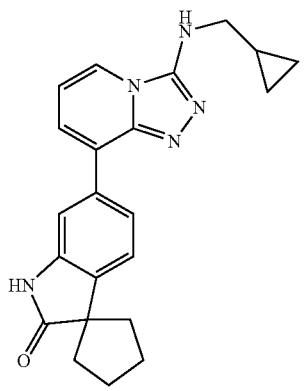 [SMILES: O=C1Nc2cc(-c3cccn4c(NCC5CC5)nnc34)ccc2C12CCCC2]

Obtained as a solid (20%) from N-(cyclopropylmethyl)-8-iodo[1,2,4]triazolo[4,3-a]pyridin-3-amine (preparation 27) and 6'-(4,4,5,5-tetramethyl-1,3,2-dioxaborolan-2-yl)spiro[cyclopentane-1,3'-indolin]-2'-one (preparation 4) following the experimental procedure as described in example 1.

LRMS (m/z): 374 (M+1)$^+$.

$^1$H-NMR δ (DMSO-d$_6$): 0.28-0.33 (m, 2H), 0.47-0.53 (m, 2H), 1.17-1.26 (m, 1H), 1.78-2-02 (m, 8H), 3.28 (m, 2H), 6.80 (t, J=5.5 Hz, 1H), 6.86 (m, 1H), 7.33 (d, J=6.9 Hz, 1H), 7.36 (d, J=7.7 Hz, 1H), 7.63 (dd, J=1.4/7.7 Hz, 1H), 7.75 (d, J=1.4 Hz, 1H), 8.14 (d, J=6.9 Hz, 1H), 10.47 (s, 1H).

EXAMPLE 20

6'-(3-(cyclopropylmethylamino)-7-methyl-[1,2,4]triazolo[4,3-a]pyridin-8-yl)spiro[cyclopentane-1,3'-indolin]-2'-one

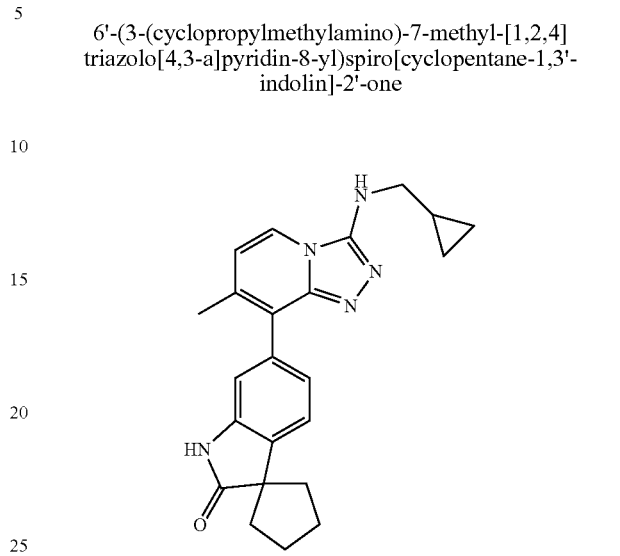

Obtained as a white solid (49%) from 6'-(4,4,5,5-tetramethyl-1,3,2-dioxaborolan-2-yl)spiro[cyclopentane-1,3'-indolin]-2'-one (preparation 4) and N-(cyclopropylmethyl)-8-iodo-7-methyl-[1,2,4]triazolo[4,3-a]pyridin-3-amine (preparation 28) following the experimental procedure as described in example 1 followed by purification by flash chromatography (98:2 dichloromethane/methanol).

LRMS (m/z): 388 (M+1)$^+$.

$^1$H-NMR δ (DMSO-d$_6$): 0.27-0.31 (m, 2H), 0.45-0.52 (m, 2H), 1.11-1.21 (m, 1H), 1.80-2.05 (m, 8H), 2.16 (s, 3H), 3.27 (m, 2H), 6.64 (t, J=6.6 Hz, 1H), 6.71 (d, J=7.0 Hz, 1H), 6.89 (s, 1H), 7.00 (d, J=7.6 Hz, 1H), 7.33 (d, J=7.6 Hz, 1H), 8.02 (d, J=7.0 Hz, 1H), 10.37 (s, 1H).

The invention claimed is:
1. A compound of formula (I)

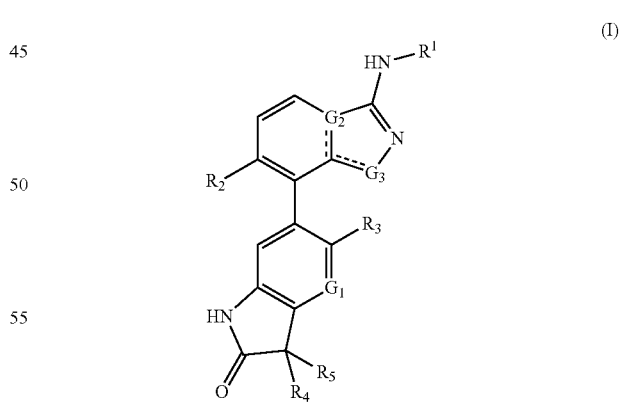

wherein:
R$^1$ is chosen from a hydrogen atom, C$_{3-6}$ cycloalkyl groups, C$_{3-6}$ cycloalkyl-C$_{1-2}$ alkylene groups, and C$_{5-10}$ aryl-C$_{1-2}$ alkylene groups, wherein the cycloalkyl groups and aryl groups are optionally substituted by 1 or 2 substituents chosen from linear C$_{1-4}$ alkyl groups, branched C$_{1-4}$ alkyl groups, and C$_{1-4}$ alkoxy groups;
R$^2$ is chosen from a hydrogen atom and a methyl group;

$R^3$ is chosen from a hydrogen atom and halogen atoms;
$R^4$ and $R^5$ each independently is chosen from $C_{1-3}$ alkyl groups, or $R^4$ and $R^5$ form together with the carbon atom to which they are attached a cyclic group of formula

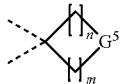

wherein n and m each independently is an integer chosen from 1 and 2, and $G^5$ is chosen from —O— and —C($R^7R^8$)—, wherein:
$R^7$ is chosen from a hydrogen atom, halogen atoms, a hydroxyl group, morpholine groups, and morpholinoethoxy groups;
$R^8$ is chosen from a hydrogen atom, halogen atoms, and $C_{1-4}$ alkyl groups;
$G^1$ is chosen from a nitrogen atom and —CH=;
$G^2$ is chosen from a nitrogen atom and an aromatic carbon atom; and
$G^3$ is chosen from a nitrogen atom and an oxygen atom;
or a pharmaceutically acceptable salt or an N-oxide thereof.

2. The compound according to claim 1, wherein $R^1$ is chosen from a hydrogen atom, a cyclopropyl group, cyclopropylmethyl groups, and a benzyl group, wherein the benzyl group is optionally substituted by a methoxy group.

3. The compound according to claim 2, wherein $R^1$ is chosen from a hydrogen atom and a cyclopropyl group.

4. The compound according to claim 1, wherein $R^2$ is a methyl group.

5. The compound according to claim 1, wherein $R^3$ is a hydrogen atom.

6. The compound according to claim 1, wherein $R^4$ and $R^5$ each independently is a methyl group, or $R^4$ and $R^5$ form together with the carbon atom to which they are attached a cyclic group of formula

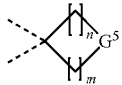

wherein n and m each independently is an integer chosen from 1 and 2, and $G^5$ is chosen from —O— and —C($R^7R^8$)—, wherein:
$R^7$ is chosen from a hydrogen atom, a fluorine atom, a hydroxyl group, and morpholino-ethoxy groups and
$R^8$ is chosen from a hydrogen atom, a fluorine atom, and a methyl group.

7. The compound according to claim 1, wherein $G^2$ is an aromatic carbon atom.

8. The compound according to claim 1, wherein $G^3$ is an oxygen atom.

9. The compound according to claim 1, wherein:
$R^1$ is chosen from a hydrogen atom and a cyclopropyl group;
$R^2$ is a methyl group;
$R^3$ is a hydrogen atom;
$R^4$ and $R^5$ each independently is a methyl group, or $R^4$ and $R^5$ form together with the carbon atom to which they are attached a cyclic group of formula

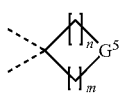

wherein n and m each independently is an integer chosen from 1 and 2, and $G^5$ is chosen from —O— and —C($R^7R^8$)—, wherein:
$R^7$ is chosen from a hydrogen atom, a fluorine atom, a hydroxyl group, and morpholino-ethoxy groups;
$R^8$ is chosen from a hydrogen atom, a fluorine atom, and a methyl group;
$G^2$ is an aromatic carbon atom; and
$G^3$ is an oxygen atom.

10. The compound according to claim 1, wherein the compound of formula (I) is chosen from:
6'-(3-(Cyclopropylamino)-6-methylbenzo[d]isoxazol-7-yl)spiro[cyclopentane-1,3'-indolin]-2'-one;
6'-(3-(Cyclopropylamino)-benzo[d]isoxazol-7-yl)spiro [cyclopentane-1,3'-indolin]-2'-one;
5'-Chloro-6'-(3-(cyclopropylamino)benzo[d]isoxazol-7-yl)spiro[cyclopentane-1,3'-indolin]-2'-one;
6-(3-(Cyclopropylamino)-6-methylbenzo[d]isoxazol-7-yl)-2',3',5',6'-tetrahydrospiro [indoline-3,4'-pyran]-2-one;
6'-(3-(Cyclopropylamino)-6-methylbenzo[d]isoxazol-7-yl)-4,4-difluorospiro[cyclohexane-1,3'-indolin]-2'-one;
6-(3-(Cyclopropylamino)-6-methylbenzo[d]isoxazol-7-yl)-3,3-dimethylindolin-2-one;
6'-(3-(Cyclopropylamino)-6-methylbenzo[d]isoxazol-7-yl)-2,3,5,6-tetrahydrospiro[pyran-4,3'-pyrrolo[3,2-b]pyridin]-2'(1'H)-one;
6'-(3-(Cyclopropylamino)-6-methylbenzo[d]isoxazol-7-yl)-4-hydroxy-4-methylspiro [cyclohexane-1,3'-pyrrolo[3,2-b]pyridin]-2'(1'H)-one;
6'-(3-(Cyclopropylamino)-6-methylbenzo[d]isoxazol-7-yl)-4-hydroxy-4-methylspiro [cyclohexane-1,3'-pyrrolo[3,2-b]pyridin]-2'(1'H)-one;
6-(3-(4-Methoxybenzylamino)-6-methylbenzo[d]isoxazol-7-yl)-2',3',5',6'-tetrahydrospiro [indoline-3,4'-pyran]-2-one;
6-(3-Amino-6-methylbenzo[d]isoxazol-7-yl)-2',3',5',6'-tetrahydrospiro[indoline-3,4'-pyran]-2-one;
6'-(3-Amino-6-methylbenzo[d]isoxazol-7-yl)-4-hydroxy-4-methylspiro[cyclohexane-1,3'-indolin]-2'-one;
6'-(3-Amino-6-methylbenzo[d]isoxazol-7-yl)-4-(2-morpholinoethoxy)spiro[cyclohexane-1,3'-indolin]-2'-one;
6'-(3-Amino-6-methyl-1,2-benzisoxazol-7-yl)-4,4-difluorospiro[cyclohexane-1,3'-indol]-2'(1'H)-one;
6-(3-Amino-6-methyl-1,2-benzisoxazol-7-yl)-3,3-dimethyl-1,3-dihydro-2H-indol-2-one;
6-(3-Amino-6-methyl-1H-indazol-7-yl)-2',3',5',6'-tetrahydrospiro[indoline-3,4'-pyran]-2-one;
6'-[3-(Cyclopropylamino)[1,2,4]triazolo[4,3-a]pyridin-8-yl]spiro[cyclopentane-1,3'-indol]-2'(1'H)-one;
6'-(3-Amino[1,2,4]triazolo[4,3-a]pyridin-8-yl)spiro[cyclopentane-1,3'-indol]-2'(1'H)-one;
6'-{3-[(Cyclopropylmethyl)amino][1,2,4]triazolo[4,3-a]pyridin-8-yl}spiro-[cyclopentane-1,3'-indol]-2'(1'H)-one; and
6'-(3-(Cyclopropylmethylamino)-7-methyl-[1,2,4]triazolo[4,3-a]pyridin-8-yl)spiro[cyclopentane-1,3'-indolin]-2'-one.

11. A pharmaceutical composition comprising the compound according to claim 1 and a pharmaceutically acceptable diluent or carrier.

12. A composition comprising:
(i.) the compound according to claim 1; and
(ii.) another compound chosen from (1) antagonists of M3 muscarinic receptors, (2) β2-agonists, (3) PDE4 inhibitors, (4) corticosteroids, (5) leukotriene D4 antagonists, (6) inhibitors of egfr-kinase, (7) antagonists of the A2B adenosine receptor, (8) NK1 receptor agonists, (9) CRTh2 antagonists, (10) syk kinase inhibitors, (11) CCR3 antagonists, (12) VLA-4 antagonists, (13) methotrexate, (14) JAK3 inhibitors, (15) DHODH inhibitors, and (16) a disease modifying antirheumatic drug (DMARD).

* * * * *